United States Patent
Han et al.

(10) Patent No.: US 6,632,812 B2
(45) Date of Patent: Oct. 14, 2003

(54) SUBSTITUTED LACTAMS AS INHIBITORS OF Aβ PROTEIN PRODUCTION

(75) Inventors: Qi Han, Hockessin, DE (US); Hong Liu, Glen Mills, PA (US); Richard E. Olson, Wilmington, DE (US); Michael G. Yang, Wilmington, DE (US)

(73) Assignee: Dupont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/832,455

(22) Filed: Apr. 11, 2001

(65) Prior Publication Data

US 2002/0025955 A1 Feb. 28, 2002

Related U.S. Application Data

(60) Provisional application No. 60/196,549, filed on Apr. 11, 2000.

(51) Int. Cl.⁷ .................. C07D 243/24; C07D 401/04; C07D 223/18; C07D 223/12; A61K 31/55

(52) U.S. Cl. ....................... 514/221; 540/509

(58) Field of Search ................... 540/509; 514/221

(56) References Cited

PUBLICATIONS

Olson et al. (WO 2000/007,995) Feb. 17, 2000; Abstract.*
Olson (WO 2000/038,618) Jul. 6, 2000; Abstract.*

* cited by examiner

*Primary Examiner*—Bruck Kifle
(74) *Attorney, Agent, or Firm*—Bristol-Myers Squibbs Co.; Aldo A. Algieri

(57) ABSTRACT

This invention relates to novel lactams of Formula (I):

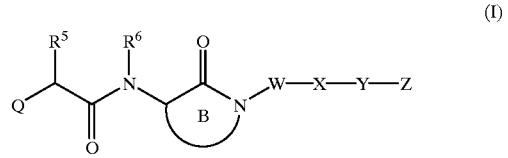

having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

27 Claims, No Drawings

SUBSTITUTED LACTAMS AS INHIBITORS OF Aβ PROTEIN PRODUCTION

This application claims the benefit of U.S. Provisional Application No. 60/196,549, filed Apr. 11, 2000.

FIELD OF THE INVENTION

This invention relates to novel lactams having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

BACKGROUND OF THE INVENTION

Alzheimer's disease (AD) is a degenerative brain disorder characterized clinically by progressive loss of memory, temporal and local orientation, cognition, reasoning, judgment and emotionally stability. AD is a common cause of progressive dementia in humans and is one of the major causes of death in the United States. AD has been observed in all races and ethnic groups worldwide, and is a major present and future health problem. No treatment that effectively prevents AD or reverses the clinical symptoms and underlying pathophysiology is currently available (for review see Dennis J. Selkoe; Cell Biology of the amyloid (beta)-protein precursor and the mechanism of Alzheimer's disease, Annu Rev Cell Biol, 1994, 10: 373–403).

Histopathological examination of brain tissue derived upon autopsy or from neurosurgical specimens in effected individuals revealed the occurrence of amyloid plaques and neurofibrillar tangles in the cerebral cortex of such patients. Similar alterations were observed in patients with Trisomy 21 (Down's syndrome), and hereditary cerebral hemorrhage with amyloidosis of the Dutch-type. Neurofibrillar tangles are nonmembrane-bound bundles of abnormal proteinaceous filaments and biochemical and immunochemical studies led to the conclusion that their principle protein subunit is an altered phosphorylated form of the tau protein (reviewed in Selkoe, 1994).

Biochemical and immunological studies revealed that the dominant proteinaceous component of the amyloid plaque is an approximately 4.2 kilodalton (kD) protein of about 39 to 43 amino acids. This protein was designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Aβ was first purified and a partial amino acid reported in 1984 (Glenner and Wong, Biochem. Biophys. Res. Commun. 120: 885–890). The isolation and sequence data for the first 28 amino acids are described in U.S. Pat. No 4,666,829.

Compelling evidence accumulated during the last decade revealed that Aβ is an internal polypeptide derived from a type 1 integral membrane protein, termed β amyloid precursor protein (APP). β APP is normally produced by many cells both in vivo and in cultured cells, derived from various animals and humans. Aβ is derived from cleavage of β APP by as yet unknown enzyme (protease) system(s), collectively termed secretases.

The existence of at least four proteolytic activities has been postulated. They include β secretase(s), generating the N-terminus of Aβ, α secretase(s) cleaving around the 16/17 peptide bond in Aβ, and γ secretases, generating C-terminal Aβ fragments ending at position 38, 39, 40, 42, and 43 or generating C-terminal extended precursors which are subsequently truncated to the above polypeptides.

Several lines of evidence suggest that abnormal accumulation of Aβ plays a key role in the pathogenesis of AD. Firstly, Aβ is the major protein found in amyloid plaques. Secondly, Aβ is neurotoxic and may be causally related to neuronal death observed in AD patients. Thirdly, missense DNA mutations at position 717 in the 770 isoform of β APP can be found in effected members but not unaffected members of several families with a genetically determined (familiar) form of AD. In addition, several other β APP mutations have been described in familiar forms of AD. Fourthly, similar neuropathological changes have been observed in transgenic animals overexpressing mutant forms of human β APP. Fifthly, individuals with Down's syndrome have an increased gene dosage of β APP and develop early-onset AD. Taken together, these observations strongly suggest that Aβ depositions may be causally related to the AD.

It is hypothesized that inhibiting the production of Aβ will prevent and reduce neurological degeneration, by controlling the formation of amyloid plaques, reducing neurotoxicity and, generally, mediating the pathology associated with Aβ production. One method of treatment methods would therefore be based on drugs that inhibit the formation of Aβ in vivo. Methods of treatment could target the formation of Aβ through the enzymes involved in the proteolytic processing of β amyloid precursor protein. Compounds that inhibit β or γ secretase activity, either directly or indirectly, could control the production of Aβ. Advantageously, compounds that specifically target γ secretases, could control the production of Aβ. Such inhibition of β or γ secretases could thereby reduce production of Aβ, which, thereby, could reduce or prevent the neurological disorders associated with Aβ protein.

PCT publication number WO 96/29313 discloses the general formula:

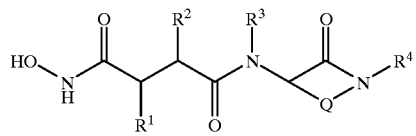

covering metalloprotease inhibiting compounds useful for the treatment of diseases associated with excess and/or unwanted matrix metalloprotease activity, particularly collagenase and or stromelysin activity.

Compounds of general formula:

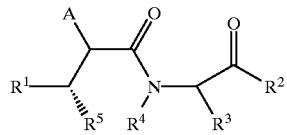

are disclosed in PCT publication number WO 95/22966 relating to matrix metalloprotease inhibitors. The compounds of the invention are useful for the treatment of conditions associated with the destruction of cartilage, including corneal ulceration, osteoporosis, periodontitis and cancer. European Patent Application number EP 0652009A1 relates to the general formula:

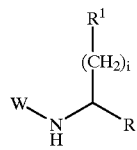

and discloses compounds that are protease inhibitors that inhibit Aβ production. U.S. Pat. No. 5,703,129 discloses the general formula:

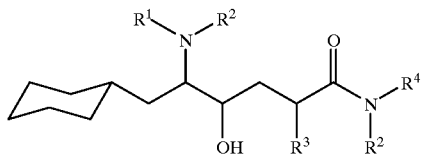

which covers 5-amino-6-cyclohexyl-4-hydroxy-hexanamide derivatives that inhibit Aβ production and are useful in the treatment of Alzheimer's disease.

Copending, commonly assigned U.S. patent application Ser. No. 09/370,089 filed Aug. 7, 1999 (equivalent to international application PCT US99/17717) discloses lactams of general formula:

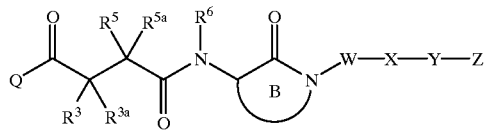

wherein the lactam ring B is substituted by succinamide and a carbocyclic, aryl, or heteroaryl group. These compounds inhibit the processing of amyloid precursor protein and, more specifically, inhibit the production of Aβ-peptide, thereby acting to prevent the formation of neurological deposits of amyloid protein.

None of the above references teaches or suggests the compounds of the present invention which are described in detail below.

SUMMARY OF THE INVENTION

One object of the present invention is to provide novel compounds which are useful as inhibitors of the production of Aβ protein or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating degenerative neurological disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of Formula (I):

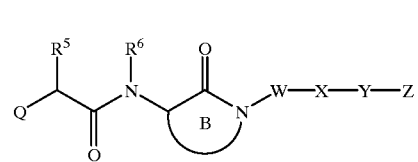

or pharmaceutically acceptable salt or prodrug forms thereof, wherein Q, $R^5$, $R^6$, W, X, Y, Z, and ring B are defined below, are effective inhibitors of the production of Aβ.

DETAILED DESCRIPTION OF PREFERRED EMBODIMENTS

[1] Thus, in a first embodiment, the present invention provides a novel compound of Formula (I):

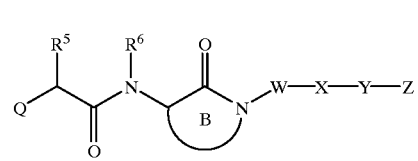

or a pharmaceutically acceptable salt or prodrug thereof, wherein:

Q is $-(CR^7R^{7a})_m-R^4$, $-(CR^7R^{7a})_n-S-R^4$, $-(CR^7R^{7a})_n-O-R^4$, $-(CR^7R^{7a})_m-N(R^{7b})-R^4$, $-(CR^7R^{7a})_n-S(=O)-R^4$, $-(CR^7R^{7a})_n-S(=O)_2-R^4$, or $-(CR^7R^{7a})_n-C(=O)-R^4$; provided when n is 0, then $R^4$ is not H;

m is 1, 2, or 3;

n is 0, 1, or 2;

$R^4$ is H,
 $C_1-C_8$ alkyl substituted with 0–3 $R^{4a}$,
 $C_2-C_8$ alkenyl substituted with 0–3 $R^{4a}$,
 $C_2-C_8$ alkynyl substituted with 0–3 $R^{4a}$,
 $C_3-C_{10}$ carbocycle substituted with 0–3 $R^{4b}$,
 $C_6-C_{10}$ aryl substituted with 0–3 $R^{4b}$, or
 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from is H, Cl, F, Br, I, CN, $NO_2$, $NR^{15}R^{16}$, $CF_3$, $OR^{14a}$, $OR^{22}$, $SR^{22}$, $C(=O)OR^{22}$, $NR^{21}R^{22}$, $S(=O)R^{22}$, $S(=O)_2R^{22}$,
 $C_1-C_6$ alkyl, $C_1-C_4$ alkoxy, $C_1-C_4$ haloalkyl,
 $C_1-C_4$ haloalkoxy, $C_1-C_4$ haloalkyl-S—,
 $C_3-C_{10}$ carbocycle substituted with 0–3 $R^{4b}$,
 $C_6-C_{10}$ aryl substituted with 0–3 $R^{4b}$, and
 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
 $C_1-C_6$ alkyl, $C_1-C_4$ alkoxy, $C_1-C_4$ haloalkyl,
 $C_1-C_4$ haloalkoxy, and $C_1-C_4$ haloalkyl-S—;

$R^5$ is H;
 $C_1-C_6$ alkyl substituted with 0–3 $R^{5b}$;
 $C_2-C_6$ alkenyl substituted with 0–3 $R^{5b}$;
 $C_2-C_6$ alkynyl substituted with 0–3 $R^{5b}$;

$C_3$–$C_{10}$ carbocycle substituted with 0–3 $R^{5c}$;
$C_6$–$C_{10}$ aryl substituted with 0–3 $R^{5c}$; and
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from:
H, $C_1$–$C_6$ alkyl, $CF_3$, Cl, F, Br, I, =O, CN, $NO_2$, $NR^{15}R^{16}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl, and $C_1$–$C_4$ haloalkoxy, and $C_1$–$C_4$ haloalkyl-S—;

$R^6$ is H;
$C_1$–$C_6$ alkyl substituted with 0–3 $R^{6a}$;
$C_3$–$C_{10}$ carbocycle substituted with 0–3 $R^{6b}$; or
$C_6$–$C_{10}$ aryl substituted with 0–3 $R^{6b}$;

$R^{6a}$, at each occurrence, is independently selected from H, $C_1$–$C_6$ alkyl, $OR^{14}$, Cl, F, Br, I, =O, CN, $NO_2$, $NR^{15}R^{16}$, aryl or $CF_3$;

$R^{6b}$, at each occurrence, is independently selected from H, OH, Cl, F, Br, I, CN, $NO_2$, $NR^{15}R^{16}$, $CF_3$, $C_1$–$C_6$ alkyl, $C_1$–$C_4$ alkoxy, $C_1$–$C_4$ haloalkyl, and $C_1$–$C_4$ haloalkoxy;

$R^7$, at each occurrence, is independently H or $C_1$–$C_4$ alkyl;

$R^{7a}$, at each occurrence, is independently H or $C_1$–$C_4$ alkyl;

$R^{7b}$ is H or $C_1$–$C_4$ alkyl;

Ring B is a 7 membered lactam,
wherein the lactam is saturated, partially saturated or unsaturated;
wherein each additional lactam carbon is substituted with 0–2 $R^{11}$; and,
optionally, the lactam contains a heteroatom selected from —O—, —S—, —S(=O)—, —S(=O)$_2$—, —N=, —NH—, and —N($R^{10}$)—;

additionally, two $R^{11}$ substituents on adjacent atoms may be combined to form a benzo fused radical; wherein said benzo fused radical is substituted with 0–4 $R^{13}$;

additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{13}$;

additionally, two $R^{11}$ substituents on the same or adjacent carbon atoms may be combined to form a $C_3$–$C_6$ carbocycle substituted with 0–3 $R^{13}$;

$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
$C_1$–$C_6$ alkyl optionally substituted with 0–3 $R^{10a}$;
$C_6$–$C_{10}$ aryl substituted with 0–4 $R^{10b}$;
$C_3$–$C_{10}$ carbocycle substituted with 0–3 $R^{10b}$; or
5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10a}$, at each occurrence, is independently selected from H,
$C_1$–$C_6$ alkyl, $OR^{14}$, Cl, F, Br, I, =O, CN, $NO_2$, $NR^{15}R^{16}$, $CF_3$, or aryl substituted with 0–4 $R^{10b}$;

$R^{10b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$–$C_6$ alkyl optionally substituted with 0–3 $R^{11a}$;
$C_6$–$C_{10}$ aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
phenyl substituted with 0–3 $R^{11b}$;
$C_3$–$C_6$ cycloalkyl substituted with 0–3 $R^{11b}$; and
5 to 6 membered heterocycle containing 1 to 3 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond or —$(CR^8R^{8a})_p$—;

p is 0, 1, 2, 3, or 4;

$R^8$ and $R^{8a}$, at each occurrence, are independently selected from H, F, $C_1$–$C_4$ alkyl, $C_2$–$C_4$ alkenyl, $C_2$–$C_4$ alkynyl and $C_3$–$C_8$ cycloalkyl;

X is a bond;
$C_6$–$C_{10}$ aryl substituted with 0–3 $R^{Xb}$;
$C_3$–$C_{10}$ carbocycle substituted with 0–3 $R^{Xb}$; or
5 to 10 membered heterocycle substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkoxy;

Y is a bond or —$(CR^9R^{9a})_t$—V—$(CR^9R^{9a})_u$—;

t is 0, 1, or 2;

u is 0, 1, or 2;

$R^9$ and $R^{9a}$, at each occurrence, are independently selected from H, F, $C_1$–$C_6$ alkyl or $C_3$–$C_8$ cycloalkyl;

V is a bond, —C(=O)—, —O—, —S—, —S(=O)—, —S(=O)$_2$—, —N($R^{19}$)—, C(=O)$NR^{19b}$—, —$NR^{19b}$C(=O)—, —$NR^{19b}$S(=O)$_2$—, —S(=O)$_2$$NR^{19b}$—, —$NR^{19b}$S(=O)—, —S(=O)$NR^{19b}$—, —C(=O)O—, or —OC(=O)—;

Z is H;
$C_1$–$C_8$ alkyl substituted with 0–3 $R^{12a}$;
$C_2$–$C_6$ alkenyl substituted with 0–3 $R^{12a}$;
$C_2$–$C_6$ alkynyl substituted with 0–3 $R^{12a}$;
$C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, aryl, $C_3$–$C_6$ cycloalkyl, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, OH, $C_1$–$C_6$ alkyl, benzyl, phenethyl, ($C_1$–$C_6$ alkyl)-C(=O)—, and ($C_1$–$C_6$ alkyl)-S(=O)$_2$—;

alternatively, $R^{15}$ and $R^{16}$, together with the nitrogen to which they are attached, may combine to form a 4–7 membered ring wherein said 4–7 membered ring optionally contains an additional heteroatom selected from O or NH;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, S(O)$CH_3$, $SO_2CH_3$, —$NH_2$, —N($CH_3$)$_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19b}$, at each occurrence, is independently is H or $C_1$–$C_4$ alkyl;

$R^{21}$ is H, phenyl, benzyl, or $C_1$–$C_4$ alkyl; and $R^{22}$ is $C_1$–$C_4$ alkyl, $C_2$–$C_4$ alkenyl, or $C_3$–$C_4$ alkynyl.

[2] In a preferred embodiment, the present invention provides for a compound of Formula (I), or a pharmaceutically acceptable salt or prodrug thereof, wherein:

Q is —($CR^7R^{7a}$)$_m$—$R^4$, —($CR^7R^{7a}$)$_n$—S—$R^4$, —($CR^7R^{7a}$)$_n$—O—$R^4$, or —($CR^7R^{7a}$)$_m$—N($R^{7b}$)—$R^4$;

m is 1 or 2;

n is 0 or 1;

$R^4$ is H, $C_1$–$C_8$ alkyl substituted with 0–3 $R^{4a}$, $C_2$–$C_8$ alkenyl substituted with 0–3 $R^{4a}$, $C_2$–$C_8$ alkynyl substituted with 0–3 $R^{4a}$, $C_3$–$C_{10}$ carbocycle substituted with 0–3 $R^{4b}$, $C_6$–$C_{10}$ aryl substituted with 0–3 $R^{4b}$, or 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from is H, Cl, F, Br, I, CN, $NO_2$, $NR^{15}R^{16}$, $CF_3$, $OR^{14a}$, C(=O)$OR^{22}$, $SR^{22}$, $OR^{22}$, $NR^{21}R^{22}$, S(=O)$R^{22}$, S(=O)$_2R^{22}$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_3$–$C_{10}$ carbocycle substituted with 0–3 $R^{4b}$, $C_6$–$C_{10}$ aryl substituted with 0–3 $R^{4b}$, and 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ is H;

$C_1$–$C_6$ alkyl substituted with 0–3 $R^{5b}$;

$C_2$–$C_6$ alkenyl substituted with 0–3 $R^{5b}$;

$C_2$–$C_6$ alkynyl substituted with 0–3 $R^{5b}$;

$C_3$–$C_{10}$ carbocycle substituted with 0–3 $R^{5c}$;

$C_6$–$C_{10}$ aryl substituted with 0–3 $R^{5c}$; and 5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from:

H, $C_1$–$C_6$ alkyl, $CF_3$, Cl, F, Br, I, =O, CN, $NO_2$, $NR^{15}R^{16}$;

$C_3$–$C_{10}$ carbocycle substituted with 0–3 $R^{5c}$;

$C_6$–$C_{10}$ aryl substituted with 0–3 $R^{5c}$; or 5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, and $C_1$–$C_4$ haloalkoxy, and $C_1$–$C_4$ haloalkyl-S—;

$R^6$ is H, methyl, or ethyl;

$R^7$, at each occurrence, is independently H or $C_1$–$C_4$ alkyl;

$R^{7a}$, at each occurrence, is independently H or $C_1$–$C_4$ alkyl;

$R^{7b}$ is H or $C_1$–$C_4$ alkyl;

Ring B is selected from:

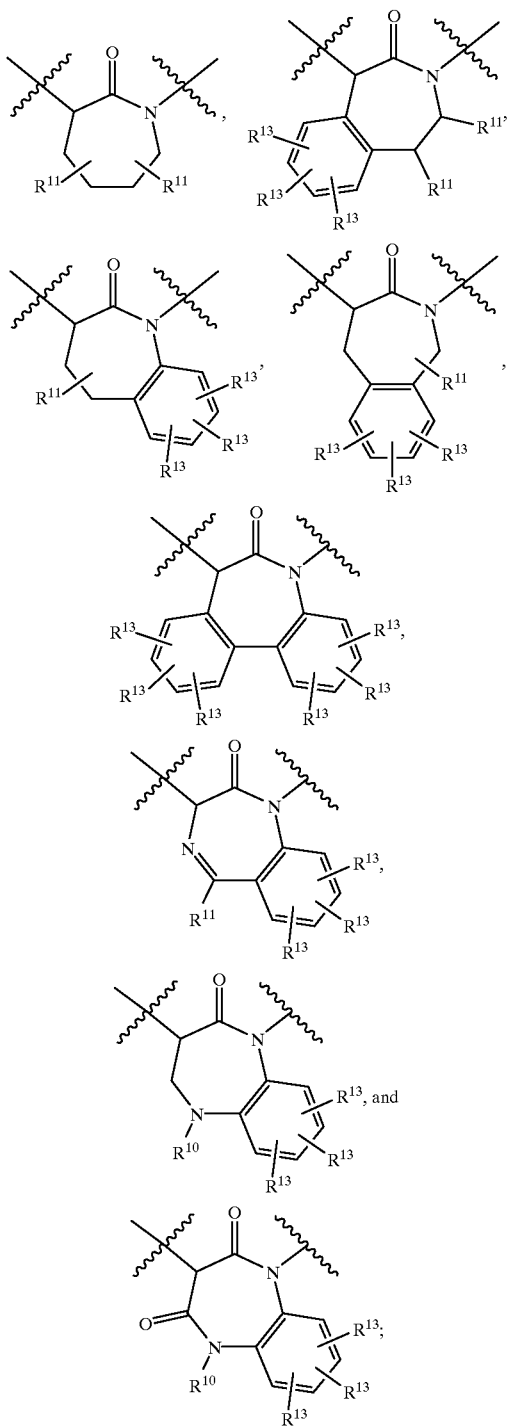

R$^{10}$ is H, C(=O)R$^{17}$, C(=O)OR$^{17}$, C(=O)NR$^{18}$R$^{19}$, S(=O)$_2$NR$^{18}$R$^{19}$, S(=O)$_2$R$^{17}$;
C$_1$–C$_6$ alkyl optionally substituted with 0–3 R$^{10a}$;
C$_6$–C$_{10}$ aryl substituted with 0–4 R$^{10b}$;
C$_3$–C$_{10}$ carbocycle substituted with 0–3 R$^{10b}$; or
5 to 10 membered heterocycle containing 1 to 4 heteroatoms selected from nitrogen, oxygen, and sulphur, wherein said 5 to 10 membered heterocycle is substituted with 0–3 R$^{10b}$;

R$^{10a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$, or aryl substituted with 0–4 R$^{10b}$;

R$^{10b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

R$^{11}$, at each occurrence, is independently selected from H, C$_1$–C$_4$ alkoxy, Cl, F, Br, I, =O, CN, NO$_2$, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
C$_1$–C$_6$ alkyl optionally substituted with 0–3 R$^{11a}$;
C$_6$–C$_{10}$ aryl substituted with 0–3 R$^{11b}$;
C$_3$–C$_{10}$ carbocycle substituted with 0–3 R$^{11b}$; or
5 to 10 membered heterocycle containing 1 to 4 heteroatoms selected from nitrogen, oxygen, and sulphur, wherein said 5 to 10 membered heterocycle is substituted with 0–3 R$^{11b}$;

R$^{11a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$;
phenyl substituted with 0–3 R$^{11b}$;
C$_3$–C$_6$ cycloalkyl substituted with 0–3 R$^{11b}$; and
5 to 6 membered heterocycle containing 1 to 3 heteroatoms selected from nitrogen, oxygen, and sulphur, wherein said 5 to 6 membered heterocycle is substituted with 0–3 R$^{11b}$;

R$^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

W is a bond or —(CH$_2$)$_p$—;
p is 1 or 2;
X is a bond;
phenyl substituted with 0–2 R$^{Xb}$;
C$_3$–C$_6$ carbocycle substituted with 0–2 R$^{Xb}$; or
5 to 6 membered heterocycle substituted with 0–2 R$^{Xb}$;

R$^{Xb}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_4$ alkyl, C$_1$–C$_3$ alkoxy, C$_1$–C$_3$ haloalkyl, C$_1$–C$_3$ haloalkoxy, and C$_1$–C$_3$ halothioalkoxy;

Y is a bond, —C(=O)—, —O—, —S—, —S(=O)—, —S(=O)$_2$—, —N(R$^{19}$)—, —C(=O)NR$^{19b}$—, NR$^{19b}$C(=O)—, —NR$^{19b}$S(=O)$_2$—, —S(=O)$_2$NR$^{19b}$—, —NR$^{19b}$S(=O)—, —S(=O)NR$^{19b}$—, —C(=O)O—, or —OC(=O)—;

Z is H;
C$_1$–C$_8$ alkyl substituted with 0–3 R$^{12a}$;
C$_2$–C$_6$ alkenyl substituted with 0–3 R$^{12a}$;
C$_2$–C$_6$ alkynyl substituted with 0–3 R$^{12a}$;
C$_6$–C$_{10}$ aryl substituted with 0–4 R$^{12b}$;
C$_3$–C$_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12a}$, at each occurrence, is independently selected from H, OH, Cl, F, Br, I, CN, NO$_2$, NR$^{15}$R$^{16}$, —C(=O)NR$^{15}$R$^{16}$, CF$_3$, acetyl, SCH$_3$, S(=O)CH$_3$, S(=O)$_2$CH$_3$,
C$_1$–C$_6$ alkyl, C$_1$–C$_4$ alkoxy, C$_1$–C$_4$ haloalkyl, C$_1$–C$_4$ haloalkoxy, C$_1$–C$_4$ haloalkyl-S—, $C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, OH, $C_1$–$C_6$ alkyl, benzyl, phenethyl, ($C_1$–$C_6$ alkyl)-C(=O)—, and ($C_{1-6}$ alkyl)-S(=O)$_2$—;

alternatively, $R^{15}$ and $R^{16}$, together with the nitrogen to which they are attached, may combine to form a 4–7 membered ring wherein said 4–7 membered ring optionally contains an additional heteroatom selected from O or NH;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, phenethyl;

$R^{19b}$, at each occurrence, is independently is H or $C_1$–$C_4$ alkyl;

$R^{21}$ is H, phenyl, benzyl, or $C_1$–$C_4$ alkyl; and $R^{22}$ is $C_1$–$C_4$ alkyl, $C_2$–$C_4$ alkenyl, or $C_3$–$C_4$ alkynyl.

[3] In another preferred embodiment, the present invention provides for a compound of Formula (Ib),

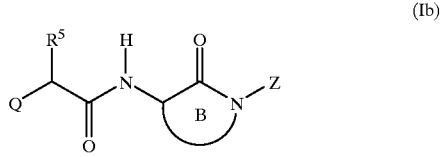

(Ib)

or a pharmaceutically acceptable salt or prodrug thereof, wherein:

Q is —(CHR$^7$)$_m$—R$^4$, —(CHR$^7$)$_n$—S—R$^4$, —(CHR$^7$)$_n$—O—R$^4$, or —(CHR$^7$)$_m$—N(R$^{7b}$)—R$^4$;

m is 1 or 2;

n is 0 or 1;

$R^4$ is H, $C_1$–$C_8$ alkyl substituted with 0–3 $R^{4a}$, $C_2$–$C_8$ alkenyl substituted with 0–3 $R^{4a}$, $C_2$–$C_8$ alkynyl substituted with 0–3 $R^{4a}$, $C_3$–$C_{10}$ carbocycle substituted with 0–3 $R^{4b}$, $C_6$–$C_{10}$ aryl substituted with 0–3 $R^{4b}$, or 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from is H, Cl, F, Br, I, CN, $NO_2$, $NR^{15}R^{16}$, $CF_3$, $OR^{14a}$, $C(=O)OR^{22}$, $SR^{22}$, $OR^{22}$, $NR^{21}R^{22}$, $S(=O)R^{22}$, $S(=O)_2R^{22}$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_3$–$C_{10}$ carbocycle substituted with 0–3 $R^{4b}$, $C_6$–$C_{10}$ aryl substituted with 0–3 $R^{4b}$, and 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ is H;

$C_1$–$C_6$ alkyl substituted with 0–3 $R^{5b}$;

$C_2$–$C_6$ alkenyl substituted with 0–3 $R^{5b}$;

$C_2$–$C_6$ alkynyl substituted with 0–3 $R^{5b}$;

$C_3$–$C_{10}$ carbocycle substituted with 0–3 $R^{5c}$;

$C_6$–$C_{10}$ aryl substituted with 0–3 $R^{5c}$; and 5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from: H, $C_1$–$C_6$ alkyl, $CF_3$, Cl, F, Br, I, =O, CN, $NO_2$, $R^{15}R^{16}$;

$C_3$–$C_{10}$ carbocycle substituted with 0–3 $R^{5c}$;

$C_6$–$C_{10}$ aryl substituted with 0–3 $R^{5c}$; or 5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy, and $C_1$–$C_4$ haloalkyl-S—;

$R^7$, at each occurrence, is independently H, methyl, or ethyl;

$R^{7b}$ is H, methyl, or ethyl;

Ring B is selected from:

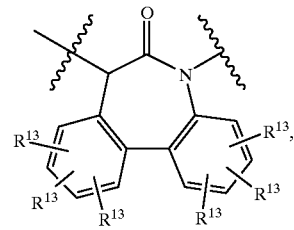

-continued

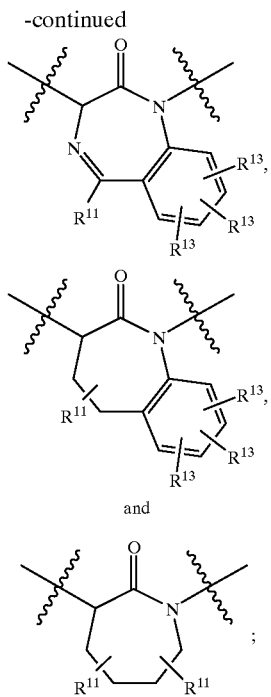

and

R$^{11}$, at each occurrence, is independently selected from H, C$_1$–C$_4$ alkoxy, Cl, F, Br, I, =O, CN, NO$_2$, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
C$_1$–C$_6$ alkyl optionally substituted with 0–3 R$^{11a}$;
C$_6$–C$_{10}$ aryl substituted with 0–3 R$^{11b}$;
C$_3$–C$_{10}$ carbocycle substituted with 0–3 R$^{11b}$; or
5 to 10 membered heterocycle containing 1 to 4 heteroatoms selected from nitrogen, oxygen, and sulphur, wherein said 5 to 10 membered heterocycle is substituted with 0–3 R$^{11b}$;

R$^{11a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$;
phenyl substituted with 0–3 R$^{11b}$;
C$_3$–C$_6$ cycloalkyl substituted with 0–3R$^{11b}$; and
5 to 6 membered heterocycle containing 1 to 3 heteroatoms selected from nitrogen, oxygen, and sulphur, wherein said 5 to 6 membered heterocycle is substituted with 0–3 R$^{11b}$;

R$^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

W is a bond;
X is a bond;
Y is a bond;
Z is H;
C$_1$–C$_8$ alkyl substituted with 0–3 R$^{12a}$;
C$_2$–C$_6$ alkenyl substituted with 0–3 R$^{12a}$;
C$_2$–C$_6$ alkynyl substituted with 0–3 R$^{12a}$;
C$_6$–C$_{10}$ aryl substituted with 0–4 R$^{12b}$;
C$_3$–C$_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12a}$, at each occurrence, is independently selected from H, OH, Cl, F, Br, I, CN, NO$_2$, NR$^{15}$R$^{16}$, —C(=O) NR$^{15}$R$^{16}$, CF$_3$, acetyl, SCH$_3$, S(=O)CH$_3$, S(=O)$_2$CH$_3$,
C$_1$–C$_6$ alkyl, C$_1$–C$_4$ alkoxy, C$_1$–C$_4$ haloalkyl, C$_1$–C$_4$ haloalkoxy, C$_1$–C$_4$ haloalkyl-S—,
C$_6$–C$_{10}$ aryl substituted with 0–4 R$^{12b}$;
C$_3$–C$_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

R$^{13}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, and CF$_3$;

R$^{14}$ is H, phenyl, benzyl, C$_1$–C$_6$ alkyl, C$_2$–C$_6$ alkoxyalkyl, or C$_3$–C$_6$ cycloalkyl;

R$^{14a}$ is H, phenyl, benzyl, or C$_1$–C$_4$ alkyl;

R$^{15}$, at each occurrence, is independently selected from H, C$_1$–C$_6$ alkyl, benzyl, phenethyl, (C$_1$–C$_6$ alkyl)-C (=O)—, and (C$_1$–C$_6$ alkyl)-S(=O)$_2$—;

R$^{16}$, at each occurrence, is independently selected from H, OH, C$_1$–C$_6$ alkyl, benzyl, phenethyl, (C$_1$–C$_6$ alkyl)-C (=O)—, and (C$_1$–C$_6$ alkyl)-S(=O)$_2$—;

alternatively, R$^{15}$ and R$^{16}$, together with the nitrogen to which they are attached, may combine to form a 4–7 membered ring wherein said 4–7 membered ring optionally contains an additional heteroatom selected from O or NH;

R$^{17}$ is H, C$_1$–C$_6$ alkyl, C$_2$–C$_6$ alkoxyalkyl, aryl substituted by 0–4 R$^{17a}$, or —CH$_2$-aryl substituted by 0–4 R$^{17a}$;

R$^{17a}$ is H, methyl, ethyl, propyl, butyl, methoxy, ethoxy, propoxy, butoxy, —OH, F, Cl, Br, I, CF$_3$, OCF$_3$, SCH$_3$, S(O)CH$_3$, SO$_2$CH$_3$, —NH$_2$, —N(CH$_3$)$_2$, or C$_1$–C$_4$ haloalkyl;

R$^{18}$ at each occurrence, is independently selected from H, C$_1$–C$_6$ alkyl, phenyl, benzyl, phenethyl, (C$_1$–C$_6$ alkyl)-C(=O)—, and (C$_{1-C6}$ alkyl)-S(=O)$_2$—;

R$^{19}$, at each occurrence, is independently selected from H, OH, methyl, ethyl, propyl, butyl, phenyl, benzyl, phenethyl;

R$^{21}$ is H, phenyl, benzyl, methyl, ethyl, propyl, or butyl; and

R$^{22}$ is methyl, ethyl, propyl, butyl, propenyl, butenyl, and propargyl.

[4] In another preferred embodiment, the present invention provides for a compound of Formula (I), or a pharmaceutically acceptable salt or prodrug thereof, wherein:
Q is —(CH$_2$)$_m$—R$^4$, —(CH$_2$)$_n$—S—R$^4$, —(CH$_2$)$_n$—O—R$^4$, or —(CH$_2$)$_m$—N (H)—R$^4$;
m is 1 or 2;
n is 0 or 1;
R$^4$ is C$_1$–C$_8$ alkyl substituted with 0–3 R$^{4a}$,
C$_2$–C$_8$ alkenyl substituted with 0–3 R$^{4a}$,
C$_2$–C$_8$ alkynyl substituted with 0–3 R$^{4a}$,
C$_3$–C$_{10}$ carbocycle substituted with 0–3 R$^{4b}$,
C$_6$–C$_{10}$ aryl substituted with 0–3 R$^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from is H, Cl, F, Br, I, CN, $NO_2$, $NR^{15}R^{16}$, $CF_3$, $C(=O)OR^{22}$, $SR^{22}$, $OR^{22}$, $OR^{14a}$, $NR^{21}R^{22}$, $S(=O)R^{22}$, $S(=O)_2R^{22}$, $C_1-C_6$ alkyl, $C_1-C_4$ alkoxy, $C_1-C_4$ haloalkyl, $C_1-C_4$ haloalkoxy, $C_1-C_4$ haloalkyl-S—, $C_3-C_{10}$ carbocycle substituted with 0–3 $R^{4b}$, $C_6-C_{10}$ aryl substituted with 0–3 $R^{4b}$, and 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, and $C_1-C_4$ haloalkyl-S—;

$R^5$ is H;
$C_1-C_6$ alkyl substituted with 0–3 $R^{5b}$;
$C_2-C_6$ alkenyl substituted with 0–3 $R^{5b}$;
$C_2-C_6$ alkynyl substituted with 0–3 $R^{5b}$;
$C_3-C_{10}$ carbocycle substituted with 0–3 $R^{5c}$;
$C_6-C_{10}$ aryl substituted with 0–3 $R^{5c}$; and
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from:
H, $C_1-C_6$ alkyl, $CF_3$, Cl, F, Br, I, =O, CN, $NO_2$, $R^{15}R^{16}$;
$C_3-C_{10}$ carbocycle substituted with 0–3 $R^{5c}$;
$C_6-C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, and $C_1-C_4$ haloalkoxy;

Ring B is selected from:

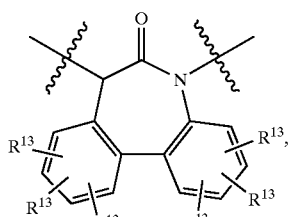

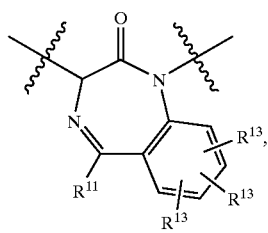

-continued

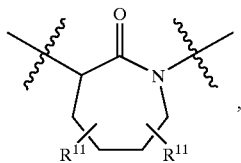
and

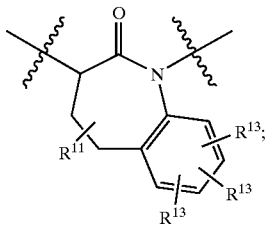

$R^{11}$, at each occurrence, is independently selected from H, =O, $NR^{18}R^{19}$, $CF_3$;
$C_1-C_4$ alkyl optionally substituted with 0–1 $R^{11a}$;
phenyl substituted with 0–3 $R^{11b}$;
$C_3-C_6$ carbocycle substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, $C_1-C_4$ alkyl, $OR^{14}$, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1-C_2$ haloalkyl, and $C_1-C_2$ haloalkoxy;

W is a bond;
X is a bond;
Y is a bond;
Z is H;
$C_1-C_8$ alkyl substituted with 0–3 $R^{12a}$;
$C_2-C_6$ alkenyl substituted with 0–3 $R^{12a}$; or
$C_2-C_6$ alkynyl substituted with 0–3 $R^{12a}$;

$R^{12a}$, at each occurrence, is independently selected from H, OH, Cl, F, Br, I, CN, $NO_2$, $NR^{15}R^{16}$, $—C(=O)NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, $C_1-C_4$ haloalkyl-S—, $C_6-C_{10}$ aryl substituted with 0–4 $R^{12b}$; $C_3-C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$; and wherein said 5 to 10 membered heterocycle is selected from pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, and $C_1-C_4$ haloalkyl-S—;

$R^{13}$, at each occurrence, is independently selected from H, OH, $C_1-C_6$ alkyl, $C_1-C_4$ alkoxy, Cl, F, Br, I, CN, $NO_2$, $NR^{15}R^{16}$, and $CF_3$;

$R^{14}$ is H, phenyl, benzyl, $C_1-C_6$ alkyl, $C_2-C_6$ alkoxyalkyl, or $C_3-C_6$ cycloalkyl;

$R^{14a}$ is H, phenyl, benzyl, or $C_1-C_4$ alkyl;

$R^{15}$, at each occurrence, is independently selected from H, $C_1-C_6$ alkyl, benzyl, phenethyl, $(C_1-C_4$ alkyl)-C$(=O)$—, and $(C_1-C_4$ alkyl)-S$(=O)_2$—;

$R^{16}$, at each occurrence, is independently selected from H, OH, $C_1-C_6$ alkyl, benzyl, phenethyl, $(C_1-C_4$ alkyl)-C$(=O)$—, and $(C_1-C_4$ alkyl)-S$(=O)_2$—; and alternatively, $R^{15}$ and $R^{16}$, together with the nitrogen to which they are attached, may combine to form a 4–6 membered ring wherein said 4–6 membered ring optionally contains an additional heteroatom selected from O or NH, wherein said 4–6 membered ring is selected from imidazolidinyl, oxazolidinyl, thiazolidinyl, piperazinyl, morpholinyl, and thiomorpholinyl;

$R^{18}$, at each occurrence, is independently selected from H, $C_1-C_6$ alkyl, phenyl, benzyl, phenethyl, $(C_1-C_6$ alkyl)-C$(=O)$—, and $(C_1-C_6$ alkyl)-S$(=O)_2$—;

$R^{19}$, at each occurrence, is independently selected from H, OH, methyl, ethyl, propyl, butyl, phenyl, benzyl, phenethyl;

$R^{21}$ is H, phenyl, benzyl, methyl, ethyl, propyl, or butyl; and $R^{22}$ is methyl, ethyl, propyl, butyl, propenyl, butenyl, and propargyl.

[5] In another preferred embodiment, the present invention provides for a compound of Formula (I), or a pharmaceutically acceptable salt or prodrug thereof, wherein:

Q is —$CH_2R^4$, —O—$R^4$, or —$CH_2$—NH—$R^4$;

$R^4$ is $C_1-C_6$ alkyl substituted with 0–3 $R^{4a}$,
$C_2-C_6$ alkenyl substituted with 0–3 $R^{4a}$,
$C_2-C_6$ alkynyl substituted with 0–3 $R^{4a}$,
$C_3-C_6$ carbocycle substituted with 0–3 $R^{4b}$, phenyl substituted with 0–3 $R^{4b}$, or
5 to 6 membered heterocycle containing 1 to 3 heteroatoms selected from nitrogen, oxygen, and sulphur, wherein said 5 to 6 membered heterocycle is substituted with 0–3 $R^{4b}$;

$R^{4a}$, at each occurrence, is independently selected from H, Cl, F, Br, I, CN, $NO_2$, $NR^{15}R^{16}$, $CF_3$, C$(=O)OR^{22}$, $SR^{22}$, $OR^{14a}$, $OR^{22}$, $NR^{21}R^{22}$, $S(=O)R^{22}$, $S(=O)_2R^{22}$, $C_1-C_6$ alkyl, $C_1-C_4$ alkoxy, $C_1-C_4$ haloalkyl, $C_1-C_4$ haloalkoxy, $C_1-C_4$ haloalkyl-S—,
$C_3-C_{10}$ carbocycle substituted with 0–3 $R^{4b}$,
$C_6-C_{10}$ aryl substituted with 0–3 $R^{4b}$, and
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1-C_6$ alkyl, $C_1-C_4$ alkoxy, $C_1-C_4$ haloalkyl, $C_1-C_4$ haloalkoxy, and $C_1-C_4$ haloalkyl-S—;

$R^5$ is H;

$C_1-C_6$ alkyl substituted with 0–3 $R^{5b}$;
$C_2-C_6$ alkenyl substituted with 0–3 $R^{5b}$; or
$C_2-C_6$ alkynyl substituted with 0–3 $R^{5b}$;

$R^{5b}$, at each occurrence, is independently selected from:
H, methyl, ethyl, propyl, butyl, $CF_3$, Cl, F, Br, I, =O;
$C_3-C_6$ carbocycle substituted with 0–3 $R^{5c}$;
phenyl substituted with 0–3 $R^{5c}$; or
5 to 6 membered heterocycle containing 1 to 3 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)$ $CH_3$, $S(=O)_2CH_3$,
$C_1-C_4$ alkyl, $C_1-C_3$ alkoxy, $C_1-C_2$ haloalkyl, and $C_1-C_2$ haloalkoxy;

Ring B is selected from:

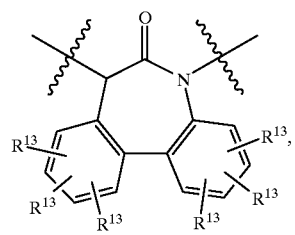

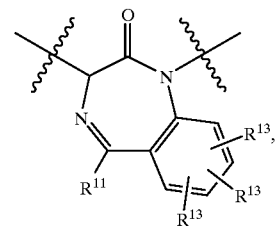

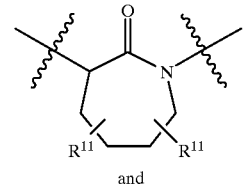

and

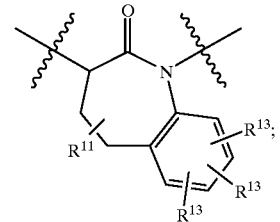

$R^{11}$, at each occurrence, is independently selected from H, =O, $NR^{18}R^{19}$, $CF_3$;
$C_1-C_4$ alkyl optionally substituted with 0–1 $R^{11a}$;
phenyl substituted with 0–3 $R^{11b}$;
$C_3-C_6$ carbocycle substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, phenoxy, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond;

X is a bond;

Y is a bond;

Z is H;

$C_1$–$C_4$ alkyl substituted with 0–3 $R^{12a}$;
$C_2$–$C_4$ alkenyl substituted with 0–3 $R^{12a}$; or
$C_2$–$C_4$ alkynyl substituted with 0–3 $R^{12a}$;

$R^{12a}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_4$ alkyl, or $C_2$–$C_4$ alkoxyalkyl;

$R^{14a}$ is H, phenyl, benzyl, or $C_1$–$C_4$ alkyl;

$R^{15}$, at each occurrence, is independently selected from H, $C_1$–$C_4$ alkyl, and benzyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl;

$R^{21}$ is H, phenyl, benzyl, methyl, ethyl, propyl, or butyl; and $R^{22}$ is methyl, ethyl, propyl, butyl, propenyl, butenyl, and propargyl.

[6] In another preferred embodiment, the present invention provides for a compound of Formula (I), or a pharmaceutically acceptable salt or prodrug thereof, wherein:

Q is —$CH_2R^4$, —O—$R^4$, or —$CH_2$—NH—$R^4$;

$R^4$ is $C_1$–$C_6$ alkyl substituted with 0–2 $R^{4a}$,
$C_2$–$C_6$ alkenyl substituted with 0–2 $R^{4a}$,
$C_2$–$C_6$ alkynyl substituted with 0–2 $R^{4a}$, or
$C_3$–$C_6$ cycloalkyl substituted with 0–3 $R^{4b}$;

$R^{4a}$, at each occurrence, is independently selected from is H, OH, F, Cl, Br, I, CN, $NR^{15}R^{16}$, $CF_3$, methyl, ethyl, propyl, methoxy, ethoxy, propoxy, $OCF_3$;

$C_3$–$C_6$ carbocycle substituted with 0–3 $R^{4b}$, phenyl substituted with 0–3 $R^{4b}$, or 5 to 6 membered heterocycle containing 1 to 3 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ is H;
$C_1$–$C_4$ alkyl substituted with 0–1 $R^{5b}$;
$C_2$–$C_4$ alkenyl substituted with 0–1 $R^{5b}$; or
$C_2$–$C_4$ alkynyl substituted with 0–1 $R^{5b}$;

$R^{5b}$, at each occurrence, is independently selected from:
H, methyl, ethyl, propyl, butyl, $CF_3$;
$C_3$–$C_6$ carbocycle substituted with 0–2 $R^{5c}$;
phenyl substituted with 0–3 $R^{5c}$; and
5 to 6 membered heterocycle containing 1 to 3 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, $C_1$–$C_4$ alkyl, $C_1$–$C_3$ alkoxy, $C_1$–$C_2$ haloalkyl, and $C_1$–$C_2$ haloalkoxy;

Ring B is selected from:

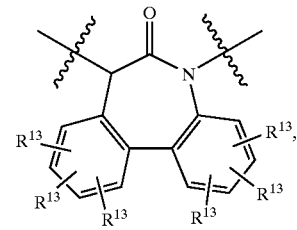

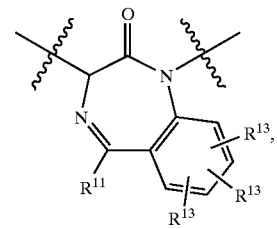

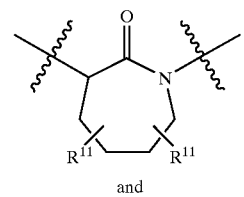

and

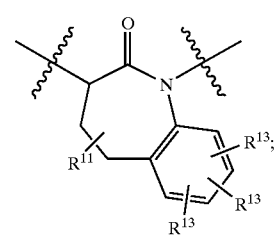

$R^{11}$, at each occurrence, is independently selected from H, =O, $NR^{18}R^{19}$;
$C_1$–$C_4$ alkyl optionally substituted with 0-1 $R^{11a}$;
phenyl substituted with 0–3 $R^{11b}$;
5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, methyl, ethyl, propyl, methoxy, ethoxy, propoxy, phenoxy, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond;

X is a bond;

Y is a bond;

Z is H;

$C_1$–$C_4$ alkyl substituted with 0–1 $R^{12a}$;
$C_2$–$C_4$ alkenyl substituted with 0–1 $R^{12a}$; or
$C_2$–$C_4$ alkynyl substituted with 0–1 $R^{12a}$;

$R^{12a}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl; and $R^{16}$, at each occurrence, is independently selected from H, OH, methyl, ethyl, propyl, butyl, benzyl, and phenethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

[7] In another preferred embodiment, the present invention provides for a compound of Formula (I), or a pharmaceutically acceptable salt or prodrug thereof, wherein:

Ring B is selected from:

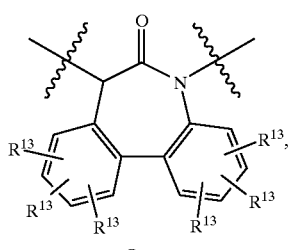

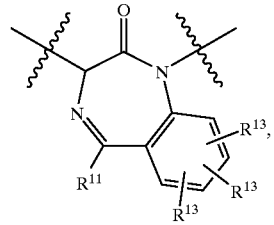

-continued $R^5$ is —$CH_3$, —$CH_2CH_3$, —$CH_2CH_2CH_3$, —$CH_2CH(CH_3)_2$, —$CH_2CH_2CH_2CH_3$, —$CH_2CH_2CH_2CH_2CH_3$, —$CH_2CH_2CH(CH_3)_2$, —$CH_2CH_2CH_2CH_2CH_3$, —$CH_2CH_2CH_2CH(CH_3)_2$, —$CH_2CH_2CH_2CH_2CH(CH_3)_2$, —$CH_2NH_2$, —$CH_2N(CH_3)_2$, —$CH_2N(CH_2CH_3)_2$, —$CH_2CH_2NH_2$, —$CH_2CH_2N(CH_3)_2$, —$CH_2CH_2N(CH_2CH_3)_2$, —$CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, or —$CH_2CH_2$-cyclohexyl;

Q is —$CH_3$, —$CH_2CH_3$, —$CH_2CH_2CH_3$, —$CH_2CH(CH_3)_2$, —$CH_2CH_2CH_2CH_3$, —$CH_2CH_2CH_2CH_2CH_3$, —$CH_2CH_2CH(CH_3)_2$, —$CH_2CH_2CH_2CH_2CH_3$, —$CH_2CH_2CH_2CH(CH_3)_2$, —$CH_2CH_2CH_2CH_2CH_2CH_3$, —$CH_2CH_2CH_2CH_2CH(CH_3)_2$, —$CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, —$CH_2CH_2$-cyclohexyl, —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH_2CH_2CH_2CH_2CH_3$, —$OCH_2CH_2CH_2CH_2CH_3$, —$OCH_2CH_2CH_2CH(CH_3)_2$, —$OCH_2CH_2CH_2CH_2CH(CH_3)_2$, —$OCH_2$-cyclopropyl, —$OCH_2$-cyclobutyl, —$OCH_2$-cyclopentyl, —$OCH_2$-cyclohexyl, —$OCH_2CH_2$-cyclopropyl, —$OCH_2CH_2$-cyclobutyl, —$OCH_2CH_2$-cyclopentyl, —$OCH_2CH_2$-cyclohexyl, —$CH_2OCH_2CH_3$, —$CH_2OCH_2CH_2CH_3$, —$CH_2$—$OCH(CH_3)_2$, —$CH_2OCH_2CH_2CH_2CH_3$, —$CH_2OCH_2CH(CH_3)_2$, —$CH_2OCH_2CH_2CH_2CH_2CH_3$, —$CH_2OCH_2CH_2CH(CH_3)_2$, —$CH_2OCH_2CH_2CH_2CH(CH_3)_2$, —$CH_2O$-cyclopropyl, —$CH_2O$-cyclobutyl, —$CH_2O$-cyclopentyl, —$CH_2O$-cyclohexyl, —$CH_2OCH_2$-cyclopropyl, —$CH_2OCH_2$-cyclobutyl, —$CH_2OCH_2$-cyclopentyl, —$CH_2OCH_2$-cyclohexyl; —$CH_2(NH)CH_3$, —$CH_2(NH)CH_2CH_3$, —$CH_2(NH)CH_2CH_2CH_3$, —$CH_2$—(NH)$CH(CH_3)_2$, —$CH_2(NH)CH_2CH_2CH_2CH_3$, —$CH_2(NH)CH_2CH(CH_3)_2$, —$CH_2(NH)CH_2CH_2CH_2CH_2CH_3$, —$CH_2(NH)CH_2CH_2CH(CH_3)_2$, —$CH_2(NH)CH_2CH_2CH_2CH(CH_3)_2$, —$CH_2(NH)$-cyclopropyl, —$CH_2(NH)$-cyclobutyl, —$CH_2(NH)$-cyclopentyl, —$CH_2(NH)$-cyclohexyl, —$CH_2(NH)CH_2$-cyclopropyl, —$CH_2(NH)CH_2$-cyclobutyl, —$CH_2(NH)CH_2$-cyclopentyl, or —$CH_2(NH)CH_2$-cyclohexyl;

W is a bond;
X is a bond;
Y is a bond;
Z is methyl, ethyl, i-propyl, n-propyl, n-butyl, i-butyl, s-butyl, t-butyl, or allyl;
$R^{11}$, at each occurrence, is independently selected from H, =O, methyl, ethyl, phenyl, benzyl, phenethyl, 4-F-phenyl, (4-F-phenyl)$CH_2$—, (4-F-phenyl)$CH_2CH_2$—, 3-F-phenyl, (3-F-phenyl)$CH_2$—, (3-F-phenyl)$CH_2CH_2$—, 2-F-phenyl, (2-F-phenyl)$CH_2$—, (2-F-phenyl)$CH_2CH_2$—, 4-Cl-phenyl, (4-Cl-phenyl)$CH_2$—, (4-Cl-phenyl)$CH_2CH_2$—, 3-Cl-phenyl, (3-Cl-phenyl)$CH_2$—, (3-Cl-phenyl)$CH_2CH_2$—, 4-$CH_3$-phenyl, (4-$CH_3$-phenyl)$CH_2$—, (4-$CH_3$-phenyl)$CH_2CH_2$—, 3-$CH_3$-phenyl, (3-$CH_3$-phenyl)$CH_2$—, (3-$CH_3$-phenyl)$CH_2CH_2$—, 4-$CF_3$-phenyl, (4-$CF_3$-phenyl)$CH_2$—, (4-$CF_3$-phenyl)$CH_2CH_2$—, pyrid-2-yl, 4-F-pyrid-2-yl, 4-Cl-pyrid-2-yl, 4-$CH_3$-pyrid-2-yl, 4-$CF_3$-pyrid-2-yl, pyrid-3-yl, 4-F-pyrid-3-yl, 4-Cl-pyrid-3-yl, 4-$CH_3$-pyrid-3-yl, 4-$CF_3$-pyrid-3-yl, or pyrid-4-yl; and
$R^{13}$, at each occurrence, is independently selected from H, F, Cl, OH, —$CH_3$, —$CH_2CH_3$, —$OCH_3$, or —$CF_3$.

[8] In another preferred embodiment, the present invention provides for a compound of Formula (I), or a pharmaceutically acceptable salt or prodrug thereof, wherein:
Q is —$(CH_2)_m$—$R^4$, —$(CH_2)_n$—S—$R^4$, —$(CH_2)_n$—O—$R^4$, or —$(CH_2)_m$—N(H)—$R^4$;
m is 1 or 2;
n is 0 or 1;
$R^4$ is $C_1$–$C_8$ alkyl substituted with 0–3 $R^{4a}$,
    $C_2$–$C_8$ alkenyl substituted with 0–3 $R^{4a}$,
    $C_2$–$C_8$ alkynyl substituted with 0–3 $R^{4a}$,
    $C_3$–$C_{10}$ carbocycle substituted with 0–3 $R^{4b}$,
    $C_6$–$C_{10}$ aryl substituted with 0–3 $R^{4b}$, or
    5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4a}$, at each occurrence, is independently selected from is H, Cl, F, Br, I, CN, $NO_2$, $NR^{15}R^{16}$, $CF_3$, C(=O)$OR^{22}$, $SR^{22}$, $OR^{22}$, $OR^{14a}$, $NR^{21}R^{22}$, S(=O)$R^{22}$, S(=O)$_2R^{22}$,
    $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—,
    $C_3$–$C_{10}$ carbocycle substituted with 0–3 $R^{4b}$,
    $C_6$–$C_{10}$ aryl substituted with 0–3 $R^{4b}$, and
    5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$,
    $C_1$–$C_6$ alkyl, $C_1$–$C_4$ alkoxy, $C_1$–$C_4$ haloalkyl,
    $C_1$–$C_4$ haloalkoxy, and $C_1$–$C_4$ haloalkyl-S—;
$R^5$ is H;
    $C_1$–$C_6$ alkyl substituted with 0–3 $R^{5b}$;
    $C_2$–$C_6$ alkenyl substituted with 0–3 $R^{5b}$;
    $C_2$–$C_6$ alkynyl substituted with 0–3 $R^{5b}$;
    $C_3$–$C_{10}$ carbocycle substituted with 0–3 $R^{5c}$;
    $C_6$–$C_{10}$ aryl substituted with 0–3 $R^{5c}$; and
    5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5b}$, at each occurrence, is independently selected from: H, $C_1$–$C_6$ alkyl, $CF_3$, Cl, F, Br, I, =O, CN, $NO_2$, $NR^{15}R^{16}$;
    $C_3$–$C_{10}$ carbocycle substituted with 0–3 $R^{5c}$;
    $C_6$–$C_{10}$ aryl substituted with 0–3 $R^{5c}$; or
    5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$,
    $C_1$–$C_6$ alkyl, $C_1$–$C_4$ alkoxy, $C_1$–$C_4$ haloalkyl, and $C_1$–$C_4$ haloalkoxy;
Ring B is selected from:

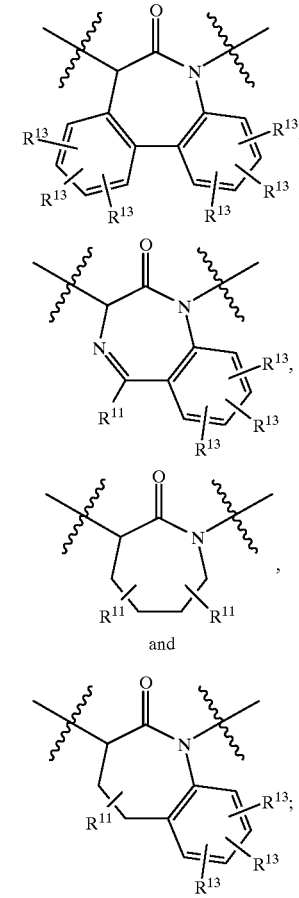

and

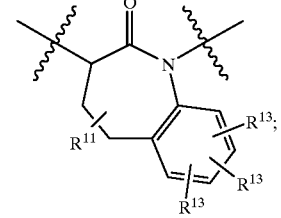

$R^{11}$, at each occurrence, is independently selected from H, =O, $NR^{18}R^{19}$, $CF_3$;
    $C_1$–$C_4$ alkyl optionally substituted with 0–3 $R^{11a}$;
    phenyl substituted with 0–3 $R^{11b}$;
    $C_3$–$C_6$ carbocycle substituted with 0–3 $R^{11b}$; or
    5 to 6 membered heterocycle containing 1 to 3 heteroatoms selected from nitrogen, oxygen, and sulphur, wherein said 5 to 6 membered heterocycle is substituted with 0–3 $R^{11b}$; and wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{11a}$, at each occurrence, is independently selected from H, $C_1$–$C_4$ alkyl, $OR^{14}$, Cl, F, =O, CN, $NO_2$, $NR^{15}R^{16}$, $CF_3$, or phenyl substituted with 0–3 $R^{11b}$;
$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_4$ haloalkoxy;

W is a bond, —$CH_2$—, —$CH_2CH_2$—;

X is a bond;
  phenyl substituted with 0–2 $R^{Xb}$;
  $C_3$–$C_6$ cycloalkyl substituted with 0–2 $R^{Xb}$; or
  5 to 6 membered heterocycle substituted with 0–2 $R^{Xb}$;

$R^{Xb}$, at each occurrence, is independently selected from H, OH, Cl, F, $NR^{15}R^{16}$, $CF_3$, acetyl, $SCH_3$, S(=O)$CH_3$, S(=O)$_2CH_3$, $C_1$–$C_4$ alkyl, $C_1$–$C_3$ alkoxy, $C_1$–$C_2$ haloalkyl, and $C_1$–$C_2$ haloalkoxy;

Y is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$, —S(=O)$_2$ $NR^{19b}$—, —$NR^{19b}$S(=O)—, —S(=O)$NR^{19b}$—, —C(=O)O—, or —OC(=O)—;

Z is $C_1$–$C_3$ alkyl substituted with 1–2 $R^{12a}$;
  $C_6$–$C_{10}$ aryl substituted with 0–4 $R^{12b}$;
  $C_3$–$C_{10}$ carbocycle substituted with 0–3 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from $C_6$–$C_{10}$ aryl substituted with 0–4 $R^{12b}$;
  $C_3$–$C_{10}$ carbocycle substituted with 0–4 $R^{12b}$; and
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy,
  $C_1$–$C_4$ haloalkyl, $C_1$–$C_4$ haloalkoxy, and
  $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_4$ alkyl)-C(=O)—, and ($C_{1-C4}$ alkyl)-S(=O)$_2$—;

$R^{16}$, at each occurrence, is independently selected from H, OH, $C_1$–$C_6$ alkyl, benzyl, phenethyl, ($C_{1-C4}$ alkyl)-C(=O)—, and ($C_1$–$C_4$ alkyl)-S(=O)$_2$—; and
alternatively, $R^{15}$ and $R^{16}$, together with the nitrogen to which they are attached, may combine to form a 4–6 membered ring wherein said 4–6 membered ring optionally contains an additional heteroatom selected from O or NH, wherein said 4–6 membered ring is selected from imidazolidinyl, oxazolidinyl, thiazolidinyl, piperazinyl, morpholinyl, and thiomorpholinyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, and phenethyl;

$R^{21}$ is H, phenyl, benzyl, methyl, ethyl, propyl, or butyl; and $R^{22}$ is methyl, ethyl, propyl, butyl, propenyl, butenyl, and propargyl.

[9] In another preferred embodiment, the present invention provides for a compound of Formula (I), or a pharmaceutically acceptable salt or prodrug thereof, wherein:

Q is —$CH_2R^4$, —O—$R^4$, or —$CH_2$—NH—$R^4$;

$R^4$ is $C_1$–$C_6$ alkyl substituted with 0–3 $R^{4a}$;
  $C_2$–$C_6$ alkenyl substituted with 0–3 $R^{4a}$;
  $C_2$–$C_6$ alkynyl substituted with 0–3 $R^{4a}$;
  $C_3$–$C_6$ carbocycle substituted with 0–3 $R^{4b}$; phenyl substituted with 0–3 $R^{4b}$, or
  5 to 6 membered heterocycle containing 1 to 3 heteroatoms selected from nitrogen, oxygen, and sulphur, wherein said 5 to 6 membered heterocycle is substituted with 0–3 $R^{4b}$;

$R^{4a}$, at each occurrence, is independently selected from H, Cl, F, Br, I, CN, $NO_2$, $NR^{15}R^{16}$, $CF_3$, C(=O)$OR^{22}$, $SR^{22}$, $OR^{14a}$, $OR^{22}$, $NR^{21}R^{22}$, S(=O)$R^{22}$, S(=O)$_2R^{22}$,
  $C_1$–$C_6$ alkyl, $C_1$–$C_4$ alkoxy, $C_1$–$C_4$ haloalkyl,
  $C_1$–$C_4$ haloalkoxy, $C_1$–$C_4$ haloalkyl-S—,
  $C_3$–$C_{10}$ carbocycle substituted with 0–3 $R^{4b}$,
  $C_6$–$C_{10}$ aryl substituted with 0–3 $R^{4b}$, and
  5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ is H;
  $C_1$–$C_6$ alkyl substituted with 0–3 $R^{5b}$;
  $C_2$–$C_6$ alkenyl substituted with 0–3 $R^{5b}$; or
  $C_2$–$C_6$ alkynyl substituted with 0–3 $R^{5b}$;

$R^{5b}$, at each occurrence, is independently selected from:
  H, methyl, ethyl, propyl, butyl, $CF_3$, Cl, F, Br, I, =O;
  $C_3$–$C_6$ carbocycle substituted with 0–3 $R^{5c}$;
  phenyl substituted with 0–3 $R^{5c}$; or
  5 to 6 membered heterocycle containing 1 to 3 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$,
  $C_1$–$C_4$ alkyl, $C_1$–$C_3$ alkoxy, $C_1$–$C_2$ haloalkyl, and
  $C_1$–$C_2$ haloalkoxy;

Ring B is selected from:

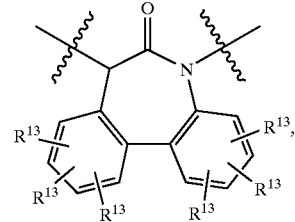

-continued

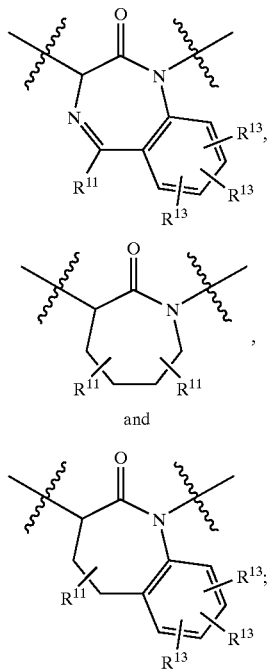

and

R¹¹, at each occurrence, is independently selected from H, =O, NR¹⁸R¹⁹, CF₃;
  C₁–C₄ alkyl optionally substituted with 0–3 R¹¹ᵃ;
  phenyl substituted with 0–3 R¹¹ᵇ;
  C₃–C₆ carbocycle substituted with 0–3 R¹¹ᵇ; or
  5 to 6 membered heterocycle containing 1 to 3 heteroatoms selected from nitrogen, oxygen, and sulphur, wherein said 5 to 6 membered heterocycle is substituted with 0–3 R¹¹ᵇ; and wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
R¹¹ᵃ, at each occurrence, is independently selected from H, methyl, ethyl, propyl, butyl, methoxy, ethoxy, propoxy, phenoxy, Cl, F, =O, NR¹⁵R¹⁶, CF₃, or phenyl substituted with 0–3 R¹¹ᵇ;
R¹¹ᵇ, at each occurrence, is independently selected from H, OH, Cl, F, NR¹⁵R¹⁶, CF₃, methyl, ethyl, propyl, butyl, methoxy, ethoxy, propoxy, C₁–C₂ haloalkyl, and C₁–C₄ haloalkoxy;
W is a bond, —CH₂—, —CH₂CH₂—;
X is a bond;
  phenyl substituted with 0–1 R^{Xb};
  C₃–C₆ cycloalkyl substituted with 0–1 R^{Xb}; or
  5 to 6 membered heterocycle substituted with 0–1 R^{Xb};
R^{Xb} is selected from H, OH, Cl, F, NR¹⁵R¹⁶, CF₃, acetyl, SCH₃, S(=O)CH₃, S(=O)₂CH₃, methyl, ethyl, propyl, methoxy, ethoxy, propoxy, and —OCF₃;
Y is a bond, —C(=O)—, —O—, —S—, —S(=O)—, —S(=O)₂—, —NH—, —N(CH₃)—, or —N(CH₂CH₃)—;
Z is C₁–C₂ alkyl substituted with 1–2 R¹²ᵃ;
  C₆–C₁₀ aryl substituted with 0–4 R¹²ᵇ;
  C₃–C₁₀ carbocycle substituted with 0–3 R¹²ᵇ; or
  5 to 10 membered heterocycle containing 1 to 4 heteroatoms selected from nitrogen, oxygen, and sulphur, wherein said 5 to 10 membered heterocycle is substituted with 0–3 R¹²ᵇ;

R¹²ᵃ, at each occurrence, is independently selected from C₆–C₁₀ aryl substituted with 0–4 R¹²ᵇ;
  C₃–C₁₀ carbocycle substituted with 0–4 R¹²ᵇ; and
  5 to 10 membered heterocycle containing 1 to 4 heteroatoms selected from nitrogen, oxygen, and sulphur, wherein said 5 to 10 membered heterocycle is substituted with 0–3 R¹²ᵇ;
R¹²ᵇ, at each occurrence, is independently selected from H, OH, Cl, F, Br, I, CN, NO₂, NR¹⁵R¹⁶, CF₃, acetyl, SCH₃, S(=O)CH₃, S(=O)₂CH₃, C₁–C₆ alkyl, C₁–C₄ alkoxy,
  C₁–C₄ haloalkyl, C₁–C₄ haloalkoxy, and
  C₁–C₄ haloalkyl-S—;
R¹³, at each occurrence, is independently selected from H, OH, C₁–C₆ alkyl, C₁–C₄ alkoxy, Cl, F, Br, I, CN, NO₂, NR¹⁵R¹⁶, and CF₃;
R¹⁴ is H, phenyl, benzyl, C₁–C₄ alkyl, or C₂–C₄ alkoxyalkyl;
R¹⁴ᵃ is H, phenyl, benzyl, or C₁–C₄ alkyl;
R¹⁵, at each occurrence, is independently selected from H, C₁–C₄ alkyl, and benzyl;
R¹⁶, at each occurrence, is independently selected from H, OH, methyl, ethyl, propyl, butyl, benzyl, phenethyl, methyl-C(=O)—, ethyl-C(=O)—, methyl-S(=O)₂—, and ethyl-S(=O)₂—;
R¹⁸, at each occurrence, is independently selected from H, methyl, ethyl, propyl, butyl, phenyl, benzyl, and phenethyl;
R¹⁹, at each occurrence, is independently selected from H, methyl, ethyl, propyl, and butyl; and
R²¹ is H, phenyl, benzyl, methyl, ethyl, propyl, or butyl; and
R²² is methyl, ethyl, propyl, butyl, propenyl, butenyl, and propargyl.

[10] In another preferred embodiment, the present invention provides for a compound of Formula (I), or a pharmaceutically acceptable salt or prodrug thereof, wherein:
Q is —CH₂R⁴, —O—R⁴, or —CH₂—NH—R⁴;
R⁴ is C₁–C₆ alkyl substituted with 0–2 R⁴ᵃ,
  C₂–C₆ alkenyl substituted with 0–2 R⁴ᵃ,
  C₂–C₆ alkynyl substituted with 0–2 R⁴ᵃ, or
  C₃–C₆ cycloalkyl substituted with 0–3 R⁴ᵇ;
R⁴ᵃ, at each occurrence, is independently selected from is H, OH, F, Cl, Br, I, CN, NR¹⁵NR¹⁶, CF₃, methyl, ethyl, propyl, butyl, methoxy, ethoxy, propoxy, OCF₃; C₃–C₆ carbocycle substituted with 0–3 R⁴ᵇ, phenyl substituted with 0–3 R⁴ᵇ, or 5 to 6 membered heterocycle containing 1 to 3 heteroatoms selected from nitrogen, oxygen, and sulphur, wherein said 5 to 6 membered heterocycle is substituted with 0–3 R⁴ᵇ; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
R⁴ᵇ, at each occurrence, is independently selected from H, OH, Cl, F, Br, I, CN, NO₂, NR¹⁵R¹⁶, CF₃, acetyl, SCH₃, S(=O)CH₃, S(=O)₂CH₃, C₁–C₆ alkyl, C₁–C₄ alkoxy, C₁–C₄ haloalkyl, C₁–C₄ haloalkoxy, and C₁–C₄ haloalkyl-S—;
R⁵ is H;
  C₁–C₄ alkyl substituted with 0–1 R⁵ᵇ;
  C₂–C₄ alkenyl substituted with 0–1 R⁵ᵇ; or
  C₂–C₄ alkynyl substituted with 0–1 R⁵ᵇ;
R⁵ᵇ, at each occurrence, is independently selected from: H, methyl, ethyl, propyl, butyl, CF₃; C₃–C₆ carbocycle substituted with 0–2 $R^{5c}$; phenyl substituted with 0–3 $R^{5c}$; and 5 to 6 membered heterocycle containing 1 to 3 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, $C_1$–$C_4$ alkyl, $C_1$–$C_3$ alkoxy, $C_1$–$C_2$ haloalkyl, and $C_1$–$C_2$ haloalkoxy;

Ring B is selected from:

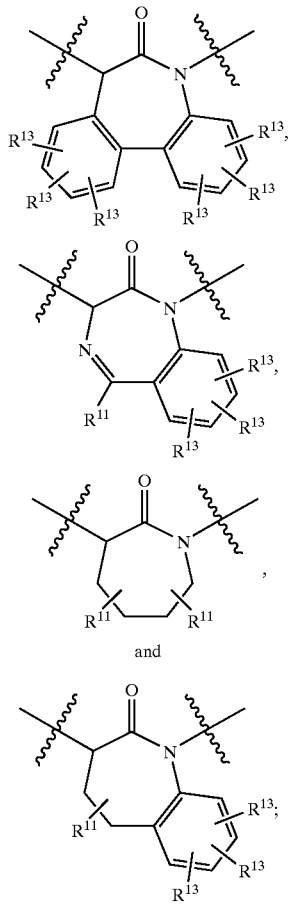

and $R^{11}$, at each occurrence, is independently selected from H, =O, $NR^{18}R^{19}$;

$C_1$–$C_4$ alkyl optionally substituted with 0–3 $R^{11a}$;

phenyl substituted with 0–3 $R^{11b}$;

$C_3$–$C_6$ carbocycle substituted with 0–3 $R^{11b}$; or 5 to 6 membered heterocycle containing 1 to 3 heteroatoms selected from nitrogen, oxygen, and sulphur, wherein said 5 to 6 membered heterocycle is substituted with 0–3 $R^{11b}$; and wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, phenoxy, Cl, F, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond or —$CH_2$—;

X is a bond;

phenyl substituted with 0–1 $R^{Xb}$;

$C_3$–$C_6$ cycloalkyl substituted with 0–1 $R^{Xb}$; or 5 to 6 membered heterocycle substituted with 0–1 $R^{Xb}$;

$R^{Xb}$ is selected from H, OH, Cl, F, $NR^{15}R^{16}$, $CF_3$, acetyl, methyl, ethyl, methoxy, ethoxy, and —$OCF_3$;

Y is a bond, —C(=O)—, —O—, —S—, —S(=O)—, —S(=O)$_2$—, —NH—, —N($CH_3$)—, or —N($CH_2CH_3$)—;

Z is $C_1$–$C_2$ alkyl substituted with 1–2 $R^{12a}$; $C_6$–$C_{10}$ aryl substituted with 0–4 $R^{12b}$; $C_3$–$C_{10}$ carbocycle substituted with 0–3 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from $C_6$–$C_{10}$ aryl substituted with 0–4 $R^{12b}$; $C_3$–$C_{10}$ carbocycle substituted with 0–4 $R^{12b}$; and 5 to 10 membered heterocycle containing 1 to 4 heteroatoms selected from nitrogen, oxygen, and sulphur, wherein said 5 to 10 membered heterocycle is substituted with 0–3 $R^{12b}$; and wherein said 5 to 10 membered heterocycle is selected from pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl;

$R^{12b}$, at each occurrence, is independently selected from H, OH, Cl, F, $NR^{15}R^{16}$, $CF_3$, acetyl, $SCH_3$, S(=O)$CH_3$, S(=O)$_2CH_3$, methyl, ethyl, propyl, butyl, methoxy, ethoxy, propoxy, and —$OCF_3$;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl; and $R^{16}$, at each occurrence, is independently selected from H, OH, methyl, ethyl, propyl, butyl, benzyl, and phenethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

[11] In another preferred embodiment, the present invention provides for a compound of Formula (I), or a pharmaceutically acceptable salt or prodrug thereof, wherein:

Ring B is selected from:

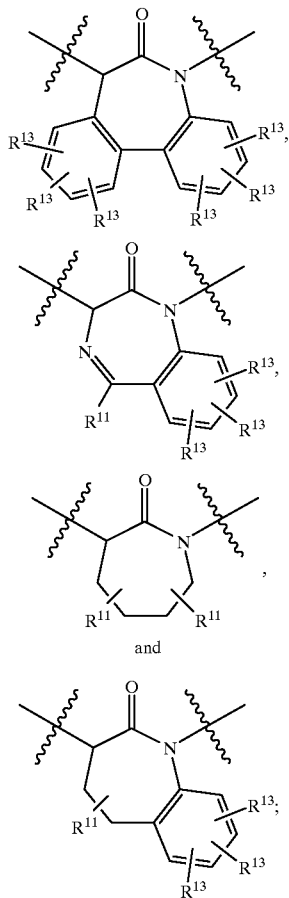

and

R⁵ is —CH₃, —CH₂CH₃, —CH₂CH₂CH₃, —CH₂CH(CH₃)₂, —CH₂CH₂CH₂CH₃, —CH₂CH₂CH₂CH₂CH₃, —CH₂CH₂CH(CH₃)₂, —CH₂CH₂CH₂CH₂CH₂CH₃, —CH₂CH₂CH₂CH(CH₃)₂, —CH₂CH₂CH₂CH₂CH(CH₃)₂, —CH₂NH₂, —CH₂N(CH₃)₂, —CH₂N(CH₂CH₃)₂, —CH₂CH₂NH₂, —CH₂CH₂N(CH₃)₂, —CH₂CH₂N(CH₂CH₃)₂, —CH₂-cyclopropyl, —CH₂-cyclobutyl, —CH₂-cyclopentyl, —CH₂-cyclohexyl, —CH₂CH₂-cyclopropyl, —CH₂CH₂-cyclobutyl, —CH₂CH₂-cyclopentyl, or —CH₂CH₂-cyclohexyl;

Q is —CH₃, —CH₂CH₃, —CH₂CH₂CH₃, —CH₂CH(CH₃)₂, —CH₂CH₂CH₂CH₃, —CH₂CH₂CH₂CH₂CH₃, —CH₂CH₂CH(CH₃)₂, —CH₂CH₂CH₂CH₂CH₂CH₃, —CH₂CH₂CH₂CH(CH₃)₂, —CH₂CH₂CH₂CH₂CH₂CH₂CH₃, —CH₂CH₂CH₂CH₂CH(CH₃)₂, —CH₂-cyclopropyl, —CH₂-cyclobutyl, —CH₂-cyclopentyl, —CH₂-cyclohexyl, —CH₂CH₂-cyclopropyl, —CH₂CH₂-cyclobutyl, —CH₂CH₂-cyclopentyl, —CH₂CH₂-cyclohexyl, —OCH₃, —OCH₂CH₃, —OCH₂CH₂CH₃, —OCH(CH₃)₂, —OCH₂CH₂CH₂CH₃, —OCH₂CH(CH₃)₂, —OCH₂CH₂CH(CH₃)₂, —OCH₂CH₂CH₂CH₂CH₃, —OCH₂CH₂CH₂CH₂CH₂CH₃, —OCH₂CH₂CH₂CH(CH₃)₂, —OCH₂CH₂CH₂CH₂CH(CH₃)₂, —OCH₂-cyclopropyl, —OCH₂-cyclobutyl, —OCH₂-cyclopentyl, —OCH₂-cyclohexyl, —OCH₂CH₂-cyclopropyl, —OCH₂CH₂-cyclobutyl, —OCH₂CH₂-cyclopentyl, —OCH₂CH₂-cyclohexyl, —CH₂OCH₂CH₃, —CH₂OCH₂CH₂CH₃, —CH₂—OCH(CH₃)₂, —CH₂OCH₂CH₂CH₂CH₃, —CH₂OCH₂CH(CH₃)₂, —CH₂OCH₂CH₂CH₂CH₂CH₃, —CH₂OCH₂CH(CH₃)₂, —CH₂OCH₂CH₂CH(CH₃)₂, —CH₂O-cyclopropyl, —CH₂O-cyclobutyl, —CH₂O-cyclopentyl, —CH₂O-cyclohexyl, —CH₂OCH₂-cyclopropyl, —CH₂OCH₂-cyclobutyl, —CH₂OCH₂-cyclopentyl, —CH₂OCH₂-cyclohexyl; —CH₂(NH)CH₃, —CH₂(NH)CH₂CH₃, —CH₂(NH)CH₂CH₂CH₃, —CH₂—(NH)CH(CH₃)₂, —CH₂(NH)CH₂CH₂CH₂CH₃, —CH₂(NH)CH₂CH(CH₃)₂, —CH₂(NH)CH₂CH₂CH₂CH₂CH₃, —CH₂(NH)CH₂CH₂CH(CH₃)₂, —CH₂(NH)CH₂CH₂CH₂CH(CH₃)₂, —CH₂(NH)-cyclopropyl, —CH₂(NH)-cyclobutyl, —CH₂(NH)-cyclopentyl, —CH₂(NH)-cyclohexyl, —CH₂(NH)CH₂-cyclopropyl, —CH₂(NH)CH₂-cyclobutyl, —CH₂(NH)CH₂-cyclopentyl, or —CH₂(NH)CH₂-cyclohexyl;

W is a bond or —CH₂—;

X is a bond;

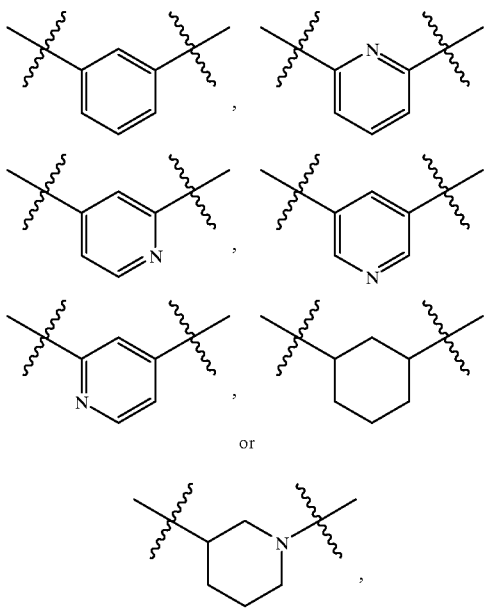

or

Y is a bond, —C(=O)—, —O—, —S—, —S(=O)—, —S(=O)₂—, —NH—, or —N(CH₃)—,

Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH₂—, (2-F-phenyl)CH₂—, (3-F-phenyl)
CH₂—, (4-F-phenyl)CH₂—, (2-Cl-phenyl)CH₂—,
(3-Cl-phenyl)CH₂, (4-Cl-phenyl)CH₂—, (2,3-diF-
phenyl)CH₂—, (2,4-diF-phenyl)CH₂—, (2,5-diF-
phenyl)CH₂—, (2,6-diF-phenyl)CH₂—, (3,4-diF-
phenyl)CH₂—, (3,5-diF-phenyl)CH₂—, (2,3-diCl-
phenyl)CH₂—, (2,4-diCl-phenyl)CH₂—, (2,5-diCl-
phenyl)CH₂—, (2,6-diCl-phenyl)CH₂—, (3,4-diCl-
phenyl)CH₂—, (3,5-diCl-phenyl)CH₂—, (3-F-4-Cl-
phenyl)CH₂—, (3-F-5-Cl-phenyl)CH₂—, (3-Cl-4-F-
phenyl)CH₂—, (2-MeO-phenyl)CH₂—, (3-MeO-
phenyl)CH₂—, (4-MeO-phenyl)CH₂—, (2-Me-
phenyl)CH₂—, (3-Me-phenyl)CH₂—, (4-Me-phenyl)
CH₂—, (2-MeS-phenyl)CH₂—, (3-MeS-phenyl)
CH₂—, 4-MeS-phenyl)CH₂—, (2-CF₃O-phenyl)
CH₂—, (3-CF₃O-phenyl)CH₂—, (4-CF₃O-phenyl)
CH₂—, (furanyl)CH₂—, (thienyl)CH₂—, (pyridyl)
CH₂—, (2-Me-pyridyl)CH₂—, (3-Me-pyridyl)CH₂—,
(4-Me-pyridyl)CH₂—, (1-imidazolyl)CH₂—,
(oxazolyl)CH₂—, (isoxazolyl)CH₂—,
(1-benzimidazolyl)CH₂—, (cyclopropyl)CH₂—,
(cyclobutyl)CH₂—, (cyclopentyl)CH₂—, (cyclohexyl)
CH₂—, (morpholino)CH₂—, (N-pipridinyl)CH₂—, or
(phenyl)₂CH—;

$R^{11}$, at each occurrence, is independently selected from H,
=O, methyl, ethyl, phenyl, benzyl, phenethyl, 4-F-
phenyl, (4-F-phenyl)CH₂—, (4-F-phenyl)CH₂CH₂—,
3-F-phenyl, (3-F-phenyl)CH₂—, (3-F-phenyl)
CH₂CH₂—, 2-F-phenyl, (2-F-phenyl)CH₂—, (2-F-
phenyl)CH₂CH₂—, 4-Cl-phenyl, (4-Cl-phenyl)CH₂—,
(4-Cl-phenyl)CH₂CH₂—, 3-Cl-phenyl, (3-Cl-phenyl)
CH₂—, (3-Cl-phenyl)CH₂CH₂—, 4-CH₃-phenyl,
(4-CH₃-phenyl)CH₂—, (4-CH₃-phenyl)CH₂CH₂—,
3-CH₃-phenyl, (3-CH₃-phenyl)CH₂—, (3-CH₃-
phenyl)CH₂CH₂—, 4-CF₃-phenyl, (4-CF₃-phenyl)
CH₂—, (4-CF₃-phenyl)CH₂CH₂—, pyrid-2-yl, 4-F-
pyrid-2-yl, 4-Cl-pyrid-2-yl, 4-CH₃-pyrid-2-yl, 4-CF₃-
pyrid-2-yl, pyrid-3-yl, 4-F-pyrid-3-yl, 4-Cl-pyrid-3-yl,
4-CH₃-pyrid-3-yl, 4-CF₃-pyrid-3-yl, or pyrid-4-yl; and $R^{13}$, at each occurrence, is independently selected from H,
F, Cl, OH, —CH₃, —CH₂CH₃, —OCH₃, or —CF₃.

[12] In another preferred embodiment, the present invention
provides for a compound of Formula (Ic):

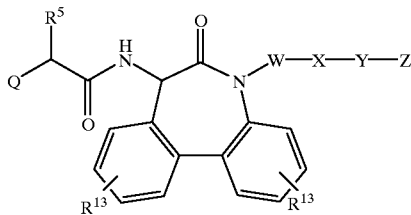

(Ic)

or a stereoisomer, pharmaceutically acceptable salt or pro-
drug thereof.

[13] In another preferred embodiment, the present invention
provides for a compound of Formula (Id):

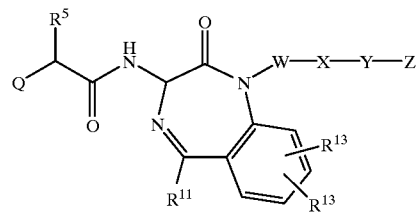

(Id)

or a stereoisomer, pharmaceutically acceptable salt or pro-
drug thereof.

[14] In another preferred embodiment, the present invention
provides for a compound of Formula (Ie):

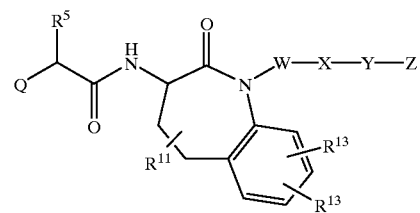

(Ie)

or a stereoisomer, pharmaceutically acceptable salt or pro-
drug thereof.

[15] In another preferred embodiment, the present invention
provides for a compound of Formula (If):

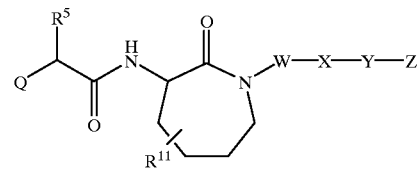

(If)

or a stereoisomer, pharmaceutically acceptable salt or pro-
drug thereof.

[16] In another preferred embodiment, the present invention
provides for a compound, or a pharmaceutically accept-
able salt or prodrug thereof, selected from:

(3S)-3-[(1-oxo-(2S)-2-cyclopropylmethyl-heptyl)]amino-1-
methyl-5-phenyl-2,3-dihydro-1H-1,4-benzodiazepin-2-
one;

(3S)-3-[(1-oxo-2-propyloctyl)]amino-1-methyl-5-phenyl-2,
3-dihydro-1H-1,4-benzodiazepin-2-one;

(3S)-3-[(1-oxo-2-propylnonanyl)]amino-1-methyl-5-
phenyl-2,3-dihydro-1H-1,4-benzodiazepin-2-one;

(3S)-3-[(1-oxo-2-butyloctyl)]amino-1-methyl-5-phenyl-2,
3-dihydro-1H-1,4-benzodiazepin-2-one;

(3S)-3-(1-oxo-2-methyloctyl)amino-1-methyl-5-phenyl-2,
3-dihydro-1H-1,4-benzodiazepin-2-one;

(3S)-3-[(1-oxo-2-pentylheptanyl)]amino-1-methyl-5-
phenyl-2,3-dihydro-1H-1,4-benzodiazepin-2-one;

(3S)-3-[(1-oxo-2-propylpentyl)]amino-1-methyl-5-phenyl-
2,3-dihydro-1H-1,4-benzodiazepin-2-one;

(3S)-3-[(1-oxo-2-methylpentyl)amino]-1-methyl-5-phenyl-
2,3-dihydro-1H-1,4-benzodiazepin-2-one;

3-[1-oxo-2-(S)-cyclopropylmethyl-heptyl]amino-1-methyl-5-(pyridin-2-yl)-2,3-dihydro-1H-1,4-benzodiazepine-2-one;

3-[1-oxo-2-(S)-cyclopropylmethyl-heptyl]amino-1-methyl-5-[4-methyl(pyridin-2-yl)]-2,3-dihydro-1H-1,4-benzodiazepin-2-one;

3-[1-oxo-2-(S)-cyclopropylmethyl-heptyl]amino-1-methyl-5-[4-trifluoromethyl(pyridin-2-yl)]-2,3-dihydro-1H-1,4-benzodiazepin-2-one;

3-[1-oxo-2-(S)-aminomethyl-heptyl]amino-1-methyl-(5-trifluoromethyl-phenyl)-2,3-dihydro-1H-1,4-benzodiazepine-2-one;

3-[1-oxo-2-(S)-(dimethylamino)methyl-heptyl]amino-1-methyl-5-(trifluoromethyl-phenyl)-2,3-dihydro-1H-1,4-benzodiazepine-2-one; and 3-(3-isopentyloxy-2-(R)-methyl-1-oxo-propyl)amino-1-methyl-5-(trifluoromethyl)phneyl-2,3-dihydro-1H-1,4-benzodiazepin-2-one.

[17] In another preferred embodiment, the present invention provides for a compound, or a pharmaceutically acceptable salt or prodrug thereof, selected from:

(7S)-[(2S)-1-oxo-2-pentyloxy-4-methylpentyl]amino-5-methyl-5H,7H-dibenzo[b,d]azepin-6-one.

It is appreciated that certain features of the invention, which are, for clarity, described herein in the context of separate embodiments, may also be provided in combination in a single embodiment. As such, it is understood that any and all embodiments of the present invention may be taken in conjunction with any other embodiment to describe additional embodiments of the present invention. Conversely, various features of the invention which are for brevity, described herein in the context of a single embodiment, may also be provided separately or in any subcombination. As such, it is understood that any elements of an embodiment are meant to be combined with any and all other elements from any of the embodiments to describe additional embodiments.

In a preferred embodiment Ring B is selected from:

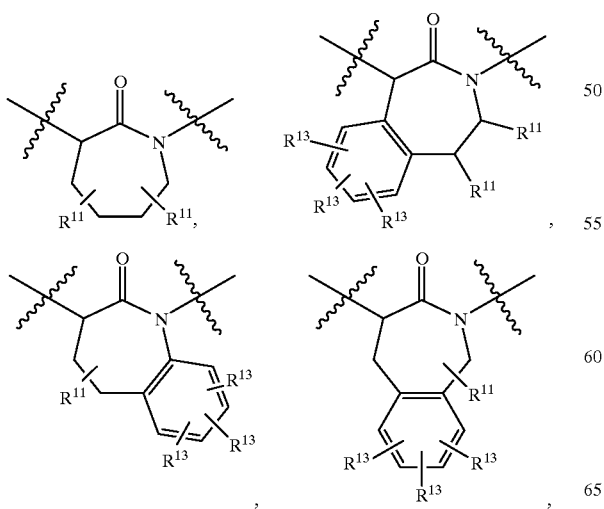

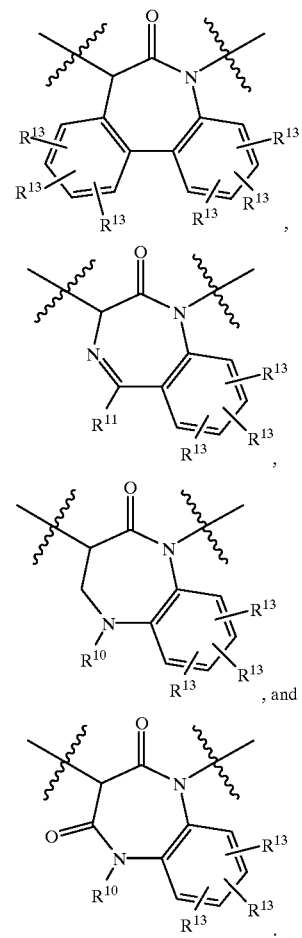

In another preferred embodiment Ring B is selected from:

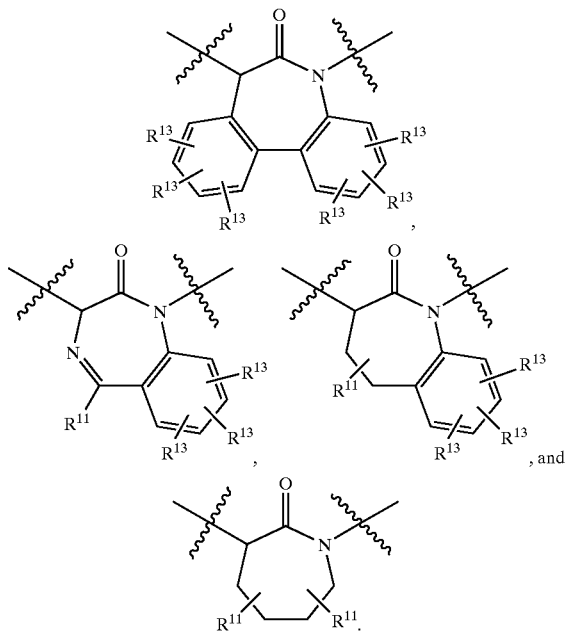

In another preferred embodiment Ring B is singly:

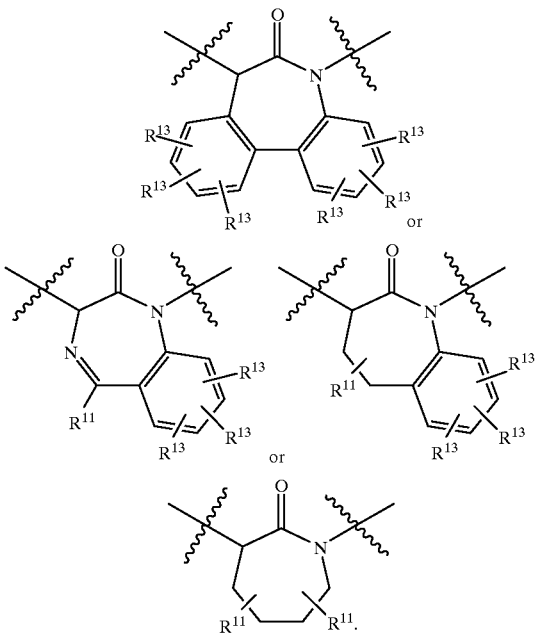

In another preferred embodiment Ring B is singly:

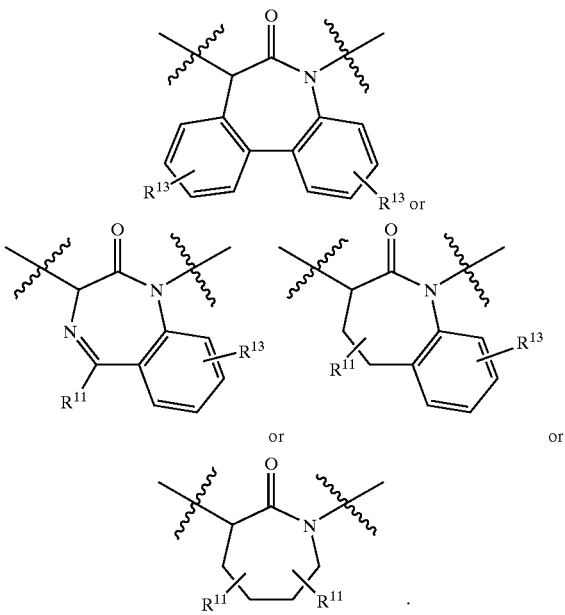

Also included in the present invention are compounds as set forth in the embodiments above wherein Q is —(CR$^7$R$^{7a}$)$_m$—R$^4$, —(CR$^7$R$^{7a}$)$_n$—S—R$^4$, —(CR$^7$R$^{7a}$)$_n$—O—R$^4$, or —(CR$^7$R$^{7a}$)$_m$—N(R$^{7b}$)—R$^4$.

In a preferred embodiment Q is —(CHR$^7$)$_m$—R$^4$, —(CHR$^7$)$_n$—S—R$^4$, —(CHR$^7$)$_n$—O—R$^4$, or —(CHR$^7$)$_m$—N(R$^{7b}$)—R$^4$.

In another preferred embodiment Q is —(CH$_2$)$_m$—R$^4$, —(CH$_2$)$_n$—S—R$^4$, —(CH$_2$)$_n$-O—R$^4$, or —(CH$_2$)$_m$—N(H)—R$^4$.

In another preferred embodiment Q is —(CH$_2$)$_m$—R$^4$, —(CH$_2$)$_n$—O—R$^4$, or —(CH$_2$)$_m$—N(H)—R$^4$.

In another preferred embodiment Q is —CH$_2$R$^4$, —O—R$^4$, —CH$_2$OR$^4$, or —CH$_2$—NH—R$^4$.

In another preferred embodiment Q is —CH$_2$R$^4$, —O—R$^4$, or —CH$_2$—NH—R$^4$.

In another preferred embodiment Q is —CH$_2$R$^4$.

In another preferred embodiment Q is —CH$_2$OR$^4$ or —O—R$^4$.

In another preferred embodiment Q is —CH$_2$OR$^4$.

In another preferred embodiment Q is —O—R$^4$.

In another preferred embodiment Q is —CH$_2$—NH—R$^4$.

In another preferred embodiment Q is —CH$_2$CH$_2$CH$_3$, —CH$_2$CH(CH$_3$)$_2$, —CH$_2$CH$_2$CH$_2$CH$_3$, —CH$_2$CH$_2$CH$_2$CH$_2$CH$_3$, —CH$_2$CH$_2$CH(CH$_3$)$_2$, —CH$_2$CH$_2$CH$_2$CH$_2$CH$_2$CH$_3$, —CH$_2$CH$_2$CH$_2$CH(CH$_3$)$_2$, —CH$_2$CH$_2$CH$_2$CH$_2$CH$_2$CH$_2$CH$_3$, or —CH$_2$CH$_2$CH$_2$CH$_2$CH(CH$_3$)$_2$.

In another preferred embodiment Q is —CH$_2$-cyclopropyl, —CH$_2$-cyclobutyl, —CH$_2$-cyclopentyl, —CH$_2$-cyclohexyl, —CH$_2$CH$_2$-cyclopropyl, —CH$_2$CH$_2$-cyclobutyl, —CH$_2$CH$_2$-cyclopentyl, or —CH$_2$CH$_2$-cyclohexyl.

In another preferred embodiment Q is —OCH$_3$, —OCH$_2$CH$_3$, —OCH$_2$CH$_2$CH$_3$, —OCH(CH$_3$)$_2$, —OCH$_2$CH$_2$CH$_2$CH$_3$, —OCH$_2$CH(CH$_3$)$_2$, —OCH$_2$CH$_2$CH(CH$_3$)$_2$, —OCH$_2$CH$_2$CH$_2$CH$_2$CH$_3$, —OCH$_2$CH$_2$CH$_2$CH$_2$CH$_2$CH$_3$, —OCH$_2$CH$_2$CH$_2$CH(CH$_3$)$_2$, or —OCH$_2$CH$_2$CH$_2$CH$_2$CH(CH$_3$)$_2$.

In another preferred embodiment Q is —OCH$_2$-cyclopropyl, —OCH$_2$-cyclobutyl, —OCH$_2$-cyclopentyl, —OCH$_2$-cyclohexyl, —OCH$_2$CH$_2$-cyclopropyl, —OCH$_2$CH$_2$-cyclobutyl, —OCH$_2$CH$_2$-cyclopentyl, or —OCH$_2$CH$_2$-cyclohexyl.

In another preferred embodiment Q is —CH$_2$OCH$_3$, —CH$_2$OCH$_2$CH$_3$, —CH$_2$OCH$_2$CH$_2$CH$_3$, —CH$_2$OCH(CH$_3$)$_2$, —CH$_2$OCH$_2$CH$_2$CH$_2$CH$_3$, —CH$_2$OCH$_2$CH(CH$_3$)$_2$, —CH$_2$OCH$_2$CH$_2$CH(CH$_3$)$_2$, —CH$_2$OCH$_2$CH$_2$CH$_2$CH$_2$CH$_3$, —CH$_2$OCH$_2$ CH$_2$CH$_2$CH$_2$CH$_3$, —CH$_2$OCH$_2$CH$_2$CH$_2$CH(CH$_3$)$_2$, or —CH$_2$OCH$_2$CH$_2$CH$_2$CH$_2$CH(CH$_3$)$_2$.

In another preferred embodiment Q is —CH$_2$OCH$_2$-cyclopropyl, CH$_2$OCH$_2$-cyclobutyl, CH$_2$OCH$_2$-cyclopentyl, CH$_2$OCH$_2$-cyclohexyl, CH$_2$OCH$_2$CH$_2$-cyclopropyl, CH$_2$OCH$_2$CH$_2$-cyclobutyl, CH$_2$OCH$_2$CH$_2$-cyclopentyl, or CH$_2$OCH$_2$CH$_2$-cyclohexyl.

It is provided that in the definition of Q, when n is 0 then R$^4$ can not be H.

Also included in the present invention are compounds as set forth in the embodiments above wherein the integer m may be selected from 1, 2, or 3.

In another preferred embodiment the integer m is 1 or 2.

In another preferred embodiment the integer m is 2.

In another preferred embodiment the integer m is 1.

Also included in the present invention are compounds as set forth in the embodiments above wherein the integer n may be selected from 0, 1, or 2; provided that when n is 0 then R$^4$ can not be H.

In another preferred embodiment the integer n is 0 or 1.

In another preferred embodiment the integer n is 0.

In another preferred embodiment the integer n is 1.

In another preferred embodiment the integer n is 2.

Also included in the present invention are compounds as set forth in the embodiments above wherein R$^4$ is H, C$_1$–C$_8$ alkyl, C$_2$–C$_8$ alkenyl, C$_2$–C$_8$ alkynyl, or C$_3$–C$_{10}$ carbocycle.

In another preferred embodiment R$^4$ is C$_2$–C$_8$ alkyl, C$_2$–C$_8$ alkenyl, C$_2$–C$_8$ alkynyl, or C$_3$–C$_6$ cycloaklyl.

In another preferred embodiment R$^4$ is C$_3$–C$_8$ alkyl, C$_3$–C$_8$ alkenyl, C$_3$–C$_8$ alkynyl, or C$_3$–C$_6$ cycloaklyl.

In another preferred embodiment R$^4$ is C$_4$–C$_8$ alkyl, C$_4$–C$_8$ alkenyl, C$_4$–C$_8$ alkynyl, or C$_3$–C$_6$ cycloaklyl.

In another preferred embodiment $R^4$ is $C_2$–$C_8$ alkyl.
In another preferred embodiment $R^4$ is $C_3$–$C_8$ alkyl.
In another preferred embodiment $R^4$ is $C_4$–$C_8$ alkyl.

Also included in the present invention are compounds as set forth in the embodiments above wherein $R^5$ is $C_1$–$C_8$ alkyl, $C_2$–$C_8$ alkenyl, $C_2$–$C_8$ alkynyl, or ($C_3$–$C_6$ cycloalkyl)$C_1$–$C_4$ alkyl, $(NR^{15}R^{16})C_1$–$C_4$ alkyl.

In another preferred embodiment $R^5$ is $C_2$–$C_8$ alkyl, $C_2$–$C_8$ alkenyl, or $C_2$–$C_8$ alkynyl.

In another preferred embodiment $R^5$ is $C_3$–$C_8$ alkyl, $C_3$–$C_8$ alkenyl, or $C_3$–$C_8$ alkynyl.

In another preferred embodiment $R^5$ is $C_4$–$C_8$ alkyl, $C_4$–$C_8$ alkenyl, $C_4$–$C_8$ alkynyl.

In another preferred embodiment $R^5$ is $C_2$–$C_8$ alkyl.
In another preferred embodiment $R^5$ is $C_3$–$C_8$ alkyl.
In another preferred embodiment $R^5$ is $C_4$–$C_8$ alkyl.

In another preferred embodiment $R^5$ is ($C_3$–$C_6$ cycloalkyl)$C_1$–$C_4$ alkyl.

In another preferred embodiment $R^5$ is $(NR^{15}R^{16})C_1$–$C_4$ alkyl.

In another preferred embodiment $R^5$ is —$CH_3$, —$CH_2CH_3$, —$CH_2CH_2CH_3$, —$CH_2CH(CH_3)_2$, —$CH_2CH_2CH_2CH_3$, —$CH_2CH_2CH_2CH_2CH_3$, —$CH_2CH_2CH(CH_3)_2$, —$CH_2CH_2CH_2CH_2CH_3$, —$CH_2CH_2CH_2CH(CH_3)_2$, —$CH_2CH_2CH_2CH_2CH(CH_3)_2$, —$CH_2NH_2$, —$CH_2N(CH_3)_2$, —$CH_2N(CH_2CH_3)_2$, —$CH_2CH_2NH_2$, —$CH_2CH_2N(CH_3)_2$, —$CH_2CH_2N(CH_2CH_3)_2$, —$CH_2$-cyclopropyl, —$CH_2$-cyclobutyl, —$CH_2$-cyclopentyl, or —$CH_2$-cyclohexyl.

In another preferred embodiment $R^5$ is —$CH_3$, —$CH_2CH_3$, —$CH_2CH_2CH_3$, —$CH_2CH(CH_3)_2$, —$CH_2CH_2CH_2CH_3$, —$CH_2CH_2CH_2CH_2CH_3$, —$CH_2CH_2CH(CH_3)_2$, —$CH_2CH_2CH_2CH_2CH_3$, —$CH_2CH_2CH_2CH(CH_3)_2$, or $CH_2CH_2CH_2CH_2CH(CH_3)_2$.

In another preferred embodiment $R^5$ is —$CH_2NH_2$, —$CH_2N(CH_3)_2$, —$CH_2N(CH_2CH_3)_2$, —$CH_2CH_2NH_2$, —$CH_2CH_2N(CH_3)_2$, or —$CH_2CH_2N(CH_2CH_3)_2$.

In another preferred embodiment $R^5$ is —$CH_2$-cyclopropyl, —$CH_2$-cyclobutyl, —$CH_2$-cyclopentyl, or —$CH_2$-cyclohexyl.

Also included in the present invention are compounds as set forth in the embodiments above wherein $R^6$ is H.

Also included in the present invention are compounds as set forth in the embodiments above wherein $R^{11}$ is H, $NR^{18}R^{19}$; $C_1$–$C_4$ alkyl optionally substituted with 0–1 $R^{11a}$; phenyl substituted with 0–3 $R^{11b}$; $C_3$–$C_6$ cycloalkyl substituted with 0–3 $R^{11b}$; or pyridinyl substituted with 0–3 $R^{11b}$;

wherein $R^{11a}$ is phenyl substituted with 0–3 $R^{11b}$; wherein $R^{11b}$, at each occurrence, is independently selected from H, OH, Cl, F, $CF_3$, methyl, ethyl, propyl, butyl, methoxy, ethoxy, and propoxy.

In another preferred embodiment $R^{11}$ is independently selected from H, methyl, ethyl, phenyl, benzyl, phenethyl, 4-F-phenyl, (4-F-phenyl)$CH_2$—, (4-F-phenyl)$CH_2CH_2$—, 3-F-phenyl, (3-F-phenyl)$CH_2$—, (3-F-phenyl)$CH_2CH_2$—, 2-F-phenyl, (2-F-phenyl)$CH_2$—, (2-F-phenyl)$CH_2CH_2$—, 4-Cl-phenyl, (4-Cl-phenyl)$CH_2$—, (4-Cl-phenyl)$CH_2CH_2$—, 3-Cl-phenyl, (3-Cl-phenyl)$CH_2$—, (3-Cl-phenyl)$CH_2CH_2$—, 4-$CH_3$-phenyl, (4-$CH_3$-phenyl)$CH_2$—, (4-$CH_3$-phenyl)$CH_2CH_2$—, 3-$CH_3$-phenyl, (3-$CH_3$-phenyl)$CH_2$—, (3-$CH_3$-phenyl)$CH_2CH_2$—, 4-$CF_3$-phenyl, (4-$CF_3$-phenyl)$CH_2$—, (4-$CF_3$-phenyl)$CH_2CH_2$—, pyrid-2-yl, 4-F-pyrid-2-yl, 4-Cl-pyrid-2-yl, 4-$CH_3$-pyrid-2-yl, 4-$CF_3$-pyrid-2-yl, pyrid-3-yl, 4-F-pyrid-3-yl, 4-Cl-pyrid-3-yl, 4-$CH_3$-pyrid-3-yl, 4-$CF_3$-pyrid-3-yl, and pyrid-4-yl.

In another preferred embodiment $R^{11}$ is independently selected from H, methyl, ethyl, phenyl, 4-F-phenyl, 3-F-phenyl, 2-F-phenyl, 4-Cl-phenyl, 3-Cl-phenyl, 4-$CH_3$-phenyl, 3-$CH_3$-phenyl, 4-$CF_3$-phenyl, pyrid-2-yl, 4-F-pyrid-2-yl, 4-Cl-pyrid-2-yl, 4-$CH_3$-pyrid-2-yl, and 4-$CF_3$-pyrid-2-yl.

Also included in the present invention are compounds as set forth in the embodiments above wherein W may be selected from a bond, —$CH_2$—, —$CH_2CH_2$—, or —$CH(CH_3)$—.

In another preferred embodiment W is a bond or —$(CH_2)_p$—.

In another preferred embodiment W is a bond, —$CH_2$—, or —$CH_2CH_2$—.

In another preferred embodiment W is a bond or —$CH_2$—.

In another preferred embodiment W is —$CH_2$—.

In another preferred embodiment W is a bond.

Also included in the present invention are compounds as set forth in the embodiments above wherein the integer p may be selected from 0, 1, 2, or 3.

In another preferred embodiment the integer p is 0, 1 or 2.

In another preferred embodiment the integer p is 0 or 1.

In another preferred embodiment the integer p is 0.

Also included in the present invention are compounds as set forth in the embodiments above wherein X is a bond, $C_6$–$C_{10}$ aryl, $C_3$–$C_{10}$ carbocycle or 5 to 10 membered heterocycle.

In another preferred embodiment X is a bond, phenyl, $C_3$–$C_6$ carbocycle, or 5 to 6 membered heterocycle.

In another preferred embodiment X is a bond, phenyl, $C_3$–$C_6$ cycoalkyl, or 5 to 6 membered heterocycle.

In another preferred embodiment X is a bond;

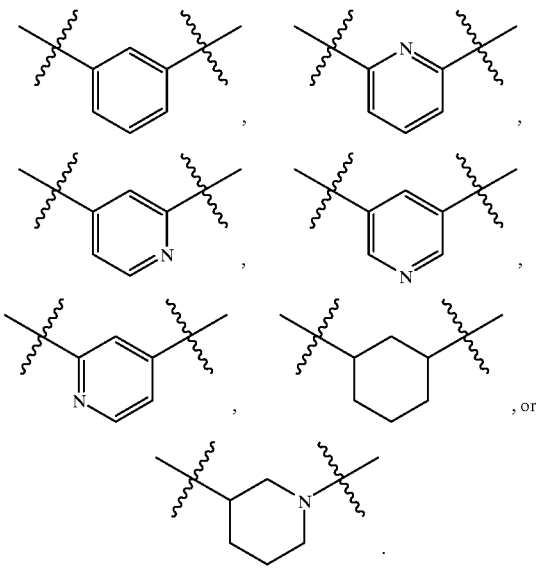

In another preferred embodiment X is a bond;

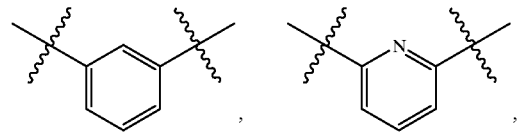

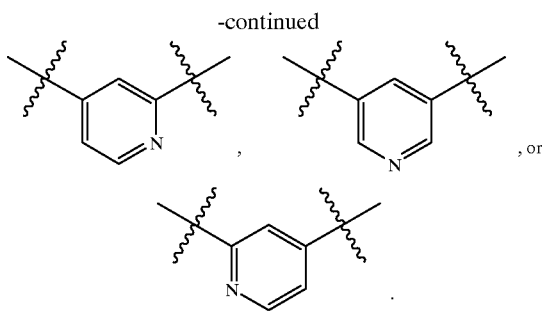

In another preferred embodiment X is a bond or phen-1,3-diyl.

In another preferred embodiment X is phen-1,3-diyl.

In another preferred embodiment X is a bond.

Also included in the present invention are compounds as set forth in the embodiments above wherein Y is a bond, —C(=O)—, —O—, —S—, —S(=O)—, —S(=O)$_2$—, —N(R$^{19}$)—, C(=O)NR$^{19b}$—, —NR$^{19b}$C(=O)—, —NR$^{19b}$S(=O)$_2$—, —S(=O)$_2$NR$^{19b}$, —NR$^{19b}$S(=O)—, —S(=O)NR$^{19b}$—, —C(=O)O—, or —OC(=O)—.

In another preferred embodiment Y is a bond, —C(=O)—, —O—, —S—, —S(=O)—, —S(=O)$_2$—, —NH—, —N(CH$_3$)—, —C(=O)NH—, —NHC(=O)—, —NHS(=O)$_2$—, —S(=O)$_2$NH—, —NHS(=O)—, —S(=O)NH—, —C(=O)O—, or —OC(=O)—.

In another preferred embodiment Y is a bond, —C(=O)—, —O—, —S—, —S(=O)—, —S(=O)$_2$—, —NH—, —N(CH$_3$)—, or —N(CH$_2$CH$_3$)—.

In another preferred embodiment Y is a bond, —C(=O)—, —O—, —S—, —S(=O)—, —S(=O)$_2$—, —NH—, or —N(CH$_3$)—.

In another preferred embodiment Y is a bond, —C(=O)—, —O—, —NH—, or —N(CH$_3$)—.

In another preferred embodiment Y is —O—.

In another preferred embodiment Y is —NH—.

In another preferred embodiment Y is —N(CH$_3$)—.

In another preferred embodiment Y is a bond.

Also included in the present invention are compounds as set forth in the embodiments above wherein Z is C$_1$–C$_4$ alkyl, C$_2$–C$_4$ alkenyl, C$_2$–C$_4$ alkynyl, C$_1$–C$_2$ alkyl substituted with 1–2 R$^{12a}$; phenyl substituted with 0–4 R$^{12b}$; C$_3$–C$_6$ carbocycle substituted with 0–3 R$^{12b}$; or 5 to 6 membered heterocycle containing 1 to 4 heteroatoms selected from nitrogen, oxygen, and sulphur, wherein said 5 to 6 membered heterocycle is substituted with 0–3 R$^{12b}$; wherein R$^{12a}$ is phenyl substituted with 0–4 R$^{12b}$; C$_3$–C$_6$ carbocycle substituted with 0–4 R$^{12b}$; or 5 to 6 membered heterocycle containing 1 to 4 heteroatoms selected from nitrogen, oxygen, and sulphur, wherein said 5 to 6 membered heterocycle is substituted with 0–3 R$^{12b}$; and wherein R$^{12b}$ at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, and —OCF$_3$;

In another preferred embodiment Z is C$_1$–C$_2$ alkyl substituted with 1–2 R$^{12a}$; or phenyl substituted with 0–4 R$^{12b}$; wherein R$^{12a}$ is phenyl substituted with 0–4 R$^{12b}$; wherein R$^{12b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, and —OCF$_3$;

In another preferred embodiment Z is C$_1$–C$_4$ alkyl, C$_2$–C$_4$ alkenyl, or C$_2$–C$_4$ alkynyl.

In another preferred embodiment Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, (cyclopropyl)CH$_2$—, (cyclobutyl)CH$_2$—, (cyclopentyl)CH$_2$—, (cyclohexyl)CH$_2$—, (morpholino)CH$_2$—, (N-pipridinyl)CH$_2$—, or (phenyl)$_2$CH—.

In another preferred embodiment Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, or 4-phenyl-phenyl.

In another preferred embodiment Z is phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl) CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, or (phenyl)$_2$CH—.

Also included in the present invention are compounds as set forth in the embodiments above wherein R$^{13}$, at each occurrence, is independently selected from H, F, Cl, OH, —CH$_3$, —CH$_2$CH$_3$, —OCH$_3$, and —CF$_3$.

Also included in the present invention are compounds as set forth in the embodiments above wherein R$^{14}$ is H, phenyl, benzyl, methyl, ethyl, propyl, or butyl;

Also included in the present invention are compounds as set forth in the embodiments above wherein $R^{15}$, at each occurrence, is independently selected from H, methyl, ethyl, propyl, and butyl.

Also included in the present invention are compounds as set forth in the embodiments above wherein $R^{16}$, at each occurrence, is independently selected from H, OH, methyl, ethyl, propyl, butyl, benzyl, and phenethyl.

Also included in the present invention are compounds as set forth in the embodiments above wherein $R^{18}$, at each occurrence, is independently selected from H, methyl, ethyl, propyl, butyl, phenyl, benzyl, and phenethyl.

Also included in the present invention are compounds as set forth in the embodiments above wherein $R^{19}$, at each occurrence, is independently selected from H, methyl, ethyl, propyl, and butyl.

Also included in the present invention are compounds as set forth in the embodiments above wherein in the moiety $R^4$—$(CR^7R^{7a})m$—$(R^5)CH$— of Formula (I) when $R^4$ is an alkyl, alkenyl, or alkynyl moiety; and $R^5$ is an alkyl, alkenyl, or alkynyl moiety; then the total number of carbon atoms in the backbone of $R^4$—$(CR^7R^{7a})m$—$(R^5)CH$— equals nine or more. For example, when $R^5$ is methyl, then $R^4$—$(CR^7R^{7a})m$— is heptyl (branched or linear) or greater. For example, when $R^5$ is ethyl, then $R^4$—$(CR^7R^{7a})m$— is hexyl (branched or linear) or greater. It is understood that the proviso is only intended to define the number of carbon atoms, continuously linked in the backbone of the $R^4$—$(CR^7R^{7a})m$— $(R^5)CH$— moiety and not meant to limit substitution by $R^{4a}$ or $R^{5b}$ on the $R^4$—$(CR^7R^{7a})m$—$(R^5)CH$—.

Also included in the present invention are compounds as set forth in the embodiments above wherein in the moiety $R^4$—$O(CR^7R^{7a})n$—$(R^5)CH$— of Formula (I) when —$(CR^7R^{7a})n$—$(R^5)CH$— is $C_1$–$C_8$ alkyl, $C_2$–$C_8$ alkenyl, $C_3$–$C_{10}$ cycloalkyl-$C_1$–$C_4$ alkyl, $C_6$–$C_{10}$ aryl-$C_1$–$C_4$ alkyl, $C_6$–$C_{10}$ aryl-$C_2$–$C_4$ alkynyl, then $R^4$ is other than H, methyl, ethyl, isopropyl, phenyl, or benzyl.

Also included in the present invention are compounds as set forth in the embodiments above wherein in the moiety $R^4$—$O(CR^7R^{7a})n$—$(R^5)CH$— of Formula (I) when —$(CR^7R^{7a})n$—$(R^5)CH$— is $C_1$–$C_4$ alkyl, then $R^4$ is other than $C_1$–$C_4$ alkyl.

Also included in the present invention are compounds as set forth in the embodiments above wherein in the moiety $R^4$—$NR^{7b}(CR^7R^{7a})n$—$(R^5)CH$— of Formula (I) when —$(CR^7R^{7a})n$ —$(R^5)CH$— is $C_2$–$C_4$ alkyl, then $R^4$ is other than $C_2$–$C_4$ alkyl.

In a second embodiment, the present invention provides a pharmaceutical composition comprising a compound of Formula (I) and a pharmaceutically acceptable carrier.

In a third embodiment, the present invention provides a method for the treatment of neurological disorders associated with β-amyloid production comprising administering to a host in need of such treatment a therapeutically effective amount of a compound of Formula (I).

In a preferred embodiment the neurological disorder associated with β-amyloid production is Alzheimer's Disease.

In a fourth embodiment, the present invention provides a method for inhibiting γ-secretase activity for the treatment of a physiological disorder associated with inhibiting γ-secretase activity comprising administering to a host in need of such inhibition a therapeutically effective amount of a compound of Formula (I) that inhibits γ-secretase activity.

Thus, the present invention provides a method for inhibiting γ-secretase activity comprising administering to a host in need of such inhibition a therapeutically effective amount of a compound of Formula (I) that inhibits γ-secretase activity.

In a preferred embodiment the physiological disorder associated with inhibiting γ-secretase activity is Alzheimer's Disease.

In a fifth embodiment, the present invention provides a compound of Formula (I) for use in therapy.

In a preferred embodiment the present invention provides a compound of Formula (I) for use in therapy of Alzheimer's Disease.

In a sixth embodiment, the present invention provides for the use of a compound of Formula (I) for the manufacture of a medicament for the treatment of Alzheimer's Disease.

Definitions

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No 4,666,829. The 43 amino acid sequence is:

1
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^{5b}$) occurs more than one time in any constituent or formula for a compound, its definition at each occurrence is independent of its definition at every other occurrence. Thus, for example, if a group is shown to be substituted with 0–3 $R^{5b}$, then said group may optionally be substituted with up to three $R^{5b}$ groups and $R^{5b}$ at each occurrence is selected independently from the definition of $R^{5b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1, 2, 3, 4, 5, or 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group, unless otherwise specified, is "$C_1$–$C_4$ alkyl". Additionally, unless otherwise specified, "propyl" denotes n-propyl or i-propyl; "butyl" denotes n-butyl, i-butyl, sec-butyl, or t-butyl.

As used herein, "alkenyl" or "alkenylene" is intended to include hydrocarbon chains of either a straight or branched configuration and one or more unsaturated carbon-carbon bonds which may occur in any stable point along the chain. Examples of "$C_2$–$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl", or "alkynylene" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred "carbocycle" are cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$–$C_{10}$ aryl" or aromatic residue, is intended to mean an aromatic moiety containing the specified number of carbon atoms; for example phenyl, pyridinyl or naphthyl. Preferred "aryl" is phenyl. Unless otherwise specified, "aryl" may be unsubstituted or substituted with 0 to 3 groups selected from H, methyl, ethyl, propyl, butyl, methoxy, ethoxy, propoxy, butoxy, amino, hydroxy, Cl, F, Br, I, $CF_3$, $SCH_3$, $S(O)CH_3$, $SO_2CH_3$, —$N(CH_3)_2$, $N(CH_3)H$, CN, $NO_2$, $OCF_3$, $C(=O)CH_3$, $CO_2H$, $CO_2CH_3$, or $C_1$–$C_4$ haloalkyl.

As used herein, the term "heteroaryl fused radical" is intended to denote a 5 or 6 membered aromatic ring comprising carbon atoms and one or two heteroatoms selected from nitrogen, sulphur and oxygen. The 5 or 6 membered ring is fused to two adjacent atoms of a second ring, i.e. forming a bicyclic ring system, wherein the second ring is lactam ring B. Examples of a "heteroaryl fused radical" are furanyl, imidazolyl, isoxazolyl, oxazolyl, pyrrolyl, thiophenyl, thiazolyl, isothiozalyl, pyridyl, pyridazinyl, pyrimidinyl, and pyrazinyl.

The phrase "additional lactam carbons", as used herein, is intended to denote the number of optional carbon atoms in the lactam ring B of Formula (I). Formula (I"):

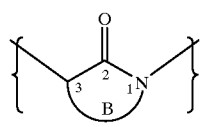

(I")

represents the lactam ring B of Formula (I). Additional lactam carbons are carbons in lactam ring B other than the carbons numbered 2 and 3 in the backbone of the formula. The additional lactam carbons may be optionally replaced by a heteroatom selected from oxygen, nitrogen and sulfur. Lactam ring B contains 1, 2, 3, 4, 5, 6 or 7 optional carbons, wherein one optional carbon may optionally be replaced by a heteroatom, such that the total number of members of lactam ring B, including atoms numbered 1, 2 and 3 in the backbone, does not exceed 10. It is preferred that the total number of atoms of lactam ring B is 6, 7 or 8; it is more preferred that the total number of atoms of lactam ring B is seven. It is further understood that lactam ring B may optionally be unsaturated or partially unsaturated (i.e. two adjacent atoms in the ring form a double bond) wherein the backbone of lactam ring B may contain one, two or three double bonds. Examples of lactam ring B include:

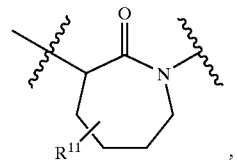

B1

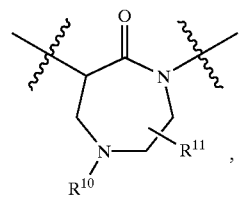

B2

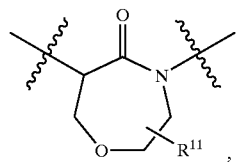

B3

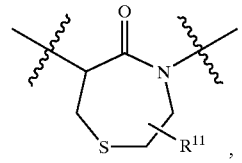

B4

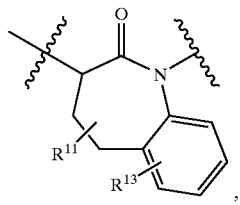

B5

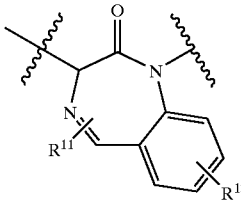

B6

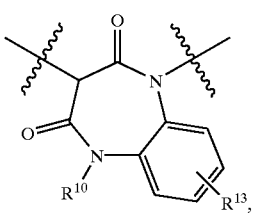

B8

-continued

B9
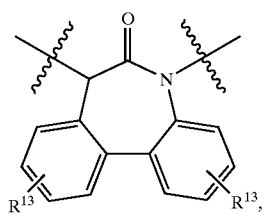

B10
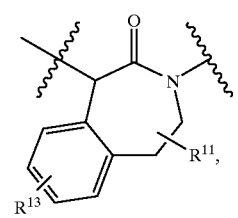

B11
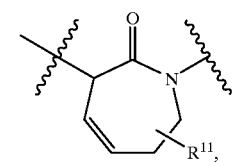

B12
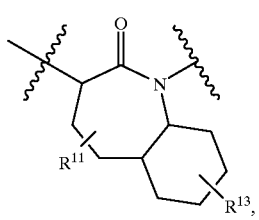

B13
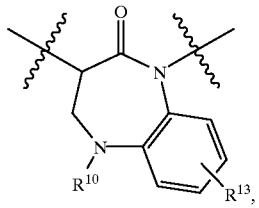

B14
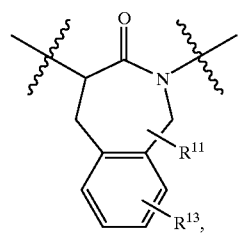

B15
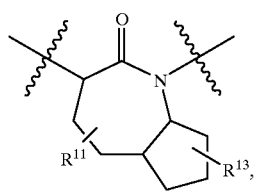

-continued

B16
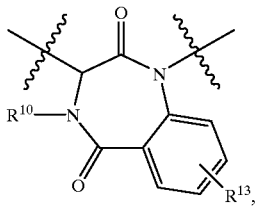

but are not intended to limit the invention. Preferred examples of lactam ring B are B1, B2, B5, B6, B8, B9, B13, and B16; more preferred examples of lactam ring B are B1, B6, B8, B9, and B13. Preferred examples of substituent $R^{10}$ or $R^{11}$ on lactam B are hydrogen, methyl, ethyl, phenyl, benzyl, phenethyl, 4-fluorophenyl, 4-chlorophenyl, 4-methylphenyl, 4-CF$_3$-phenyl, (4-fluorophenyl)methyl, (4-chlorophenyl)methyl, (4-methylphenyl)methyl, (4-CF$_3$-phenyl)methyl, (4-fluorophenyl)ethyl, (4-chlorophenyl)ethyl, (4-methylphenyl)ethyl, (4-CF$_3$-phenyl)ethyl, and 2-, 3-, and 4-pyridinyl. More preferred examples of substituent $R^{10}$ or $R^{11}$ on lactam B are methyl, ethyl, phenyl, 4-fluorophenyl, 4-chlorophenyl, 4-CF$_3$-phenyl, (4-fluorophenyl)methyl, (4-chlorophenyl)methyl, (4-CF$_3$-phenyl)methyl, and 2-, 3-, and 4-pyridinyl. Preferred examples of $R^{13}$ on lactam B are F, Cl, OH, methyl, ethyl, methoxy, and trifluoromethyl.

The compounds herein described may have asymmetric centers. One enantiomer of a compound of Formula (I) may display superior biological activity over the opposite enantiomer. For example carbon 3 of lactam ring B Formula (I″) may exist in either an S or R configuration. Thus, an R or S configuration at carbon 3 in Formula (I″-3R) and (I″-3S) are considered part of the invention. Examples of such configuration include, (I″-3S)
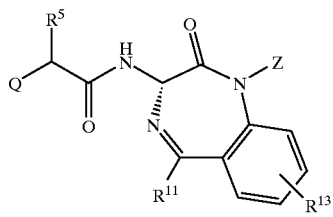

and (I″-3R)
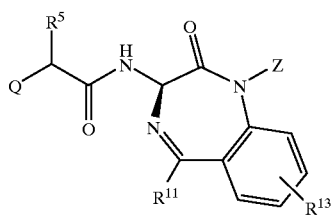

but are not intended to be limited to this example of ring B. When required, separation of the racemic material can be achieved by methods known in the art. Additionally when the carbon atom to which Q and $R^5$ are attached is chiral, both the R and S configurations of the carbon atom are considered part of the invention.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and acetamide, formamide, and benzamide derivatives of amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of Formula (I) of the present invention can be synthesized by the method of Scheme 1 comprising: step 1, an amino acid coupling; followed by step 2, a radical reduction; and an optional step 3, a reaction with $R^6$-LG where LG is a leaving group, for example halide, mesylate, triflate or other leaving group well known to one skilled in the art. See Scheme 1. In the method of Scheme 1, step 1, a W-X-Y-Z-substituted aminolactam, XI, is coupled with an β-hydroxy acid X to form a lactam XII. The amine XI is coupled to an appropriately substituted carboxylic acid or acid chloride by methods well described in the literature for making amide bonds, for example, TBTU in DMF with a base, for example, NMM to give the elaborated compound XII. In step 2, the lactam XII is then reacted with thiocarbonyl diimidazole to form a carbonyl derivative XIII which is then converted to a compound of Formula (Ia') by a radical hydride reduction. The deoxygenation of lactam XII to a

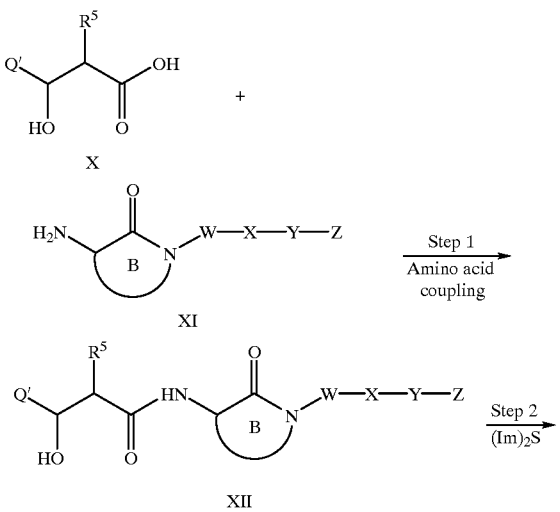

Scheme 1

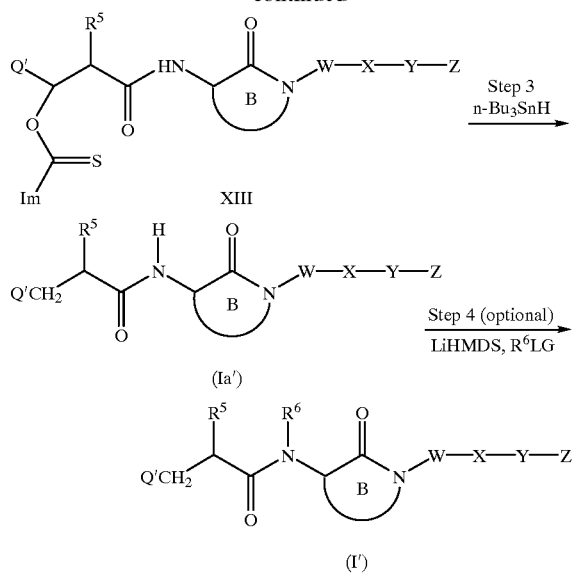

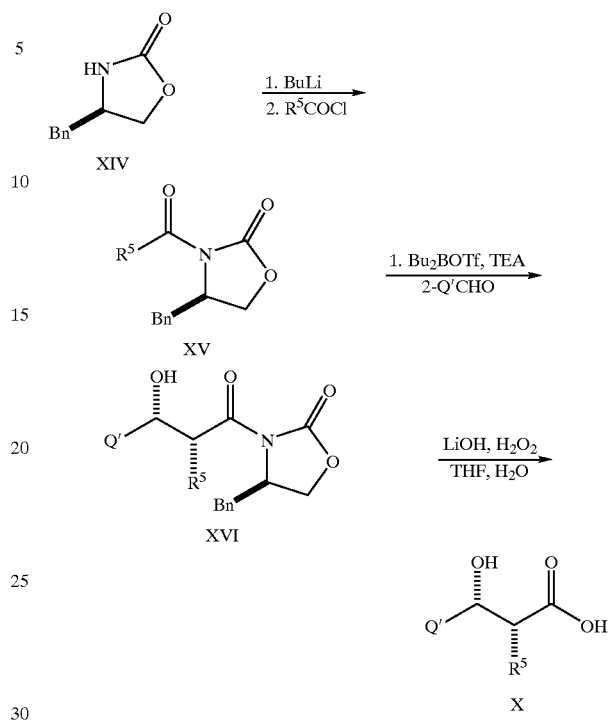

compound of Formula (Ia') can be prepared by means of a free radical deoxygenation procedure [Barton and McCarobie, J. Chem. Soc. Perkin Trans. 1, 1574 (1975); Robins et al., J. Am Chem. Soc. 103, 933 (1981); 105, 4059 (1983); Barton and Motherwell, Pure & Appl. Chem., 53, 15 (1981)]. This process entails the conversion of the free hydroxy group in compound XII to a suitable derivative, for example, a thiono-ester XIII. Upon treatment with a hydrogen radical source in the presence of a radical initiator, compound XIII undergoes reductive deoxygenation to furnish compounds of general structure (Ia'). For such deoxygenation reactions, suitable sources of hydrogen radicals are the trialkyltin hydrides (e.g. tributyltin hydride) or tris (trialkylsilyl) silanes (e.g. $(Me_3Si)_3SiH$) [Schummer and Hofle, Syn. Lett. 106 (1990); Ballestri et al., J. Org. Chem. 56, 678 (1991)], and suitable radical initiators are provided by azaisobutyronitrile (AIBN), heat, or irradiation. A compound of Formula (Ia') can be alkylated using standard bases, for example LDA, NaH, or NaHMDS, to deprotonate the amide followed by addition of an alkylating agent with an appropriate leaving group (LG) for example halide, mesylate, or triflate, in an appropriate solvent to provide a compound of Formula (I') with an $R^6$ substituent.

Aldol derivatives X (Scheme 2) can be prepared by the procedure of Evans (D. A. Evans et al, *Org. Synth.* 1990, 68, 83–90). Acylation of an oxazolidinone XIV with an acid chloride provides acylated oxazolidinone XV. The reaction of XV with an aldehyde Q'CHO in the presence of dibutyl boron triflate gives an aldol product XVI. The chiral auxiliary of the aldol product XVI is then removed to give a β-hydroxy-carboxylic acid product X. Additional examples are found in D. A. Evans *Aldrichimica Acta* 1982, 15, 23–32. Alternative syntheses of compound X can be accomplished by the methods of Crimmins (M. T. Crimmins et al, *J. Am. Chem. Soc.* 1997, 119, 7883–7884), Paterson (I. Paterson et al, *Org. React.* 1997, 51, 1–200) and Mukaiyama (T. Mukaiyama et al, Org. React. 1994, 1–104).

Methods for the synthesis of lactams useful as intermediates in the synthesis of compounds as contemplated by the present invention in lactam ring B in Formula (I), including amino benzodiazepinones, amino dibenzoazepinones and other related heterocycles, are known in the art and are disclosed in a number of references including PCT publication number WO98/28268, WO99/66934, and WO00/07995, which are hereby incorporated by reference. Additional references include Bock, et al, J. Org. Chem., 1987, 52, 3232–3239; Sherrill et al, J. Org. Chem., 1995, 60, 730–734; and Walsh, D. A., Synthesis, September 1980, p.677; and Brown, at. al., Tetrahedron Letters, 1971, 8, 667–670.

An example of an L-α-amino-β-thio-ε-caprolactam, as shown in Scheme 3, where ring B is the amino lactam of XVII and J is a sulfur atom has been reported in the literature. See S. A. Ahmed et al, FEBS Letters, (1984), vol. 174, pages 76–9. One skilled in the art can extend this methodology to the synthesis of β-amino and oxygen containing rings by analogy. The sulfur-containing molecules can also be oxidized to the sulfoxide and sulfone by methods known to one skilled in the art.

Scheme 3

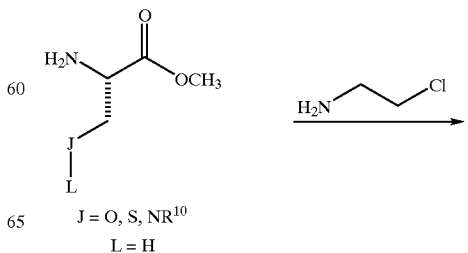

$J = O, S, NR^{10}$
$L = H$

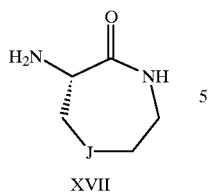

XVII

The WXYZ-substituted amino lactam XI can be formed by alkylation of an amino lactam with WXYZ-LG. For example in Scheme 4, the α-amine of compound XVIII can be protected with a BOC group. The protected α-amine XVIII of the α-amino-ε-caprolactam can be prepared by methods well known in the literature for amino protecting groups as discussed in Theodora W. Greene's book "Protective Groups in Organic Synthesis", like N-Boc using di-t-butyldicarbonate in an appropriate solvent like DMSO. The lactam nitrogen of compound XV can be alkylated by generating the anion with bases such as LDA, lithium bis(trimethylsilyl)amide or sodium hydride in solvents like THF, with or without cosolvents such as DMPU or HMPA and reacting this with a variety of groups containing leaving groups (LG) like bromide, iodide, mesylate or tosylate. Alkylating agents such as α-bromo amides, ketones and acids can be prepared by a number of literature methods including halogenation of amino acids by diazotization or are commercially available. Other suitable alkylating agents such as alkyl, allylic and benzylic halides can be formed form a variety of precursors such as free-radical addition of halides or activation of alcohols, and other chemistries known to those skilled in the art. For discussion of these types of reactions, see Carey, F. A. and Sundberg, R. J., Advanced Organic Chemistry, Part A, New York: Plenum Press, 1990, pages 304–305, 342–347, 695–698. The N-Boc protecting group can be removed by any number of methods well known in the literature like TFA in methylene chloride to give the compound XIa.

Scheme 4

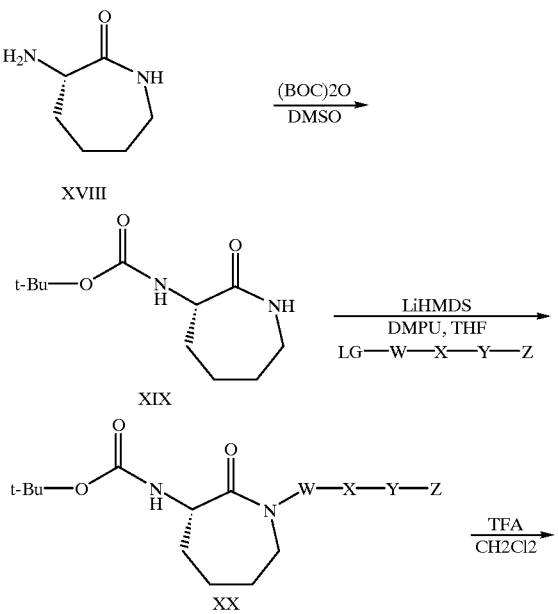

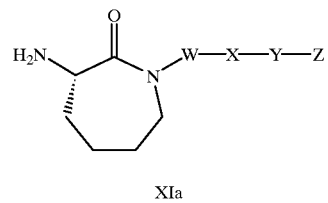

XIa

An example of the method of Scheme 1 is illustrated in the preparation of compound 5 (Scheme 5). The aldol product 3 is obtained from an amino acid coupling of an β-hydroxyacid 1 and a benzodiazepine 2 using a standard coupling procedure. The coupled aldol product 3 is reacted with thiocarbonyl diimidazole in 1,2-dichloroethane to form a thiocarbamate 4. Reduction of thiocarbamate 4 with tri-n-butyltin hydride provides a benzodiazepine 5.

Scheme 5

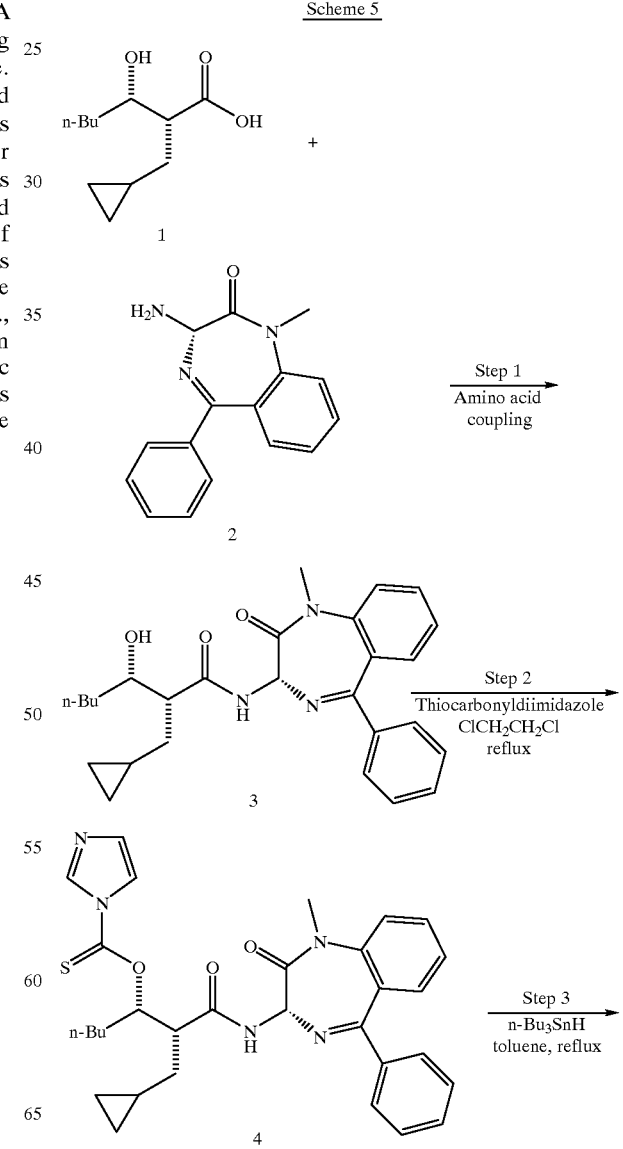

-continued

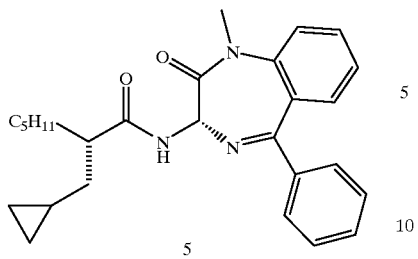

5

Alternatively, compounds of Formula (I) can be prepared according to Scheme 6. An acid XXI is coupled with a W-X-Y-Z-substituted aminolactam, XI, to give a compound of Formula (Ia) using methods commonly used in peptide syntheses, such as DCC, EDC, CDI, BOP, PyBOP, HATU, HBTU and phenyl ester mediated coupling, as described in A. R. Chamberlin, *Chem. Rev.* 1997, 97, 2243–2266. Subsequently, the amide nitrogen of compound (Ia) can optionally react with an $R^6$-LG to give a compound of Formula (I).

Scheme 6

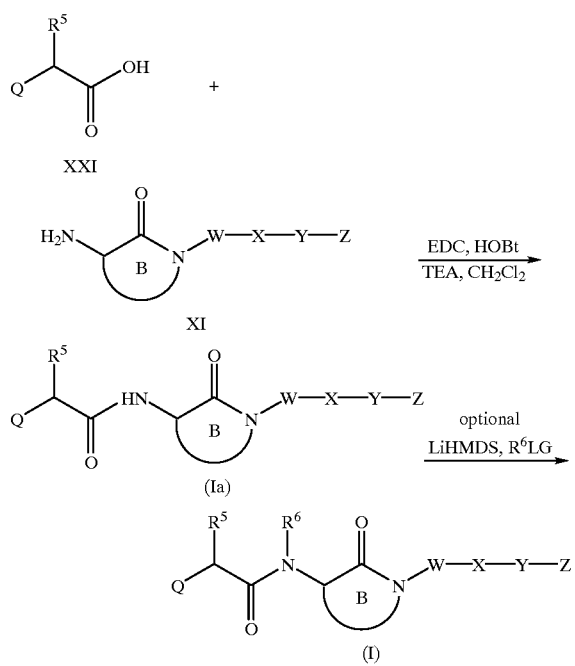

An example of the method of Scheme 6 is illustrated in the preparation of compound 7 (Scheme 7). Carboxylic acid of formula 6 (commercially available) is coupled with 3-amino-1,4-benzodiazepin-2-one 2 (Sherrill and Sugg, *J. Org. Chem.* 1995, 60, 730–734; Bock et al., *J. Med. Chem.*, 1993, 36, 4276–4292) in the presence of EDC and HOBt to give compound 7 (S. Nozaki et al, *Bull. Chem. Soc. Jpn.* 1982, 55, 2165–2168). General methods for preparing compounds similar to compound 6 can be found in Evans, D. A., et al., *J. Am. Chem. Soc.* 1990, 112, 5290, Evans, D. A. *Aldrichimica Acta* 1982, 15, 23, and Ponpipom, M. M., Hagmann, W. K. *Tetrahedron* 1999, 55, 6749.

Scheme 7

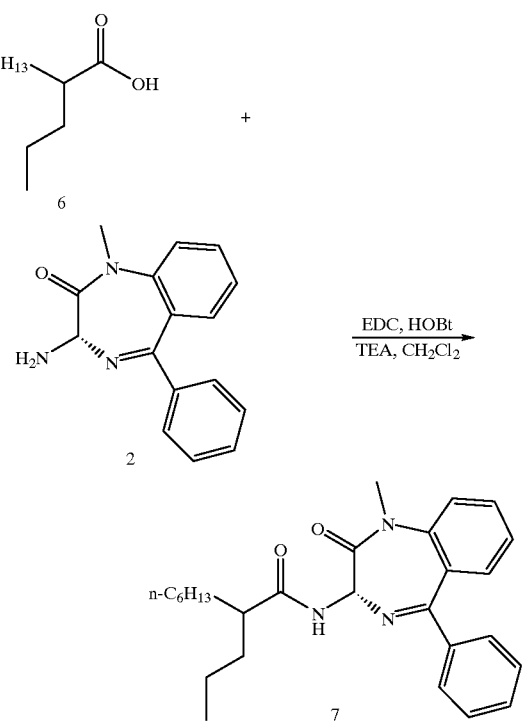

Another example of the method of Scheme 6 is illustrated in the preparation of compound 12 (Scheme 8). In step 3', a chiral lactic acid derivative 10 is coupled with 7-amino-6, 7-dihydro-5-methyl-6-oxo-5H-dibenz[b,d]azepin 11 in the presence of HOBt and EDC to afford compound 12.

Compound 11 can be prepared by the methods describe in PCT patent application WO 99/32453. The chiral lactic acid derivative 10 is prepared from bis-alkylation of (2S)-2-hydroxy-4-methylpentanoic acid 8 with iodopentane to give the lactate 9 in step 1'. Subsequent hydrolysis of lactate 9 using LIOH in THF/H$_2$O affords the chiral lactic acid derivative 10 in step 2'. Alternatively, compound 10 and other similar chiral lactic acid derivatives can be prepared by the methods described in *J.Org. Chem.*, 1986,51, 2402, and *Chem.Rev.*, 1992,92, 919.

Scheme 8

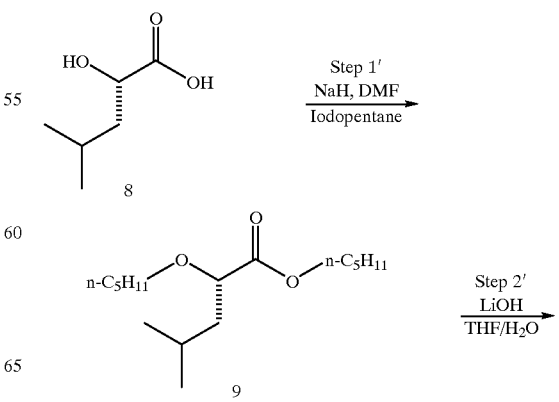

-continued

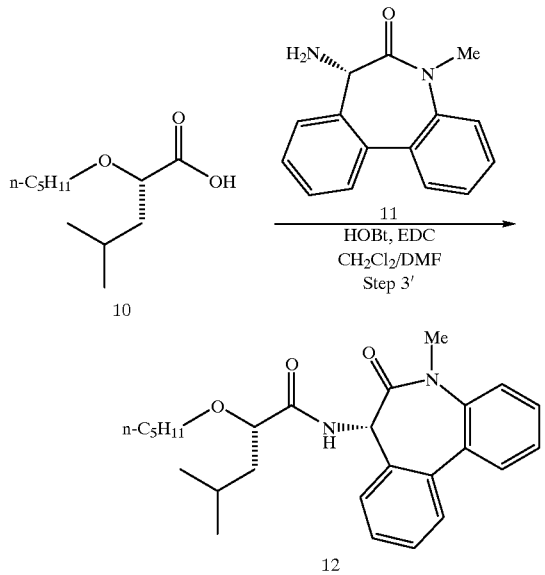

EXAMPLES

Chemical abbreviations used in the Examples are defined as follows: "DMPU" for 1,3-dimethyl-3,4,5,6-tetrahydro-2 (1H)-pyrimidone, "TBTU" for O-(1H-benzotriazol-1-yl)-N,N,N',N'-tetramethyluronium tetrafluoroborate, "BOP" for benzotriazol-1-yloxytris-(dimethylamino)-phosphonium hexafluorophosphate, "NMM" for N-methylmorpholine, "EDC" for 1-(3-dimethylaminopropyl)-3-ethylcarbodiimide hydrochlordie, "HOBt" for 1-hydroxybenzotriazole hydrate, "TEA" for triethyl amine, "LiHMDS" for lithium bis (trimethylsilyl)amide, "HMPA" for hexamethylphosphoramide, "LDA" for lithium diisopropylamide, "DCC" for 1,3-dicyclohexylcarbodiimide, "PyBoP" for benzotriazole-1-yl-oxy-tris-pyrrolidino-phosphonium hexafluorophosphate, and "HATU" for O-(7-azabenzotriazol-1-yl)-N,N,N',N'-tetramethyluronium hexafluorophosphate. "HPLC" is an abbreviation used herein for high pressure liquid chromatography.

Compounds of the present invention are generally purified by HPLC using conditions known to one skilled in the art. If necessary, organic layers can be dried over sodium sulfate unless otherwise indicated. However, unless otherwise indicated, the following conditions are generally applicable.

HPLC Condition A

Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid).

HPLC Condition B

Alternatively, reverse-phase HPLC can be carried out using a Vydac C-18 column with gradient elution from 10% to 90% acetonitrile in water.

Example 1

(3S)-3-[(1-oxo-(2S)-2-cyclopropylmethyl-heptyl)]amino-1-methyl-5-phenyl-2,3-dihydro-1H-1,4-benzodiazepin-2-one

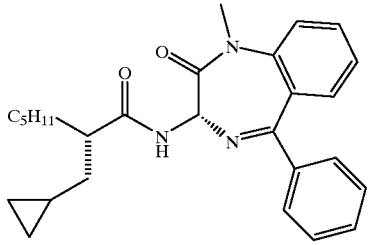

Step 1: Preparation of compound 3(S)-[(1-oxo-(2R)-2-cyclopropylmethyl-(3S)-3-hydroxy-heptyl)]amino-1-methyl-5-phenyl-2,3-dihydro-1H-1,4-benzodiazepin-2-one, 3. Compound 2 (Scheme 5) was prepared according to the method described in 1) Sherrill and Sugg, J. Org. Chem. 1995, 60, 730–734; 2) Bock et al., J. Med. Chem., 1993, 36, 4276–4292; and 3) Paul J. Reider et al J. Org. Chem. 1987, 52, 955. Compound 1 was prepared by the procedure of Evans D. A. Evans et al, Org. Synth. 1990, 68, 83–90 (See Scheme 2, Q' is n-Bu and $R^5$ is cyclopropylmethyl). A mixture of acid 1 (100 mg, 0.500 mmol) and a camphor-sulphonate salt of compound 2 (249 mg, 0.500 mmol) in 2 mL of methylene chloride was stirred at 0° C. 1-Hydroxybenzotriazole hydrate (81 mg, 0.60 mmol), 1-[3-(dimethylamino)propyl]-3-ethylcarbodiimide hydrochloride (192 mg, 1.00 mmol) and triethylamine (0.29 mL, 2.1 mmol) were added sequentially. After the mixture was stirred for 16 h, 30 mL of ethyl acetate was added. The organic layer was washed with 5% $NaHCO_3$ (30 mL) and brine (30 mL), dried over anhydrous magnesium sulfate and concentrated under reduced pressure. Purification by flash column chromatography (50% ethyl acetate-hexane) afforded 130 mg (58%) of product 3; MS (ESI): 448 (M+H), 470 (M+Na), 446 (M–H). Step 2: Preparation of 3(S)-[((2R)-2-cyclopropylmethyl-(3S)-3-((1-imidazolylthionyl)oxy)-1-oxoheptyl)]amino-1-methyl-5-phenyl-2,3-dihydro-1H-1,4-benzodiazepin-2-one, 4. Compound 3 (224 mg, 0.500 mmol), from step 1, and 1,1'-(thiocarbonyl)-diimidazole (178 mg, 1.00 mmol) were refluxed in 5 mL of 1,2-dichloroethane under nitrogen for 30 h (Scheme 5). An additional portion of 1,1'-(thiocarbonyl) diimidazole (180 mg, 1.00 mmol) was added, and reflux was continued for an additional 30 h. 20 mL of ethyl acetate was added. The organic layer was washed with water (30 mL) and brine (30 mL), dried over anhydrous magnesium sulfate and concentrated under reduced pressure. Purification by flash chromatography (60% ethyl acetate-hexane) afforded 198 mg (71%) of 4 as a colorless gel. $^1H$ NMR (300 MHz, $CDCl_3$) δ8.56 (1 H, br s), 7.82 (1 H, br s), 7.24–7.64 (10 H, m), 7.04 (1 H, br s), 5.96 (1 H, m), 5.54 (1 H, d, J=7.7 Hz), 3.47 (3 H, s), 2.97 (1 H, m), 1.86–1.06 (3 H, m), 1.24–1.45 (5 H, m), 0.94 (3 H, t, J=6.6 Hz), 0.81 (1 H, m), 0.50 (2 H, m), 0.13 (1 H, m), 0.06 (1 H, m); MS (APCI): 558 (M+H), 592 (M+Cl).

Step 3: Preparation of (3S)-3-[(1-oxo-(2R)-2-cyclopropylmethyl-heptyl)]amino-1-methyl-5-phenyl-2,3-dihydro-1H-1,4-benzodiazepin-2-one, 5. A solution of 4 (190 mg, 0.350 mmol), from step 2, in 10 mL of dry and degassed toluene was heated to reflux. A solution of tri-n-butyltin hydride (210 mg, 0.700 mmol) in 1 mL of toluene was added dropwise over 30 min. After an additional 5 h of reflux, the reaction was cooled, concentrated under reduced pressure. The crude mixture was purified by flash chromatography (elution with hexanes initially to remove tin-containing materials, then with 40% ethyl acetate-hexane) to afford 128 mg (85%) of compound 5 as a colorless gel. $^1$H NMR (300 MHz, CDCl$_3$) δ7.21–7.66 (10 H, m), 5.60 (1 H, d, J=8.4 Hz), 3.47 (3 H, s), 2.30 (1 H, m), 1.21–1.84 (10 H, m), 0.91 (3 H, t, J=6.2 Hz), 0.76 (1 H, m), 0.46 (2 H, m), 0.06 (2 H, m); MS (ESI): 432 (M+H), 455 (M+Na), 430 (M−H).

Example 2

(3S)-3-[(1-oxo-2-propyloctyl)]amino-1-methyl-5-phenyl-2,3-dihydro-1H-1,4-benzodiazepin-2-one

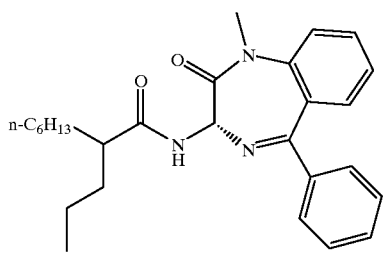

In accordance with Scheme 7, a mixture of acid 6 (186 mg, 1.00 mmol) and the (+)-camphorsulfonate salt of 3-(S)-amino-1-methyl-5-phenyl-2,3-dihydro-1H-1,4-benzodiazepin-2-one, 2, (Paul J. Reider et al J. Org. Chem. 1987, 52, 955) (497 mg, 1.00 mmol) in 2 mL of methylene chloride was stirred at 0° C. 1-[3-(dimethylamino)propyl]-3-ethylcarbodiimide hydrochloride (383 mg, 2.00 mmol) and triethylamine (0.17 mL, 1.2 mmol) were added sequentially (Scheme 7). After the mixture was stirred for 16 h, 30 mL of ethyl acetate was added. The organic layer was washed with saturated aqueous Na$_2$CO$_3$ (30 mL) and brine (30 mL), dried over anhydrous magnesium sulfate and concentrated under reduced pressure. Purification by chromatotron (Harrison Research, Model 8924) (15% ethyl acetate-hexane) afforded two diastereomers 7a and 7b. A: 90 mg (21%); $^1$H NMR (300 MHz, CDCl$_3$) δ7.20–7.65 (10 H, m), 5.58 (1 H, d, J=8.5 Hz), 3.47 (3 H, s), 2.28 (1 H, m), 1.20–1.80 (14 H, m), 0.96 (3 H, t, J=7.0 Hz), 0.87 (3 H, t, J=6.3 Hz); MS (ESI): 434 (M+H), 456 (M+Na), 432 (M−H); B: 96 mg (22%); $^1$H NMR (300 MHz, CDCl$_3$) δ7.20–7.65 (10 H, m), 5.59 (1 H, d, J=8.4 Hz), 3.47 (3 H, s), 2.28 (1 H, m), 1.20–1.80 (14 H, m), 0.91 (6 H, m); MS (ESI) 434 (M+H), 456 (M+Na), 432 (M−H).

Table 1 below provides representative Examples of the compounds of the present invention. The compounds of Table 1 were prepared by methods disclosed herein using appropriate reagents.

TABLE 1

| Example | Q | R5 | MS |
|---|---|---|---|
| 3 | n-heptyl | n-propyl | 448.3 (M + H) |
| 4 | n-hexyl | n-butyl | 470 (M + Na) |
| 5 | n-hexyl | methyl | 392.3 (M + H) |
| 6 | n-pentyl | n-pentyl | 448.3 (M + H) |
| 7 | n-propyl | n-propyl | 805.3 (2M + Na) |
| 8 | n-propyl | methyl | 364 (M + H) |

Example 3

(3S)-3-[(1-oxo-2-propylnonanyl)]amino-1-methyl-5-phenyl-2,3-dihydro-1H-1,4-benzodiazepin-2-one

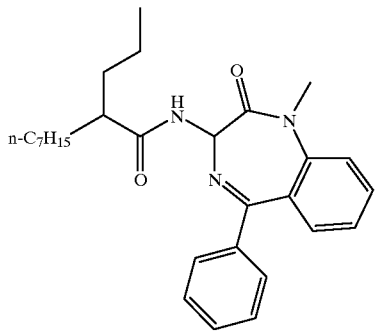

Example 4

(3S)-3-[(1-oxo-2-butyloctyl)]amino-1-methyl-5-phenyl-2,3-dihydro-1H-1,4-benzodiazepin-2-one

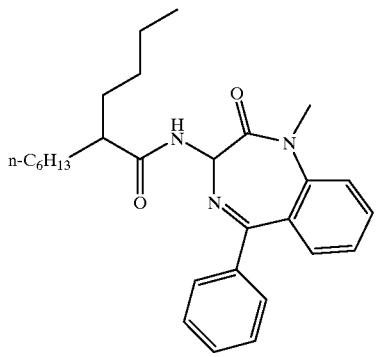

Example 5

(3S)-3-[(1-oxo-2-methyloctyl)]amino-1-methyl-5-phenyl-2,3-dihydro-1H-1,4-benzodiazepin-2-one

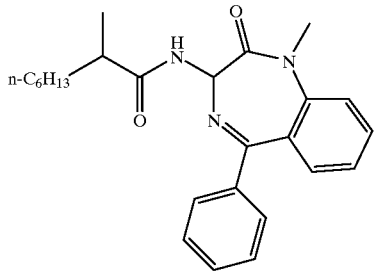

Example 6

(3S)-3-[(1-oxo-2-pentylheptanyl)]amino-1-methyl-5-phenyl-2,3-dihydro-1H-1,4-benzodiazepin-2-one

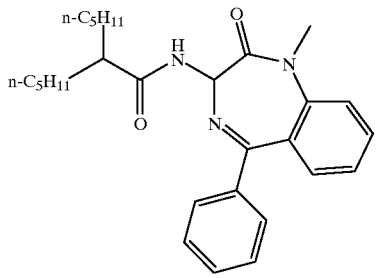

Example 7

(3S)-3-[(1-oxo-2-propylpentyl)]amino-1-methyl-5-phenyl-2,3-dihydro-1H-1,4-benzodiazepin-2-one

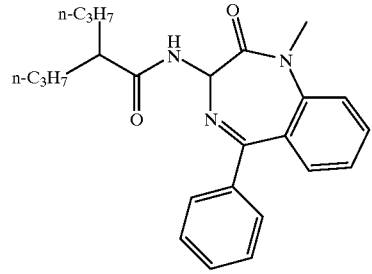

Example 8

(3S)-3-[(1-oxo-2-methylpentyl)amino]-1-methyl-5-phenyl-2,3-dihydro-1H-1,4-benzodiazepin-2-one

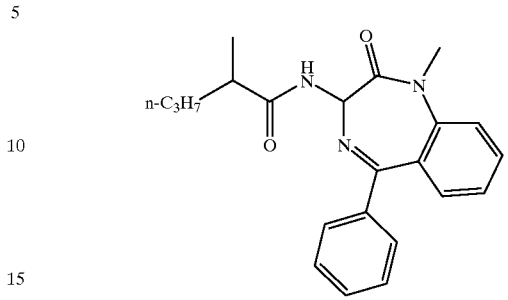

Example 9

(7S)-[(2S)-1-oxo-2-pentyloxy-4-methylpentyl]amino-5-methyl-5H,7H-dibenzo[b,d]azepin-6-one

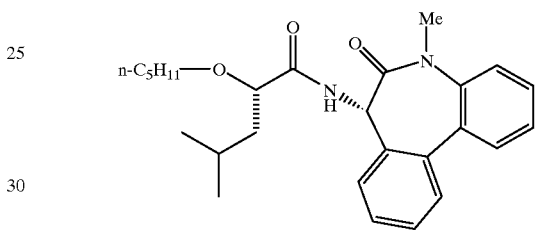

Step 1': Preparation of (2S)-pentyl 4-methyl-2-pentyloxypentanoate 9 (Scheme 8). To a solution of (2S)-2-hydroxy-4-methylpentanoic acid 8 (1 g, 7.6 mmol) in 50 mL DMF at 0° C. was added NaH (0.6 g, 15.2 mmol) and stirred for 20 min, followed by the addition of iodopentane (1.5 g, 7.6 mmol). The reaction mixture was stirred at rt for additional 16 h. The solution was poured into water and the layers separated. The aqueous layer was extracted with methylene chloride and the combined extracts were washed with sat'd NaHCO$_3$, dried over magnesium sulfate, and concentrated to a crude product. Upon further purification, compound 9 was obtained as an oil (80 mg, 4%). MS [M+H]$^+$ 273.

Step 2': Preparation of (2S)-4-methyl-2-pentyloxypentanoic acid 10. To a solution of (2S)-pentyl 4-methyl-2-pentyloxypentanoate 9 (80 mg, 0.3 mmol) in 20 mL of THF cooled to 0° C. was added dropwise a solution of lithium hydroxide monohydrate (25 mg, 0.6 mmol) in 5 mL of water. The reaction mixture was stirred at rt for 16 h. THF was removed under reduced pressure to give an yellow oil which was diluted with 10 mL of 1 N HCl. The aqueous phase was extracted with CH$_2$Cl$_2$ (8×15 mL), and the extracts were combined, dried over Na$_2$SO$_4$, and concentrated to afford compound 10 (45 mg, 74%). MS [M+H]$^+$ 203.

Step 3': Preparation of (7S)-[(2S)-1-oxo-2-pentyloxy-(4-methylpentyl)]amino-5-methyl-5H,7H-dibenzo[b,d]azepin-6-one, 12. To a solution of (2S)-4-methyl-2-pentyloxypentanoic acid 10 (45 mg, 0.22 mmol) in CH$_2$Cl$_2$/DMF (5:1, 15 mL) at 0° C. was added HOBT (40 mg, 0.26 mmol) and EDC (50 mg, 0.26 mmol). The mixture was stirred for 10 min then the amine 11 (52 mg, 0.22 mmol) was added and stirring was continued for 1 h. The solution was poured into water and the layers separated. The aqueous layer was extracted with methylene chloride and the combined extracts were washed with water, 1 N HCl, sat'd NaHCO₃, dried over magnesium sulfate, and concentrated to a glassy solid compound 12 (80 mg, 86%). MS [M+H]⁺ 423.

Example 10

3-[1-oxo-2-(S)-cyclopropylmethyl-heptyl]amino-1-methyl-5-(pyridin-2-yl)-2,3-dihydro-1H-1,4-benzodiazepine-2-one

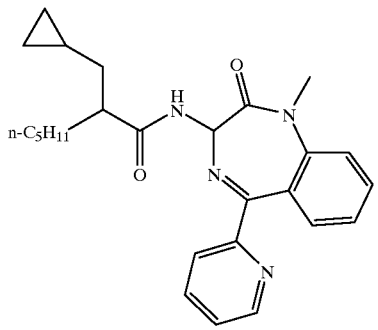

(±)-3-(2-(R)-Cyclopropylmethyl-3-(S)-hydroxyl-1-oxoheptyl)amino-1-methyl-5-(pyridin-2-yl)-2,3-dihydro-1H-1,4-benzodiazepin-2-one was made from 1 and 3-amino-1-methyl-5-(pyridin-2-yl)-2,3-dihydro-1H-1,4-benzodiazepine-2-one (G. Semple et al Synth. Commun. 1996, 26, 721) according to step 1 in Example 1. MS (ESI): 449 (M+H), 471 (M+Na), 447 (M–H). This diastereomeric mixture was submitted to chiral separation on a Chiralpak AD column with 10–15% i-propanol/hexane. The 2$^{nd}$ eluting peak was converted to Example 10 by the same procedures of steps 2 and 3 in Example 1. MS (ESI): 433.3 (M+H).

Example 11

3-[1-oxo-2-(S)-cyclopropylmethyl-heptyl]amino-1-methyl-5-[4-methyl(pyridin-2-yl)]-2,3-dihydro-1H-1,4-benzodiazepin-2-one

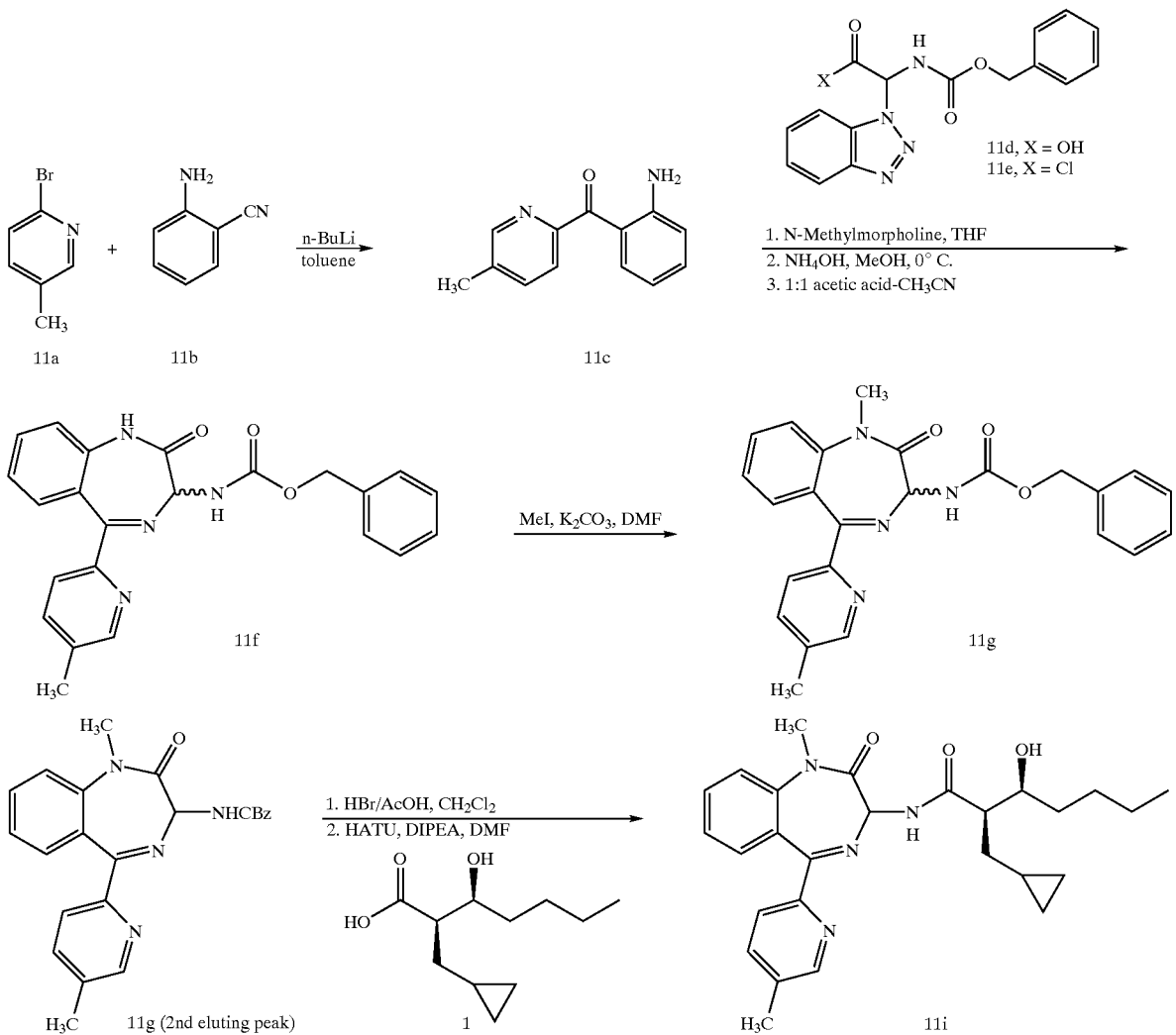

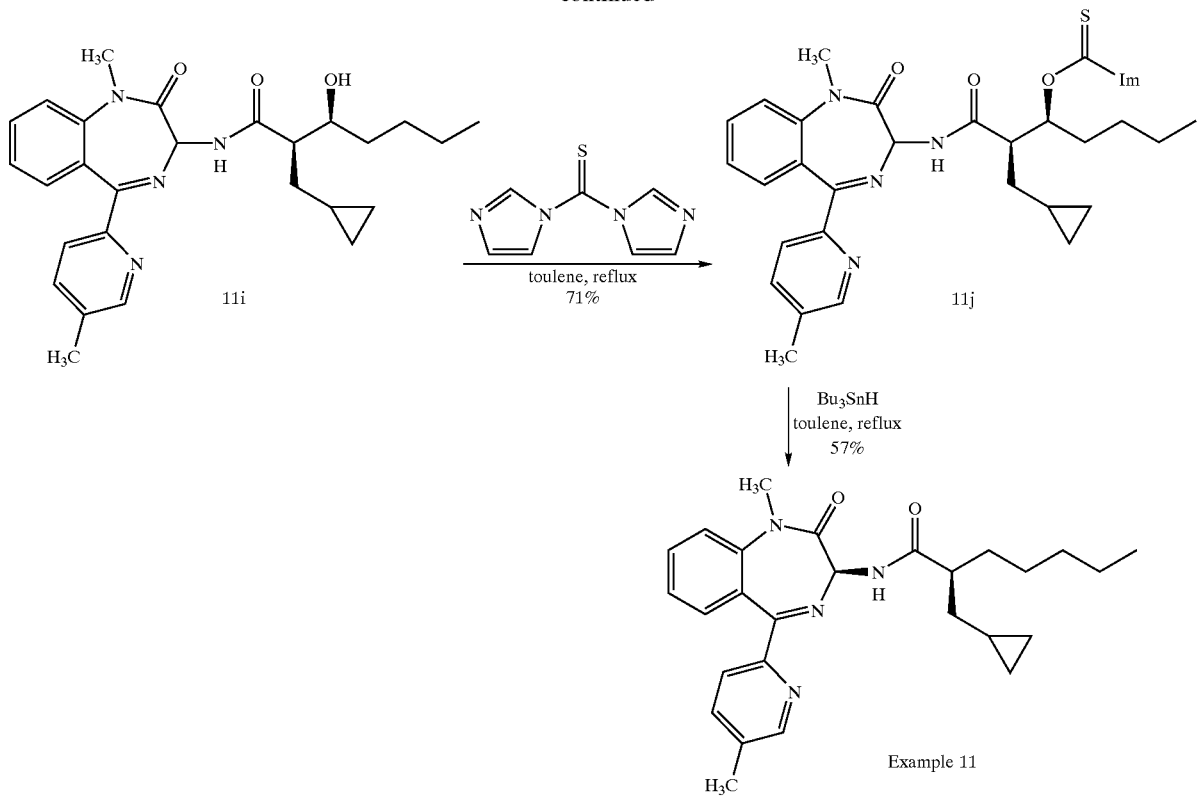

Example 11

Step 1: A solution of 2-bromo-5-picoline 11a (19.8 g, 115 mmol) and 2-cyanoaniline 11b (8 g, 68 mmol) in toluene (80 mL) was cooled to −40° C. and treated with 2.5 M n-BuLi (102 mL, 253 mmol). After the addition, the reaction was warmed to 0° C. and stirred for 4.5 h. The reaction mixture was poured into 3 N HCl (75 mL) and stirred for 15 min. The organic portion was separated and extracted with 3 N HCl (25 mL). The aqueous portions were washed with toluene (25 mL) and made basic by the addition of 25% NaOH. The aqueous layer was extracted with $CH_2Cl_2$ (3×100 mL). The organic layers were combined and dried over $MgSO_4$. The solids were filtered and the solvent was removed under reduced pressure to afford 1ic as a dark red oil (4.8 g, 30%). $^1$H NMR (500 MHz, $CDCl_3$) δ8.50 (m, 1 H), 7.70–7.60 (m, 3 H), 7.25 (m, 1 H), 6.70 (m, 1 H), 6.60 (m, 1 H), 6.20 (s, 2 H), 2.35 (s, 3 H).

Step 2: Acid 11d (21 g, 64 mmol) was dissolved in THF (190 mL) and cooled to 0° C. The solution was treated with catalytic DMF (0.25 mL) and oxalyl chloride (5.5 mL, 64 mmol). After 2 h, amine 11c (9 g, 42 mmol) and N-methylmorpholine (12 mL, 106 mmol) in THF (25 mL) were added slowly to the stirred reaction mixture. The reaction was warmed to rt and stirred for 12 h. The reaction was quenched by addition of $H_2O$ (200 mL). The aqueous layer was extracted with $CH_2Cl_2$ (200 mL). The organic layer was washed with sat. $NaHCO_3$ (100 mL) and dried over $MgSO_4$. The solids were filtered and the solvent was removed under reduced pressure. The crude material was purified by $SiO_2$ column chromatography eluting with 3:6.8:0.2 $Et_2O$—$CH_2Cl_2$-$Et_3N$. The intermediate (10 g, 19 mmol) was dissolved in $CH_3CN$ (130 mL) and cooled to 0° C. The solution was treated with $NH_3$ which was bubbled through the reaction vessel for 20 min. A yellow solid precipitated from the solution. The reaction was slowly warmed to rt and stirred for 6 h. The excess $NH_3$ and $CH_3CN$ was removed under reduced pressure. The solid material was transferred into a flask containing $CH_3CN$ (100 mL) and acetic acid (200 mL) and stirred for 12 h at rt. The solvent was removed under reduced pressure. The material was dissolved in $CH_2Cl_2$ and washed with 5% $NH_4OH$ in $H_2O$ (100 mL) and brine (100 mL). The organic layer was dried over $MgSO_4$ and filtered. The solvent was removed under reduced pressure. The crude material was dissolved in $CH_2Cl_2$ (35 mL) and $Et_2O$ (100 mL) was added via an addition funnel. A white solid precipitated from the solution. The solids were filtered and dried under reduced pressure to afford 11f as a white solid (5.4 g, 64% from 11c): $^1$H NMR (300 MHz, $CDCl_3$) δ8.40 (m, 1 H), 8.38 (m, 1 H), 7.96 (m, 1 H), 7.45–7.20 (m, 8 H), 7.15 (m, 1 H), 6.95 (m, 1 H), 5.35 (m, 1 H), 5.14 (m, 2 H), 2.39 (s, 3 H).

Step 3: A solution of intermediate 11f (5.4 g, 13.4 mmol) and finely ground $K_2CO_3$ (12.9 g, 94 mmol) in DMF (20 mL) was warmed to 50° C. To the solution was added MeI (1.3 mL, 20 mmol). After 2–3 h, the DMF was removed under reduced pressure. The crude material was dissolved in EtOAc (75 mL) and washed with $H_2O$ (3×50 mL) and brine (50 mL). The organic layer was dried over $MgSO_4$ and filtered. The solvent was removed under reduced pressure to afford 11g as a yellow solid (3.8 g, 68%): mp 157–158° C.; $^1$H NMR (500 MHz, $CDCl_3$) δ8.42 (m, 1 H), 8.05 (m, 1 H), 7.55 (m, 2 H), 7.43–7.20 (m, 8 H), 6.70 (m, 1 H), 5.36 (m, 1 H), 5.13 (m, 2 H), 3.42 (s, 3 H), 2.38 (s, 3 H); IR ($CH_2Cl_2$) 3054, 1726, 1682, 1499, 1266, 1069, 739, 704 $cm^{-1}$; FAB MS m/z=415 $[C_{24}H_{22}N_4O_3+H]^+$; HPLC 96.8% $t_r$=17.23 min. using HPLC condition A.

Step 4: (±)-11g was submitted to chiral separation on a CHIRALCEL OD column with 1/300/700 ratio of diethylamine/EtOH/$CO_2$. Only the $2^{nd}$ eluting peak was used in the next step.

Step 5: To a solution of the product of Step 4 (0.92 g, 2.2 mmol) in CH$_2$Cl$_2$ (11 mL) was added HBr (2.2 mL, 30% in acetic acid) and the reaction was stirred 4 h. The reaction was concentrated and azeotroped with toluene (4×15 mL) to obtain an orange solid. The crude reaction material was dissolved in DMF (20 mL) followed by addition of acid 1 (0.44 g, 2.2 mmol), HATU (0.84 g, 2.2 mmol) and diisopropylethylamine (1.9 mL, 11 mmol). After stirring for 14 h the reaction was quenched by addition of H$_2$O and ethyl acetate. The layers were separated and the aqueous layer was extracted with ethyl acetate (3×10 mL). The combined organic layers were dried over sodium sulfate and concentrated under reduced pressure. The crude raction was purified by column chromatography (ethyl acetate) to afford 11i (0.28 g, 29% for two steps) as a white solid: mp 84–102; $^1$H NMR (500 MHz, CD$_3$OD) δ8.36(d, J=1.4 Hz, 1 H), 7.93 (d, J=8.1 Hz, 1 H), 7.77 (m, 1 H), 7.65 (m, 1 H), 7.59 (m, 1 H), 7.28 (m, 2 H), 5.47 (s, 1 H), 3.65 (m, 1H), 3.45 (s, 3 H), 2.59 (m, 1 H), 2.41 (s, 3 H), 1.56–1.32 (m, 8 H), 0.92 (t, J=7 Hz, 3 H), 0.79 (m, 1 H), 0.43 (m, 2 H), 0.07 (m, 2H); IR (KBr) 3422, 2930, 1669, 1448 cm$^{-1}$; API MS m/z=463 [C$_{27}$H$_{34}$N$_4$O$_3$+H]; HPLC >95%, t$_r$=12.19 min. using HPLC condition A.

Step 6: To a solution of 11i (0.17 g, 0.4 mmol) in dichloroethane (5 ML) was added 1,1'-thiocarbonyldiimidazole (0.26 g, 1.5 mmol) in dichloroethane (2 mL) and the reaction was heated to 80° C. for 12 h. After cooling, the reaction was concentrated and purified by column chromatography (ethyl acetate) to afford 11j (0.17 g, 71%) as a pale yellow solid: $^1$H NMR (500 MHz, CD$_3$OD) δ8.52 (s, 1 H), 8.36 (s, 1H), 7.92 (d, J=8.1 Hz, 1 H), 7.84 (t, J=1.5 Hz, 1 H) 7.77 (m, 1 H), 7.65 (m, 1 H), 7.59 (m, 1 H), 7.30 (m, 2 H), 7.01 (s, 1H), 5.97 (m, 1H), 5.48 (s, 1 H), 3.45 (s, 3 H), 3.29 (m, 1H), 2.41 (s, 3 H), 2.01–1.79 (m, 3 H), 1.48–1.25 (m, 5 H), 0.91 (t, J=6.8 Hz, 3 H), 0.80 (m, 1 H), 0.44 (m, 2 H), 0.08 (m, 2H).

Step 7: A solution of 11j (0.17 g, 0.3 mmol) in toluene (5 mL) was heated to relux and then tributyltin hydride (0.13 mL, 0.5 mmol) in toluene (2 mL) was added dropwise. After 1 h the reaction was cooled and concentrated followed by column chromatography (hexanes, then 50:50 hexanes/ethyl acetate, then 5:95 methanol/methylene chloride) to afford Example 11 (0.075 g, 57%) as a white solid: mp 71–89° C.; $^1$H NMR (500 MHz, CD$_3$OD) * 8.38 (m, 1 H), 7.96 (d, J=8.1 Hz, 1 H), 7.77 (m, 1 H), 7.65 (m, 1 H), 7.59 (m, 1 H), 7.30 (m, 2 H), 5.49 (s, 1 H), 3.48 (s, 3 H), 2.62 (m, 1 H), 2.41 (s, 3 H), 1.56–1.32 (m, 11 H), 0.92 (m, 3 H), 0.79 (m, 1 H), 0.45 (m, 2 H), 0.08 (m, 2H); IR (KBr) 3423, 2928, 1664, 1498 cm$^{-1}$; ES MS m/z=447 [C$_{27}$H$_{34}$N$_4$O$_2$+H]; HPLC >95%, t$_r$=20.27 min. using HPLC condition A.

Example 12

3-[1-oxo-2-(S)-cyclopropylmethyl-heptyl]amino-1-methyl-5-[4-trifluoromethyl(pyridin-2-yl)]-2,3-dihydro-1H-1,4-benzodiazepin-2-one

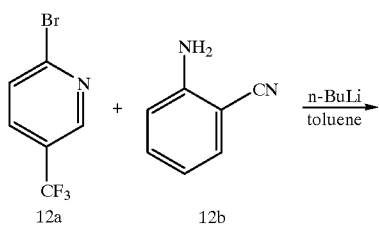

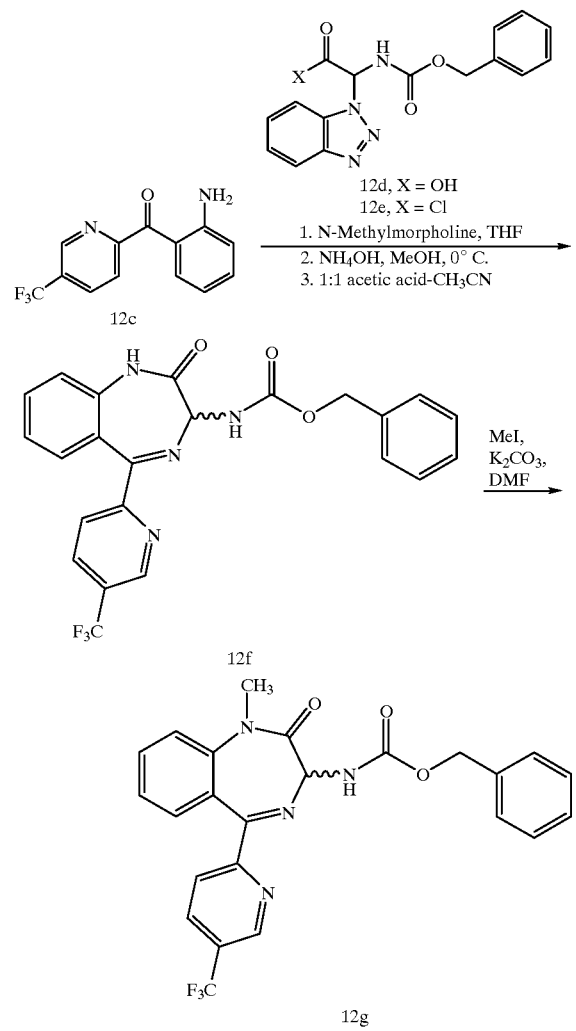

Step 1: 12c was prepared from 12a and 12b by the same method as shown for 11c. Compound 12c was isolated as a brown oil (6.6 g, 61%): $^1$H NMR δ8.95 (s, 1 H), 8.09 (m, 1 H), 7.85 (m, 1 H), 7.55 (m, 1 H), 7.30 (m, 1 H), 6.72 (m, 1 H), 6.61 (m, 1 H), 6.35 (m, 2 H).

Step 2: Acid 12d (13 g, 39 mmol) was dissolved in THF (100 mL) and cooled to 0° C. The solution was treated with catalytic DMF (0.25 mL) and oxalyl chloride (3.4 mL, 39 mmol). After 2 h, amine 12c (6.6 g, 26 mmol) and N-methylmorpholine (7.2 mL, 65 mmol) in THF (31 mL) were added slowly to the stirred reaction mixture. The reaction was warmed to rt and stirred for 12 h. The reaction was quenched by addition of H$_2$O (200 mL). The aqueous layer was extracted with CH$_2$Cl$_2$ (200 mL). The organic layer was washed with sat. NaHCO$_3$ (100 mL) and dried over MgSO$_4$. The solids were filtered and the solvent was removed under reduced pressure. The crude material was purified by SiO$_2$ column chromatography eluting with 1:4 Et$_2$O—CH$_2$Cl$_2$. The intermediate (7.8 g, 14 mmol) was dissolved in CH$_3$CN (95 mL) and cooled to 0° C. The solution was treated with NH$_3$, which was bubbled through the reaction vessel for 20 min. The reaction was slowly warmed to rt and stirred for 6 h. The excess NH$_3$ and CH$_3$CN was removed under reduced pressure. The solid material was dissolved in 1:2 CH$_3$CN-acetic acid (210 mL) and stirred for 12 h at rt. The solvent was removed under reduced pressure. The material was dissolved in $CH_2Cl_2$ and washed with 5% $NH_4OH$ in $H_2O$ (100 mL) and then brine (100 mL). The organic later was dried over $MgSO_4$ and filtered. The solvent was removed under reduced pressure. The crude material was purified by $SiO_2$ column chromatography eluting with 1:3 EtOAc-$CH_2Cl_2$ to provide the product as a dark blue amorphous solid. To the solid material was added 25% EtOAc-hexane. The solids were filtered to give 12f as a light blue solid (2.8 g, 44%): $^1$H NMR (300 MHz, $CDCl_3$) δ8.83 (m, 1 H), 8.25 (m, 1 H), 8.07 (s, 1 H), 8.04 (m, 1 H), 7.56 (m, 1 H), 7.42–7.22 (m, 6 H), 7.24 (m, 1 H), 7.13 (m, 1 H), 6.62 (m, 1 H), 5.45 (m, 1 H), 5.17 (m, 2 H).

Step 3: A solution of intermediate 12f (3.4 g, 7.6 mmol) and finely ground $K_2CO_3$ (7.3 g, 53 mmol) in DMF (11 mL) was warmed to 50° C. To the solution was added MeI (0.71 mL, 11 mmol). After 2–3 h, the DMF was removed under reduced pressure. The crude material was dissolved in EtOAc (250 mL) and washed with $H_2O$ (2×150 mL), 5% LiCl (50 mL) and brine (150 mL). The organic layer was dried over $MgSO_4$ and filtered. The solvent was removed under reduced pressure. The crude material was dissolved in 3 mL of $CH_2Cl_2$ and then diluted with 100 mL of 1:1 $Et_2O$-Hexane followed by 200 mL of hexane. The resulting solid was further purified by $SiO_2$ column chromatography eluting with 50:40:10 EtOAc-Hexane-THF to afford 12g as an off white solid (1.9 g, 55%): mp 179–180° C.; $^1$H NMR (500 MHz, $CDCl_3$) δ8.85 (s, 1 H), 8.32 (m, 1 H), 8.03 (m, 1 H), 7.60 (m, 1 H), 7.40–7.20 (m, 8 H), 6.74 (m, 1 H), 5.41 (m, 1 H), 5.15 (m, 2 H), 3.46 (s, 3 H); IR (KBr) 3422, 1723, 1687, 1604, 1498, 1324, 1131, 1079, 1016 $cm^{-1}$; CI MS m/z=469 $[C24H19F_3N_4O_3+H]^+$; HPLC>95% $t_r$=20.39 min. using HPLC condition A.

Step 4: (±)-Example 12 was submitted to chiral separation on a CHIRALPAK AD column with acetonitrile. Only the $1^{st}$ eluting peak was used in the next steps.

Using the product of step 4, the title compound was made according to the procedures in Steps 5, 6 and 7 of Example 11. MS (ESI): 501 (M+H).

Example 13

3-[1-oxo-2-(S)-aminomethyl-heptyl]amino-1-methyl-(5-trifluoromethyl-phenyl)-2,3-dihydro-1H-1,4-benzodiazepine-2-one hydrobromide

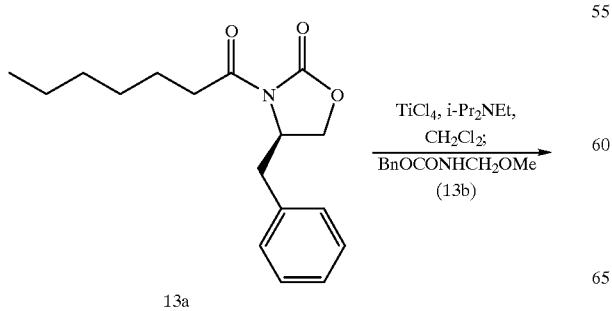

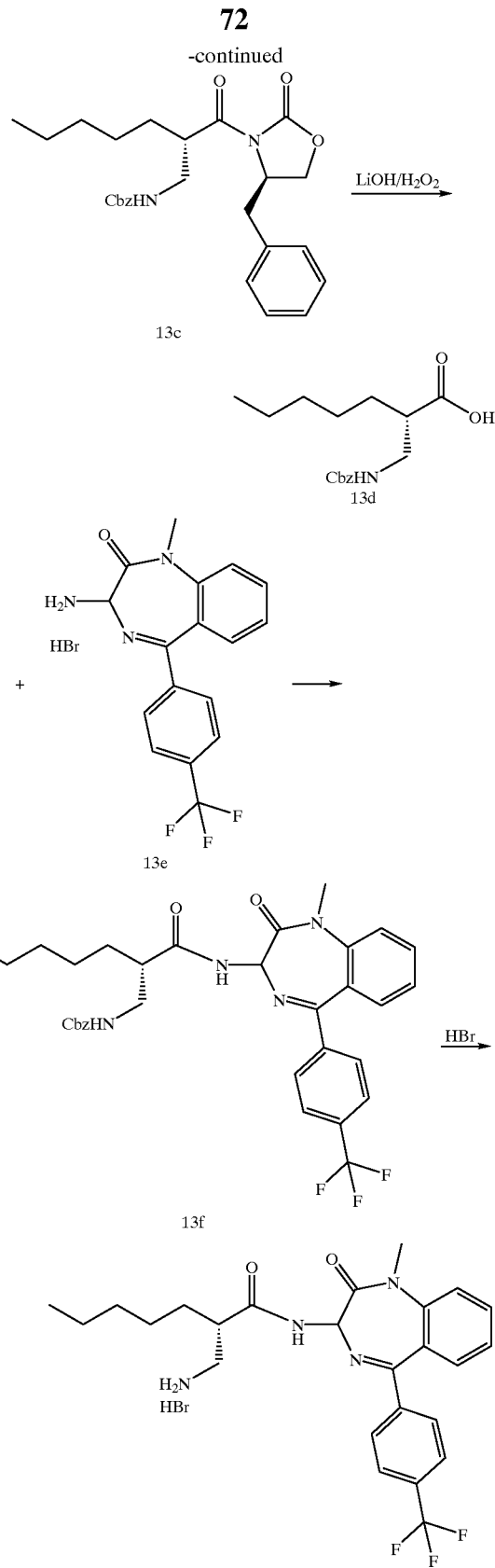

Step 1: 13a (1.07 g, 3.7 mmol) was dissolved in anhydrous $CH_2Cl_2$ (10 mL) and cooled to −60° C. $TiCl_4$ was added dropwise via a cannula to the above solution, followed by addition of diisopropylethylamine (0.68 mL, 3.9 mmol). After stirring for 1 h at −60° C., the resulting mixture was added a solution of N-methoxymethyl benzyl carbamate (13b, 0.94 g, 4.8 mmol) in CH$_2$Cl$_2$ (5 mL) via cannula. The reaction mixture was allowed to warm up to 0° C. in 1 h, quenched with saturated NH$_4$Cl (aq), and extracted with CH$_2$Cl$_2$ (3×20 mL). The extracts were combined, washed with NaHCO$_3$ (sat'd), brine, dried (MgSO$_4$), filtered, and concentrated. The residue was purified on silica gel, using 20% EtOAc-hexane, to afford 13c (690 mg, 41%) as a colorless oil. MS m/z 453.4 (MH$^+$).

Note: N-methoxymethyl benzyl carbamate was prepared according to C. J. Barnett et al Tetrahedron Lett. 1997, 38 (5), 735.
Titanium enolate used in the above reaction was generated according to D. A. Evans et al J. Am. Chem. Soc. 1990, 112, 8215.

Step 2: 13c (0.68 g, 1.5 mmol) was dissolved in THF (8 mL) and cooled to 0° C. H$_2$O$_2$ (1.6 mL, 15 mmol) and an aqueous solution of LiOH (2 mL, 1.5 M) were added dropwise to the above solution sequentially at a rate of keeping the internal temperature below 10° C. The resulting cloudy mixture was stirred at room temperature for 16 h, re-cooled to 0° C., and quenched with aqueous Na$_2$SO$_3$ (4 mL, 1.5 M). The mixture was stirred for an additional 1 h, concentrated in vacuo, and washed with CH$_2$Cl$_2$ (3×10 mL). The aqueous mixture was cooled in an ice-water bath, acidified to pH 2 with 6 N HCl, and extracted with EtOAc (3×10 mL). The extracts were combined, washed with brine, dried (Na$_2$SO$_4$), filtered, and concentrated in vacuo to give 13d (274 mg, 62%) as a white solid.

Step 4: 13d (270 mg, 0.92 mmol), 13e (Note, 381 mg, 0.92 mmol), 1-hydroxybenzotriazole hydrate (HOBT, 149 mg, 1.10 mmol) were suspended in CH$_2$Cl$_2$ (4 mL) and cooled to 0° C., 1-(3-dimethylaminopropyl)-3-ethylcarbodiimide hydrochloride (EDC HCl, 353 mg, 1.84 mmol) and triethylamine (0.26 mL, 1.84 mmol) were added subsequently. After stirring for 24 h at ambient temperature, the reaction mixture was diluted with EtOAc (20 mL), washed with water, brine, dried (Na$_2$SO$_4$), filtered, and concentrated in vacuo. The residue was purified on silica gel (50% EtOAc/hexane) to afford 13f (460 mg, 82%) as a white solid. MS m/z 609.5 (MH$^+$).

Note: (±)-13e, in Cbz protected form, was separated on a CHIRALPAK AD column with acetonitrile. Only the 1st eluting peak was converted, by the action of hydrogen bromide, to 3-amino-1-methyl-(5-trifluoromethyl-phenyl)-2,3-dihydro-1H-1,4-benzodiazepine-2-one hydrobromide (13e) used in the above reaction.

Step 5: 13f (200 mg, 0.33 mmol) was dissolved in a solution of HBr in AcOH (2 mL, 30%) and stirred for 2 h at room temperature. The resulting mixture was triturated with Et$_2$O. The precipitate was filtered under N$_2$, thoroughly washed with Et$_2$O, and dried overnight under high vacuum to afford Example 13 (154 mg, 84%) as a white solid. MS (ESI) m/z 475.5 (MH$^+$−HBr), 553.4 ((M−H)$^−$).

Example 14

3-[1-oxo-2-(S)-(dimethylamino)methyl-heptyl]amino-1-methyl-5-(trifluoromethyl-phenyl)-2,3-dihydro-1H-1,4-benzodiazepine-2-one

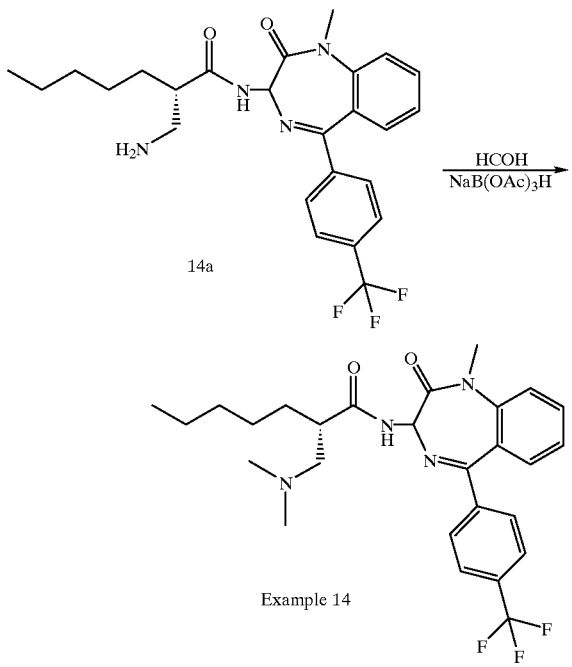

14a

Example 14

Formaldehyde (170 mg, 1.7 mmol, 37% aqueous solution) was added to a solution of 14a (free base of Example 13, 80 mg, 0.17 mmol) and NaBH(OAc)$_3$ (107 mg, 0.51 mmol) in dichloroethane (1 mL) at room temperature. The resulting mixture was then vigorously stirred overnight, and extracted with EtOAc (3×10 mL). The extracts were combined, washed with brine, dried (Na$_2$SO$_4$), filtered, and concentrated in vacuo. The residue was purified on silica gel (1:5:100 Et$_3$N—CH$_3$OH—CH$_2$Cl$_2$) to afford Example 14 (75 mg, 88%). $^1$H NMR (300 MHz, CDCl$_3$) δ0.86 (t, J=7 Hz, 3 H), 1.20–1.45 (m, 7 H), 1.65–1.75 (m, 1 H), 2.23 (dd, J=12, 4 Hz, 1 H), 2.32 (s, 6 H), 2.45–2.55 (m, 1 H), 2.72 (dd, J=12, 11 Hz, 1H), 3.43 (s, 3 H), 5.58 (d, J=8 Hz, 1 H), 7.18–7.35 (m, 3 H), 7.55–7.75 (m, 5 H), 9.21 (d, J=8 Hz, 1 H); MS (ESI) m/z 503.5 (MH$^+$).

Example 15

3-(3-isopentyloxy-2-(R)-methyl-1-oxo-propyl)amino-1-methyl-5-(trifluoromethyl)phneyl-2,3-dihydro-1H-1,4-benzodiazepin-2-one

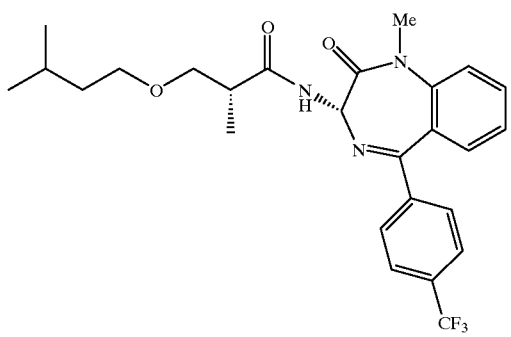

The compound of Example 15 was prepared by methods disclosed herein using appropriate reagents.

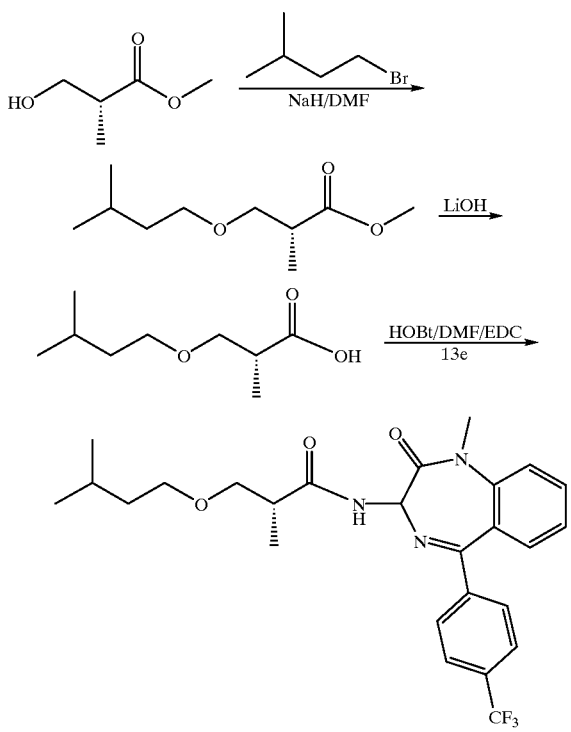

Example 15

The racemic 3-amino-1-methyl-(5-trifluoromethyl-phenyl)-2,3-dihydro-1H-1,4-benzodiazepine-2-one, in Cbz protected form, was separated on a CHIRALPAK AD column with acetonitrile. Only the 1$^{st}$ eluting peak was converted, by the action of hydrogen bromide, to an optically pure 3-amino-1-methyl-(5-trifluoromethyl-phenyl)-2,3-dihydro-1H-1,4-benzodiazepine-2-one hydrobromide, which was used in the preparation of the title compound. MS (M+1) 490.

Table 2 demonstrates representative compounds envisaged within the scope of the present invention. Each formulae at the start of Table 2 are intended to be paired with each entry in the table which follows.

For example the compound (7S)-[(1-oxo-(2R)-2-methylpropyl-5-hexenyl)]-amino-5-methyl-5H,7H-dibenzo[b,d]azepin-6-one is represented by Example #500-B-j, which comprises the core B, side chain j, and entry #500.

For example the compound (3R)-[(1-oxo-(2S)-2-dimethylpropyl-5-pentenyl)]amino-7-chloro-1-methyl-5-phenyl-1,3-dihydro-benzo[e][1,4]diazepin-2-one is represented by Example #502-D-ab, which comprises the core D, side chain ab, and entry #502.

TABLE 2

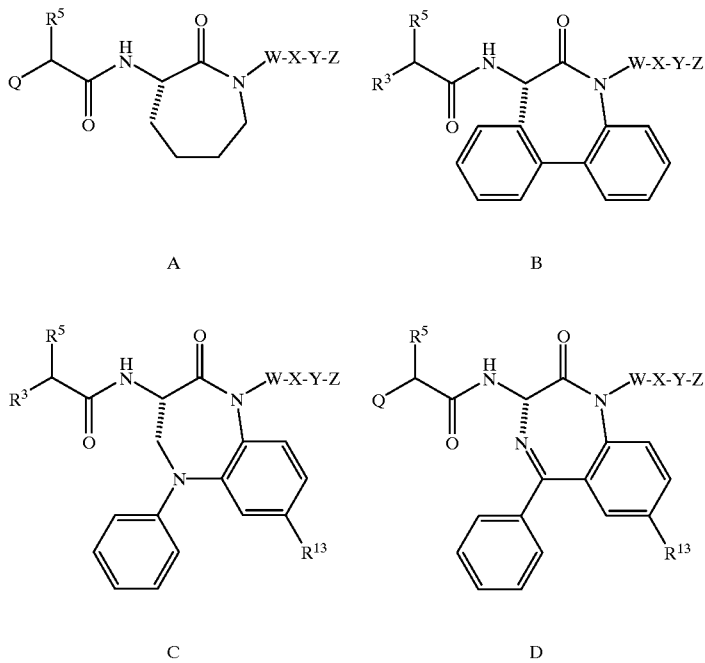

TABLE 2-continued
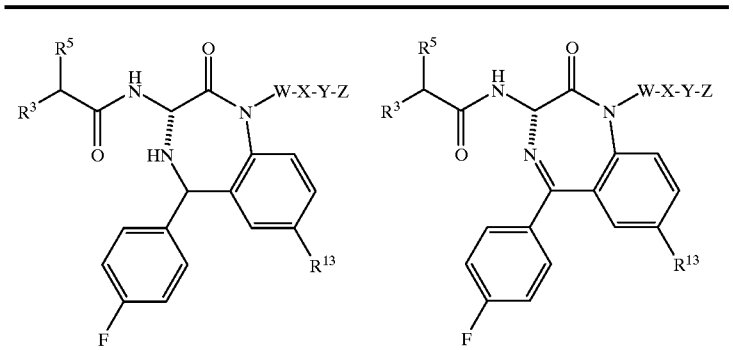
E  F
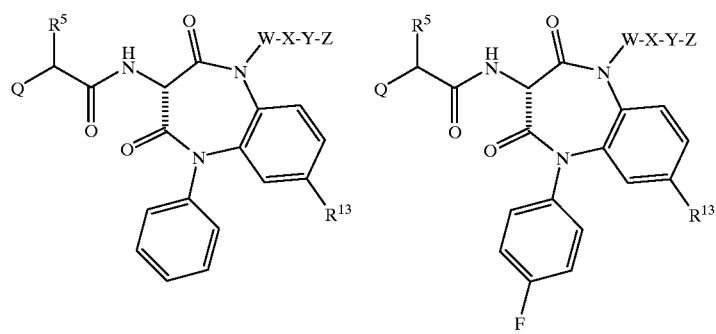
G  H
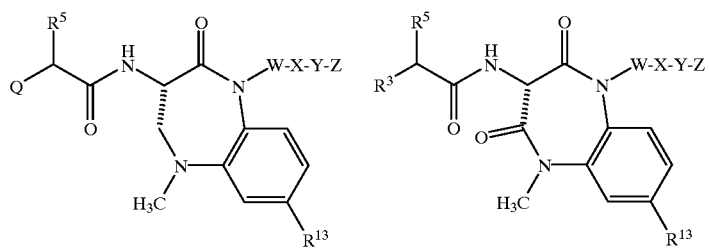
J  K
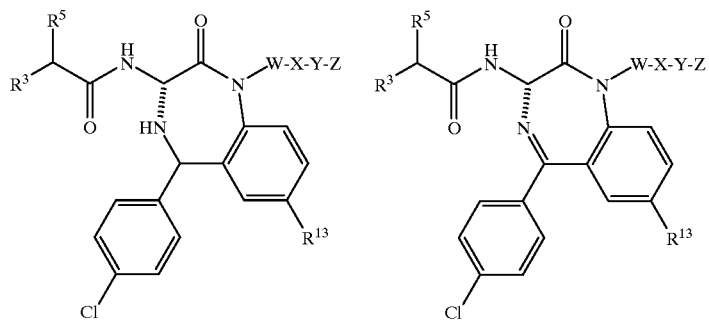
L  M TABLE 2-continued
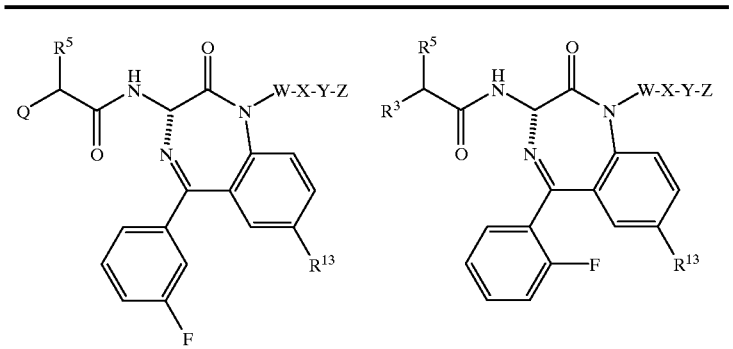
N                O
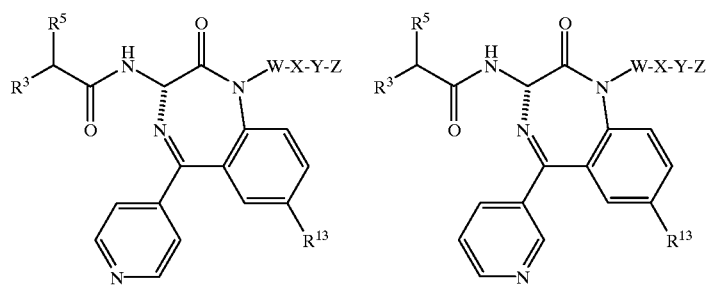
P                Q
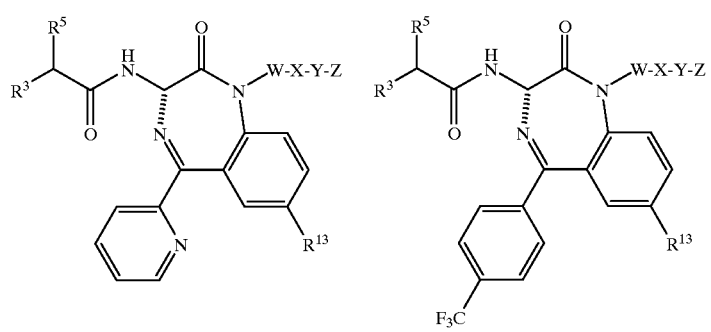
R                S
wherein Q and R$^5$ are described, respectively, in the following moieties:
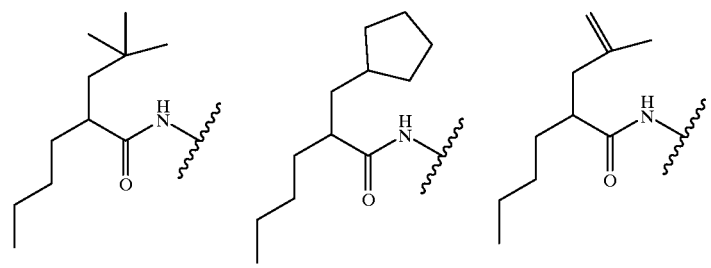
a          b          c TABLE 2-continued
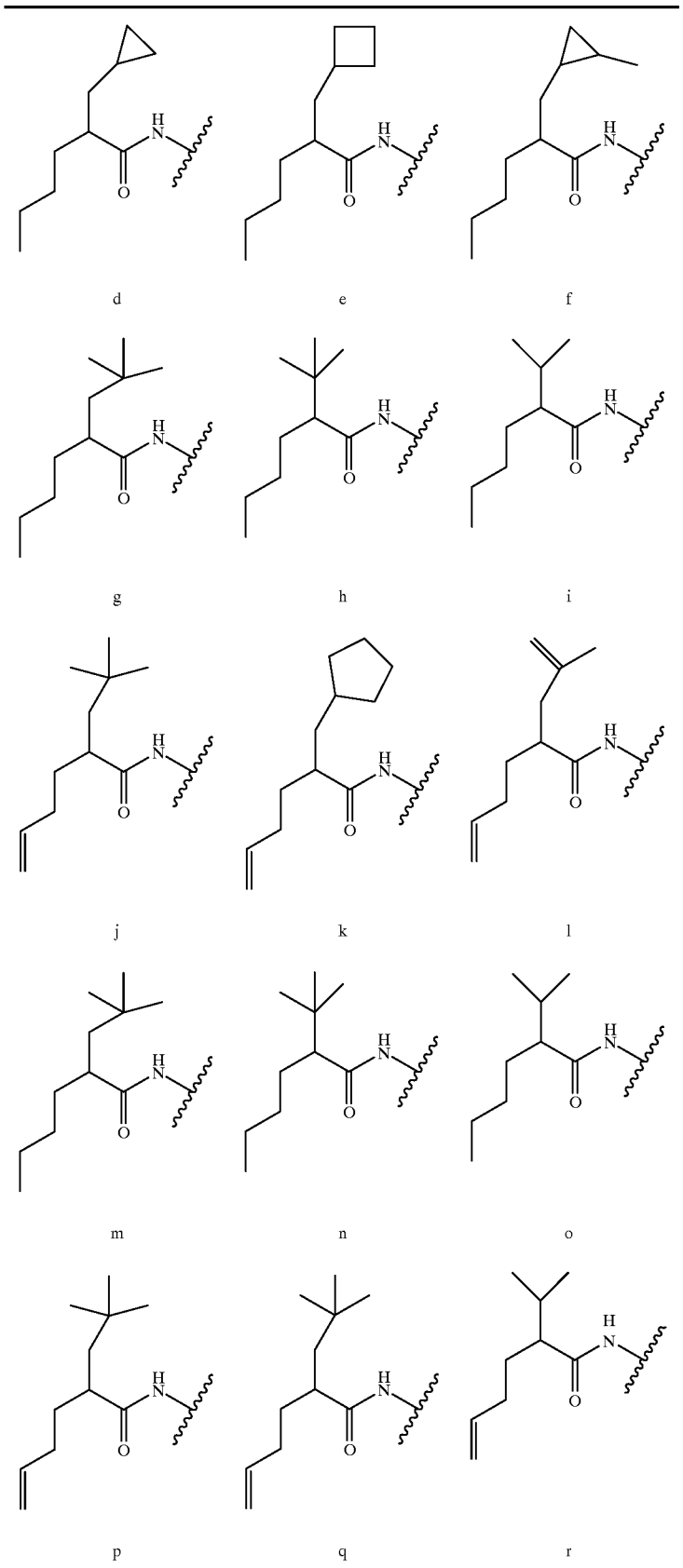

TABLE 2-continued
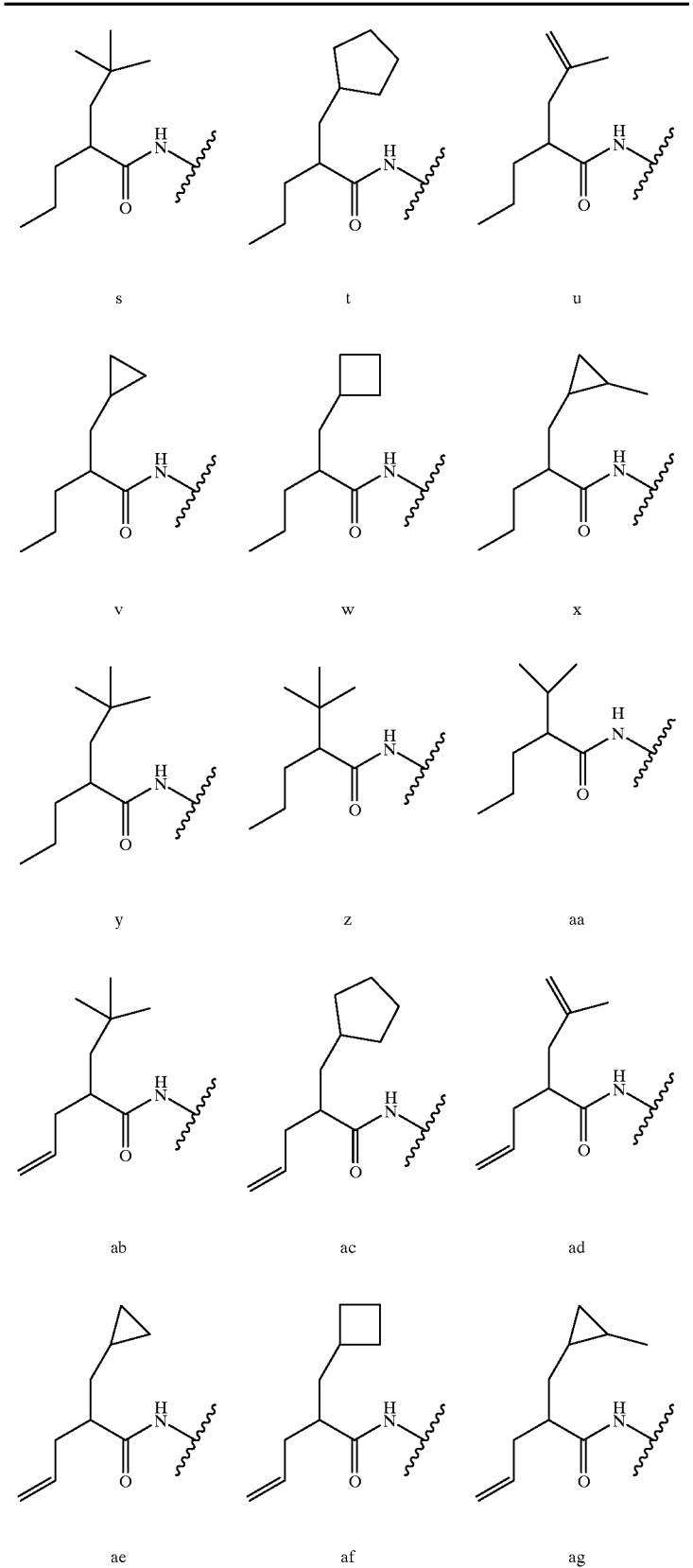

TABLE 2-continued
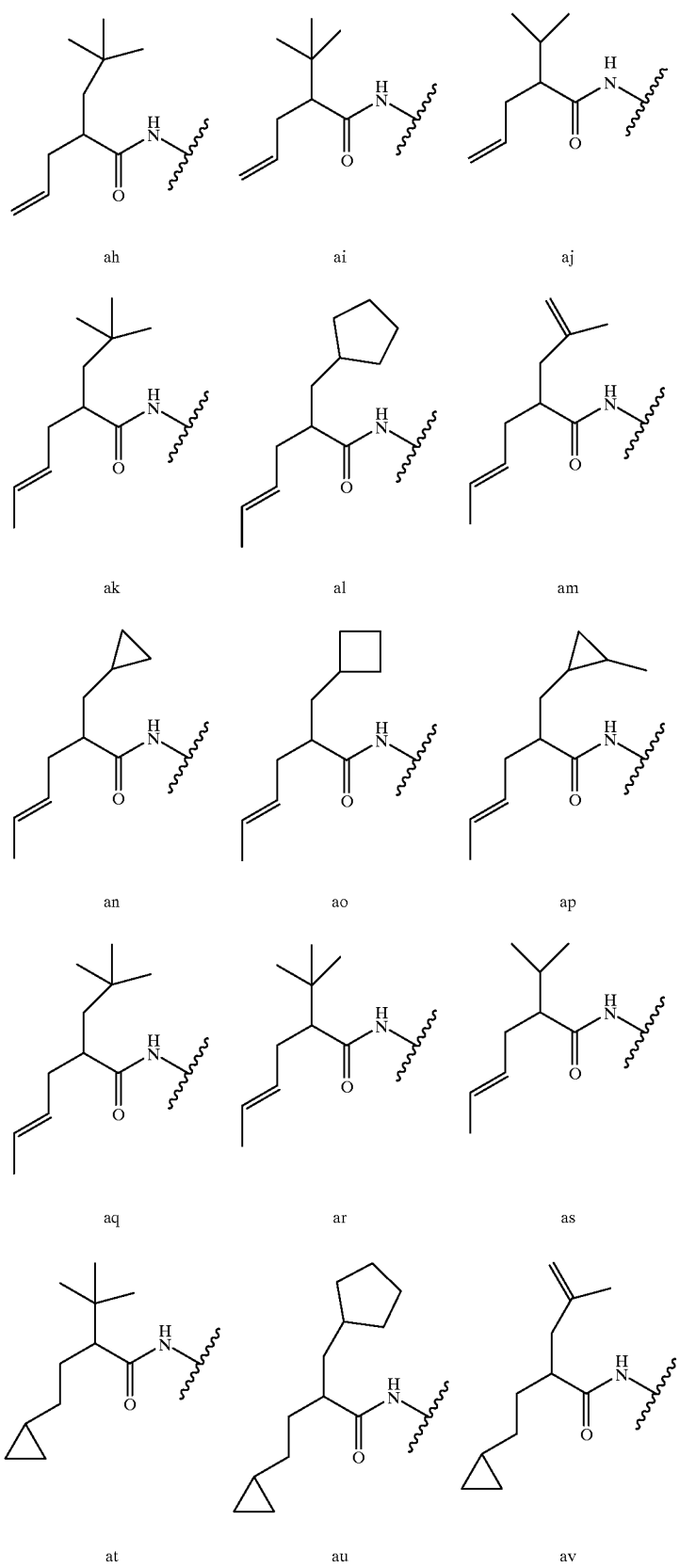

TABLE 2-continued
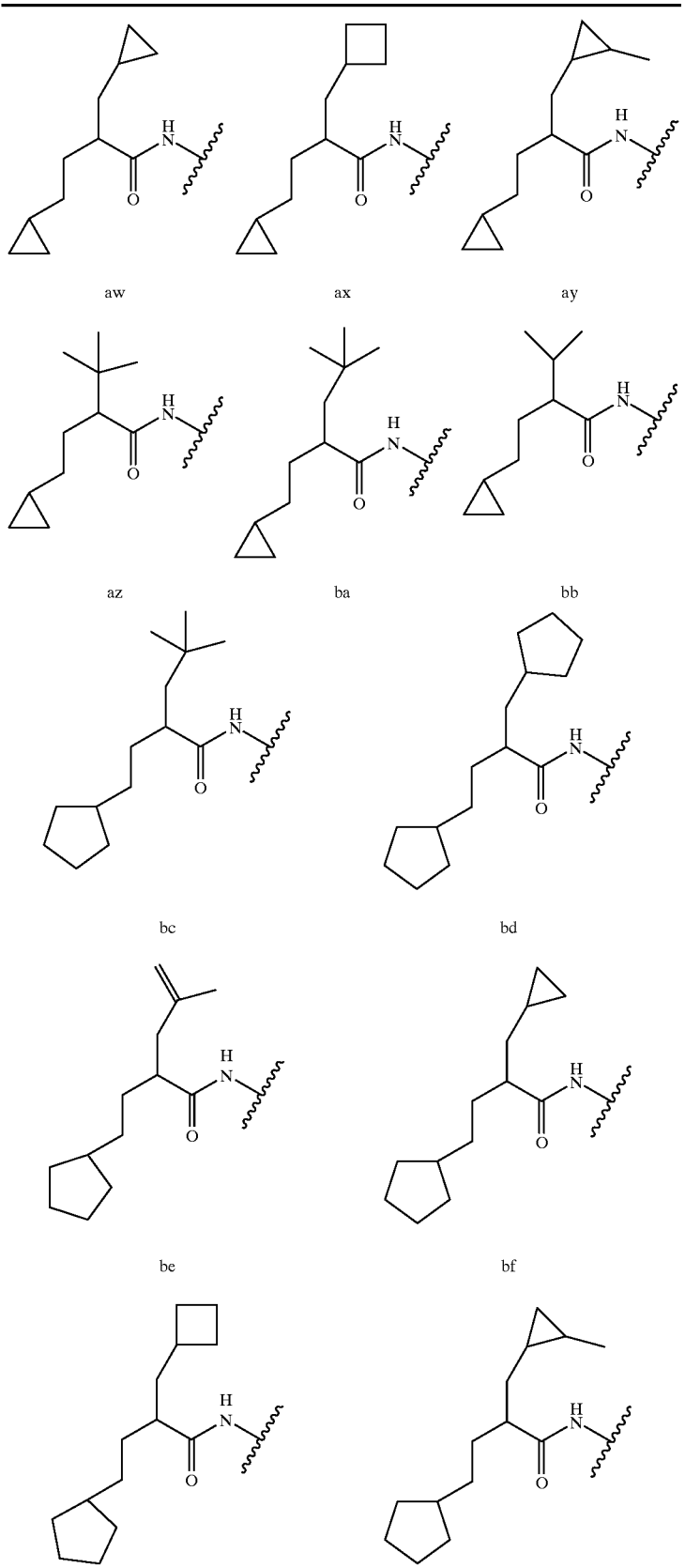

TABLE 2-continued
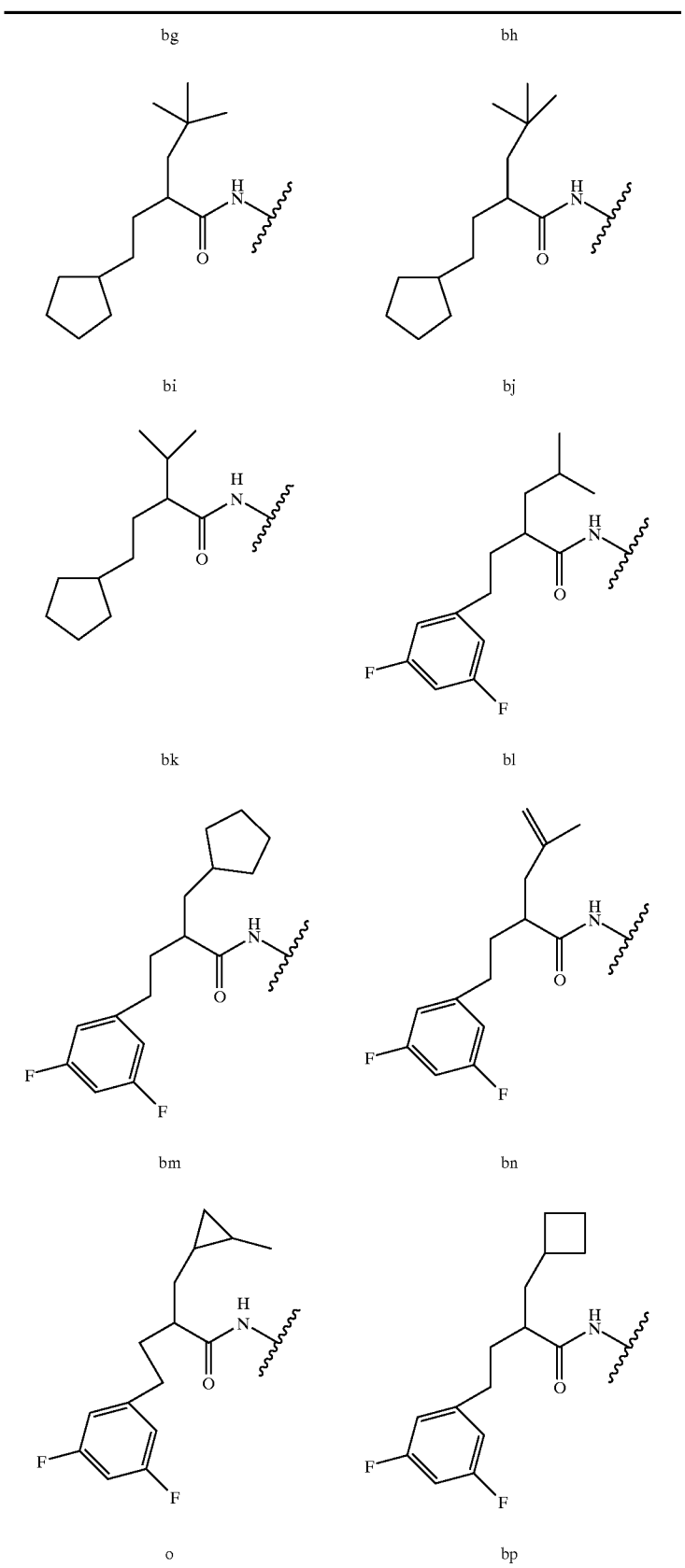

TABLE 2-continued
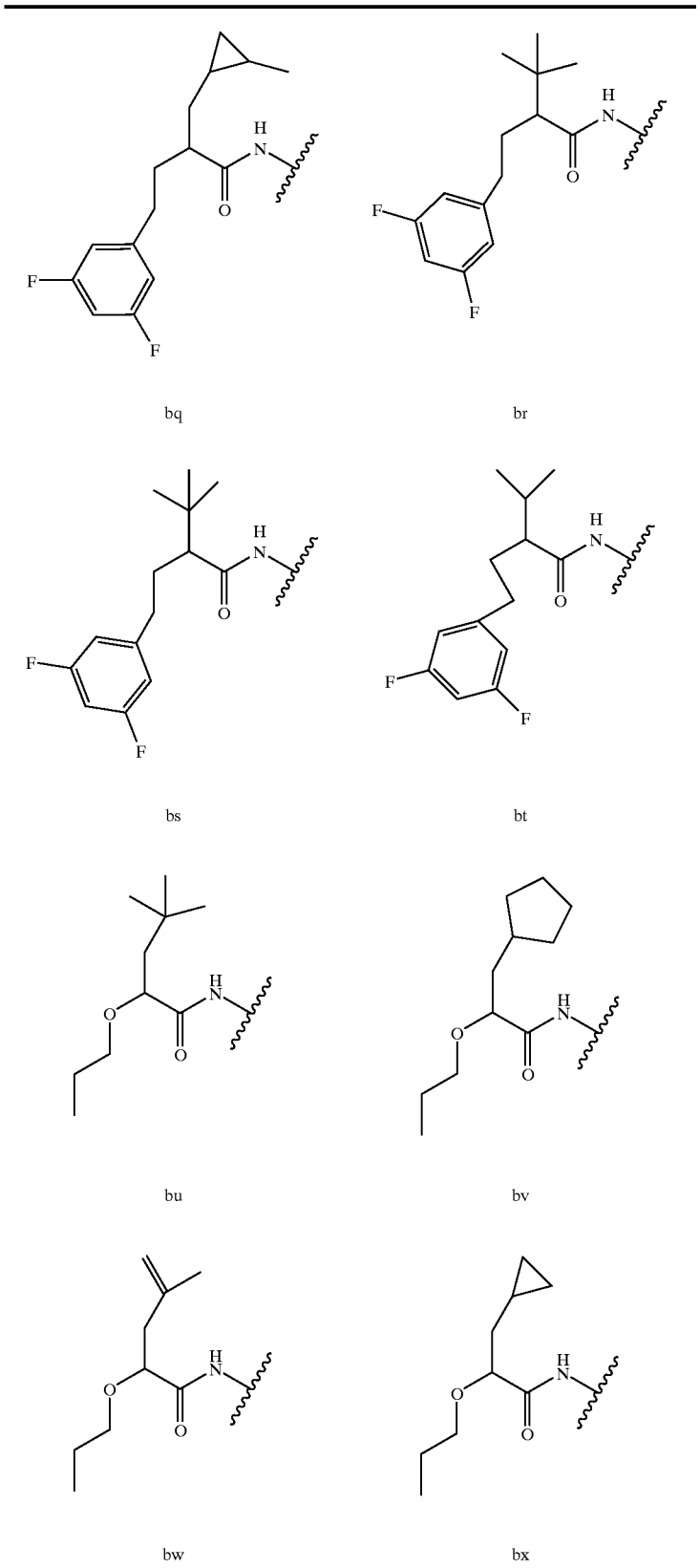

TABLE 2-continued
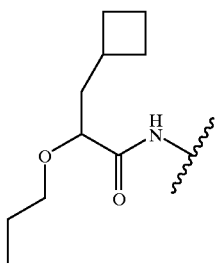
by
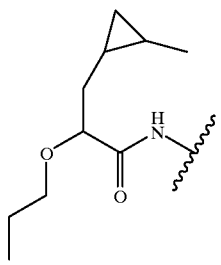
bz
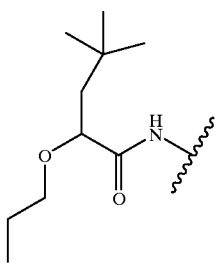
ca
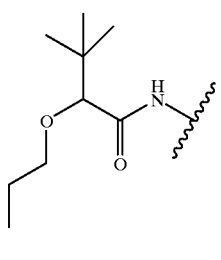
cb
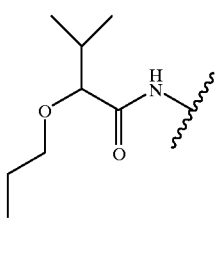
cc
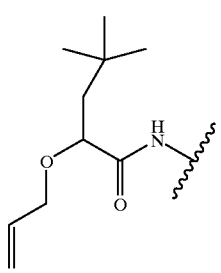
cd
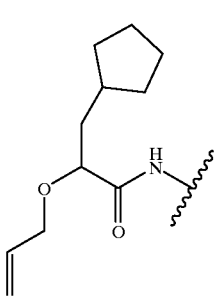
ce
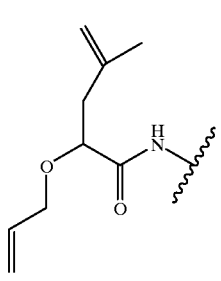
cf
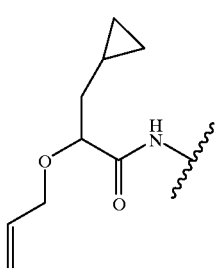
cg
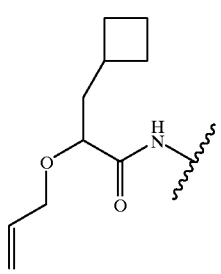
ch TABLE 2-continued
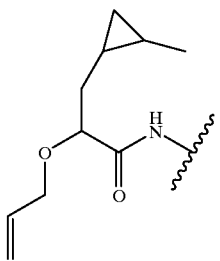
ci
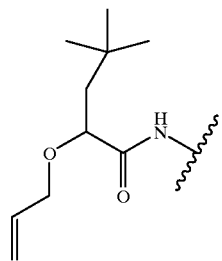
cj
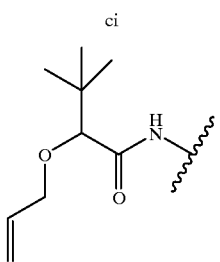
ck
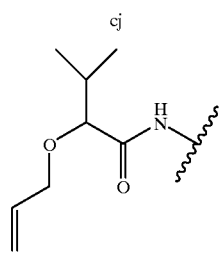
cl
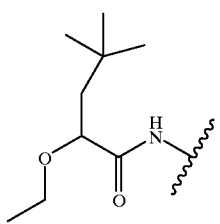
cm
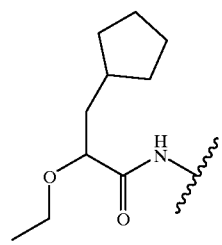
cn
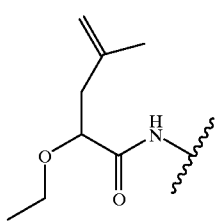
co
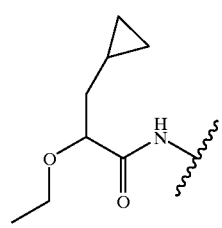
cp
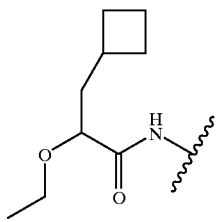
cq
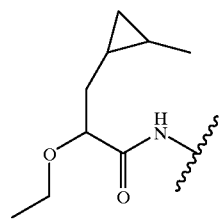
cr TABLE 2-continued
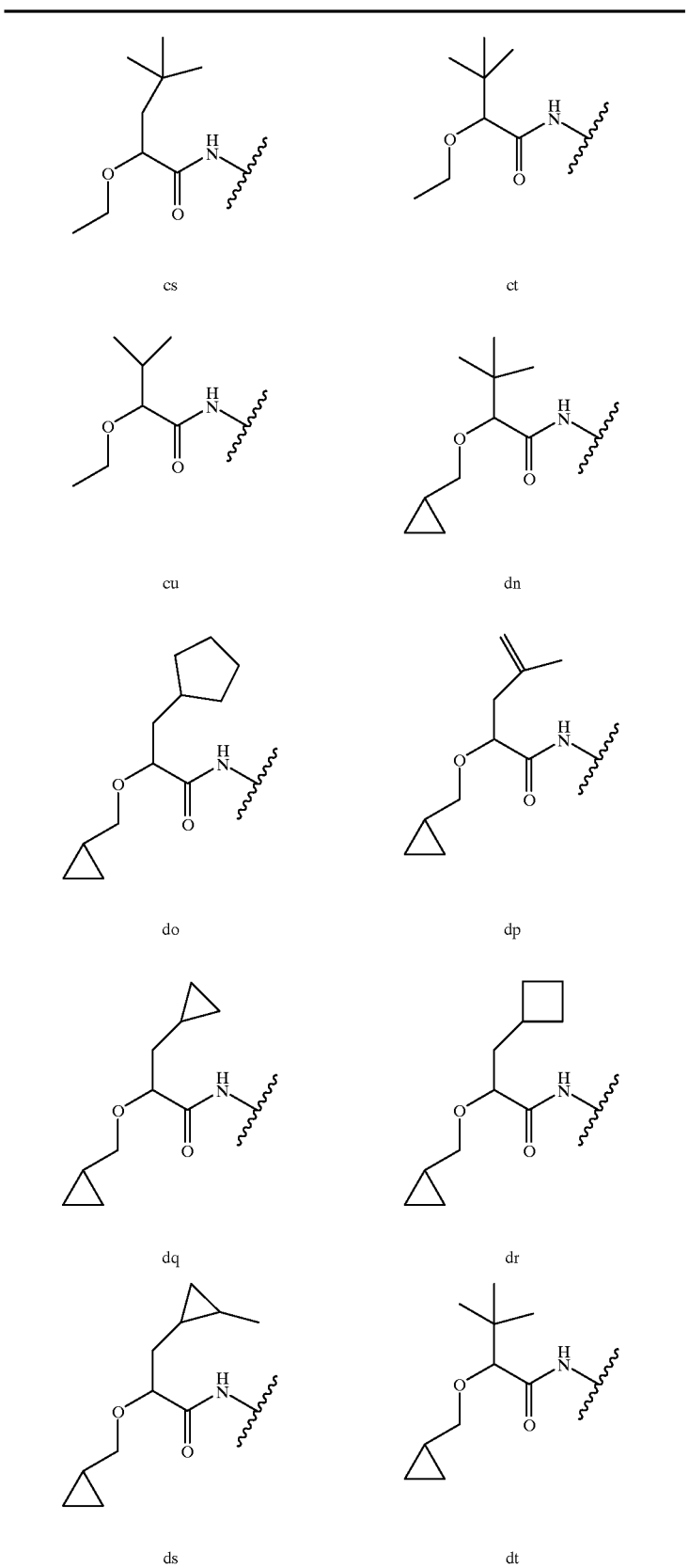

TABLE 2-continued
| | |
|---|---|
| 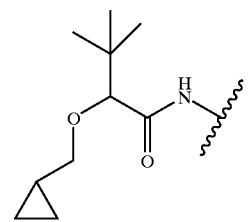 du | 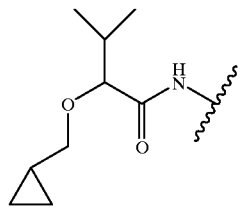 dv |
| 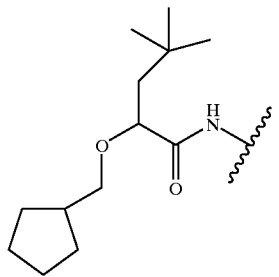 dw | 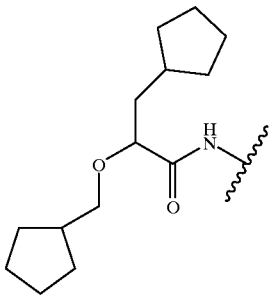 dx |
| 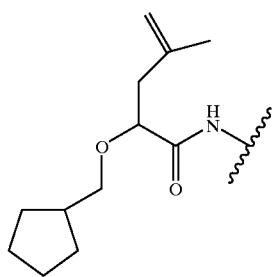 dy | 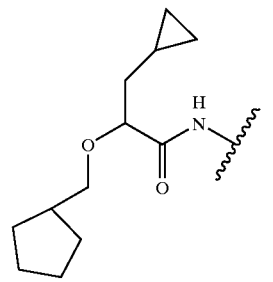 dz |
| 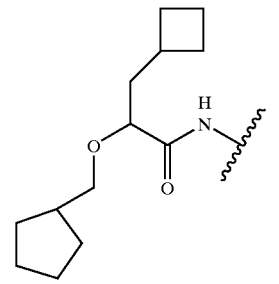 ea | 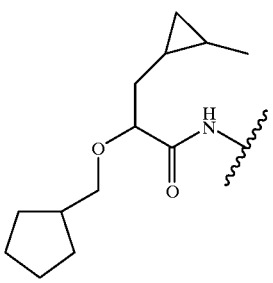 eb |
| 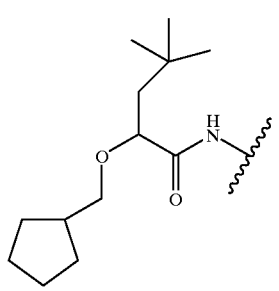 ec | 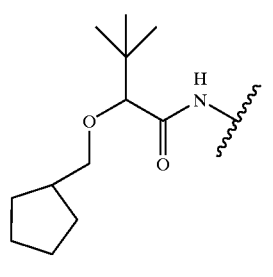 ed |

TABLE 2-continued
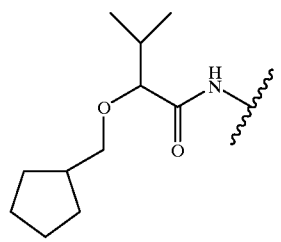
ee
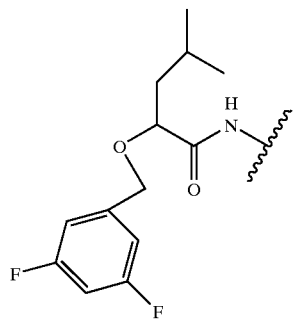
ef
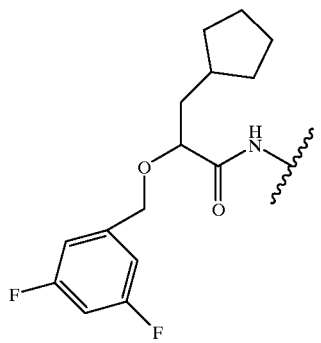
eg
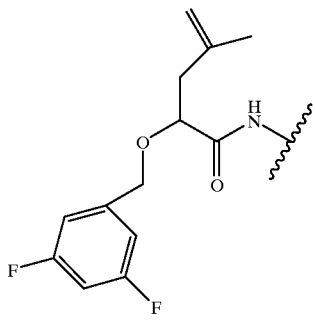
eh
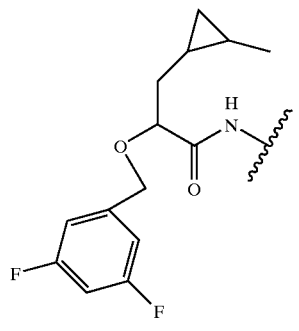
ei
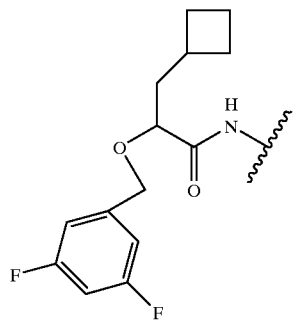
ej
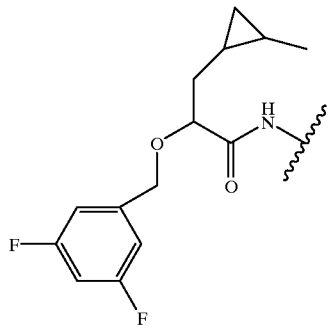
ek
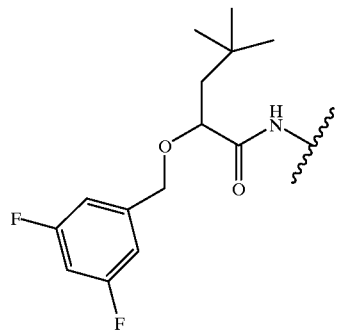
el TABLE 2-continued

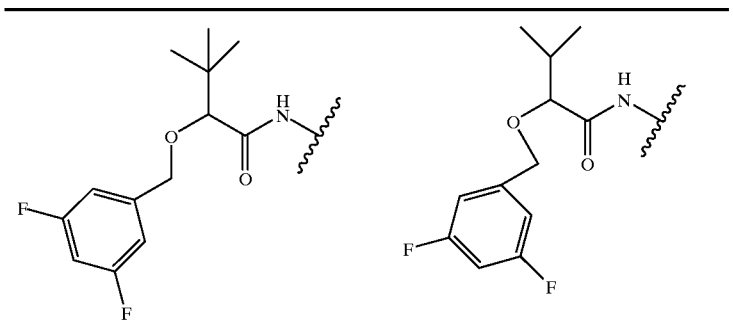

em                en

| Ex # | core | Q/R5 | R13 | -W-X-Y-Z |
|---|---|---|---|---|
| 500 | A - S | a - en | H | methyl |
| 501 | A - S | a - en | F | methyl |
| 502 | A - S | a - en | Cl | methyl |
| 503 | A - S | a - en | OH | methyl |
| 504 | A - S | a - en | —CH$_3$ | methyl |
| 505 | A - S | a - en | —CH$_2$CH$_3$ | methyl |
| 506 | A - S | a - en | —OCH$_3$ | methyl |
| 507 | A - S | a - en | —CF$_3$ | methyl |
| 508 | A - S | a - en | H | ethyl |
| 509 | A - S | a - en | F | ethyl |
| 510 | A - S | a - en | Cl | ethyl |
| 511 | A - S | a - en | OH | ethyl |
| 512 | A - S | a - en | —CH$_3$ | ethyl |
| 513 | A - S | a - en | —CH$_2$CH$_3$ | ethyl |
| 514 | A - S | a - en | —OCH$_3$ | ethyl |
| 515 | A - S | a - en | —CF$_3$ | ethyl |
| 516 | A - S | a - en | H | i-propyl |
| 517 | A - S | a - en | F | i-propyl |
| 518 | A - S | a - en | Cl | 1-propyl |
| 519 | A - S | a - en | OH | i-propyl |
| 520 | A - S | a - en | —CH$_3$ | i-propyl |
| 521 | A - S | a - en | —CH$_2$CH$_3$ | i-propyl |
| 522 | A - S | a - en | —OCH$_3$ | i-propyl |
| 523 | A - S | a - en | —CF$_3$ | i-propyl |
| 524 | A - S | a - en | H | n-propyl |
| 525 | A - S | a - en | F | n-propyl |
| 526 | A - S | a - en | Cl | n-propyl |
| 527 | A - S | a - en | OH | n-propyl |
| 528 | A - S | a - en | —CH$_3$ | n-propyl |
| 529 | A - S | a - en | —CH$_2$CH$_3$ | n-propyl |
| 530 | A - S | a - en | —OCH$_3$ | n-propyl |
| 531 | A - S | a - en | —CF$_3$ | n-propyl |
| 532 | A - S | a - en | H | n-butyl |
| 533 | A - S | a - en | F | n-butyl |
| 534 | A - S | a - en | Cl | n-butyl |
| 535 | A - S | a - en | OH | n-butyl |
| 536 | A - S | a - en | —CH$_3$ | n-butyl |
| 537 | A - S | a - en | —CH$_2$CH$_3$ | n-butyl |
| 538 | A - S | a - en | —OCH$_3$ | n-butyl |
| 539 | A - S | a - en | —CF$_3$ | n-butyl |
| 540 | A - S | a - en | H | i-butyl |
| 541 | A - S | a - en | F | i-butyl |
| 542 | A - S | a - en | Cl | i-butyl |
| 543 | A - S | a - en | OH | i-butyl |
| 544 | A - S | a - en | —CH$_3$ | i-butyl |
| 545 | A - S | a - en | —CH$_2$CH$_3$ | i-butyl |
| 546 | A - S | a - en | —OCH$_3$ | i-butyl |
| 547 | A - S | a - en | —CF$_3$ | i-butyl |
| 548 | A - S | a - en | H | s-butyl |
| 549 | A - S | a - en | F | s-butyl |
| 550 | A - S | a - en | Cl | s-butyl |
| 551 | A - S | a - en | OH | s-butyl |
| 552 | A - S | a - en | —CH$_3$ | s-butyl |
| 553 | A - S | a - en | —CH$_2$CH$_3$ | s-butyl |
| 554 | A - S | a - en | —OCH$_3$ | s-butyl |
| 555 | A - S | a - en | —CF$_3$ | s-butyl |
| 556 | A - S | a - en | H | t-butyl |
| 557 | A - S | a - en | F | t-butyl |
| 558 | A - S | a - en | Cl | t-butyl |

TABLE 2-continued

| | | | | |
|---|---|---|---|---|
| 559 | A - S | a - en | OH | t-butyl |
| 560 | A - S | a - en | —CH$_3$ | t-butyl |
| 561 | A - S | a - en | —CH$_2$CH$_3$ | t-butyl |
| 562 | A - S | a - en | —OCH$_3$ | t-butyl |
| 563 | A - S | a - en | —CF$_3$ | t-butyl |
| 564 | A - S | a - en | H | allyl |
| 565 | A - S | a - en | F | allyl |
| 566 | A - S | a - en | Cl | allyl |
| 567 | A - S | a - en | OH | allyl |
| 568 | A - S | a - en | —CH$_3$ | allyl |
| 569 | A - S | a - en | —CH$_2$CH$_3$ | allyl |
| 570 | A - S | a - en | —OCH$_3$ | allyl |
| 571 | A - S | a - en | —CF$_3$ | allyl |
| 572 | A - S | a - en | H | cyclopropyl |
| 573 | A - S | a - en | F | cyclopropyl |
| 574 | A - S | a - en | Cl | cyclopropyl |
| 575 | A - S | a - en | OH | cyclopropyl |
| 576 | A - S | a - en | —CH$_3$ | cyclopropyl |
| 577 | A - S | a - en | —CH$_2$CH$_3$ | cyclopropyl |
| 578 | A - S | a - en | —OCH$_3$ | cyclopropyl |
| 579 | A - S | a - en | —CF$_3$ | cyclopropyl |
| 580 | A - S | a - en | —CF$_3$ | cyclopropyl |
| 581 | A - S | a - en | H | cyclopropyl-CH$_2$— |
| 582 | A - S | a - en | F | cyclopropyl-CH$_2$— |
| 583 | A - S | a - en | Cl | cyclopropyl-CH$_2$— |
| 584 | A - S | a - en | OH | cyclopropyl-CH$_2$— |
| 585 | A - S | a - en | —CH$_3$ | cyclopropyl-CH$_2$— |
| 586 | A - S | a - en | —CH$_2$CH$_3$ | cyclopropyl-CH$_2$— |
| 587 | A - S | a - en | —OCH$_3$ | cyclopropyl-CH$_2$— |
| 588 | A - S | a - en | —CF$_3$ | cyclopropyl-CH$_2$— |
| 589 | A - S | a - en | H | cyclobutyl |
| 590 | A - S | a - en | F | cyclobutyl |
| 591 | A - S | a - en | Cl | cyclobutyl |
| 592 | A - S | a - en | OH | cyclobutyl |
| 593 | A - S | a - en | —CH$_3$ | cyclobutyl |
| 594 | A - S | a - en | —CH$_2$CH$_3$ | cyclobutyl |
| 595 | A - S | a - en | —OCH$_3$ | cyclobutyl |
| 596 | A - S | a - en | —CF$_3$ | cyclobutyl |
| 597 | A - S | a - en | H | cyclobutyl-CH$_2$— |
| 598 | A - S | a - en | F | cyclobutyl-CH$_2$— |
| 599 | A - S | a - en | Cl | cyclobutyl-CH$_2$— |
| 600 | A - S | a - en | OH | cyclobutyl-CH$_2$— |
| 601 | A - S | a - en | —CH$_3$ | cyclobutyl-CH$_2$— |
| 602 | A - S | a - en | —CH$_2$CH$_3$ | cyclobutyl-CH$_2$— |
| 603 | A - S | a - en | —OCH$_3$ | cyclobutyl-CH$_2$— |
| 604 | A - S | a - en | —CF$_3$ | cyclobutyl-CH$_2$— |
| 605 | A - S | a - en | H | cyclopentyl |
| 606 | A - S | a - en | F | cyclopentyl |
| 607 | A - S | a - en | Cl | cyclopentyl |
| 608 | A - S | a - en | OH | cyclopentyl |
| 609 | A - S | a - en | —CH$_3$ | cyclopentyl |
| 610 | A - S | a - en | —CH$_2$CH$_3$ | cyclopentyl |
| 611 | A - S | a - en | —OCH$_3$ | cyclopentyl |
| 612 | A - S | a - en | —CF$_3$ | cyclopentyl |
| 613 | A - S | a - en | H | cyclopentyl-CH$_2$— |
| 614 | A - S | a - en | F | cyclopentyl-CH$_2$— |
| 615 | A - S | a - en | Cl | cyclopentyl-CH$_2$— |
| 616 | A - S | a - en | OH | cyclopentyl-CH$_2$— |
| 617 | A - S | a - en | —CH$_3$ | cyclopentyl-CH$_2$— |
| 618 | A - S | a - en | —CH$_2$CH$_3$ | cyclopentyl-CH$_2$— |
| 619 | A - S | a - en | —OCH$_3$ | cyclopentyl-CH$_2$— |
| 620 | A - S | a - en | —CF$_3$ | cyclopentyl-CH$_2$— |
| 621 | A - S | a - en | H | cyclohexyl |
| 622 | A - S | a - en | F | cyclohexyl |
| 623 | A - S | a - en | Cl | cyclohexyl |
| 624 | A - S | a - en | OH | cyclohexyl |
| 625 | A - S | a - en | —CH$_3$ | cyclohexyl |
| 626 | A - S | a - en | —CH$_2$CH$_3$ | cyclohexyl |
| 627 | A - S | a - en | —OCH$_3$ | cyclohexyl |
| 628 | A - S | a - en | —CF$_3$ | cyclohexyl |
| 629 | A - S | a - en | H | cyclohexyl-CH$_2$— |
| 630 | A - S | a - en | F | cyclohexyl-CH$_2$— |
| 631 | A - S | a - en | Cl | cyclohexyl-CH$_2$— |
| 632 | A - S | a - en | OH | cyclohexyl-CH$_2$— |
| 633 | A - S | a - en | —CH$_3$ | cyclohexyl-CH$_2$— |
| 634 | A - S | a - en | —CH$_2$CH$_3$ | cyclohexyl-CH$_2$— |
| 635 | A - S | a - en | —OCH$_3$ | cyclohexyl-CH$_2$— |
| 636 | A - S | a - en | —CF$_3$ | cyclohexyl-CH$_2$— |
| 637 | A - S | a - en | H | phenyl |

TABLE 2-continued

| | | | | |
|---|---|---|---|---|
| 638 | A - S | a - en | F | phenyl |
| 639 | A - S | a - en | Cl | phenyl |
| 640 | A - S | a - en | OH | phenyl |
| 641 | A - S | a - en | —CH$_3$ | phenyl |
| 642 | A - S | a - en | —CH$_2$CH$_3$ | phenyl |
| 643 | A - S | a - en | —OCH$_3$ | phenyl |
| 644 | A - S | a - en | —CF$_3$ | phenyl |
| 645 | A - S | a - en | H | 2-F-phenyl |
| 646 | A - S | a - en | F | 2-F-phenyl |
| 647 | A - S | a - en | Cl | 2-F-phenyl |
| 648 | A - S | a - en | OH | 2-F-phenyl |
| 649 | A - S | a - en | —CH$_3$ | 2-F-phenyl |
| 650 | A - S | a - en | —CH$_2$CH$_3$ | 2-F-phenyl |
| 651 | A - S | a - en | —OCH$_3$ | 2-F-phenyl |
| 652 | A - S | a - en | —CF$_3$ | 2-F-phenyl |
| 653 | A - S | a - en | H | 3-F-phenyl |
| 654 | A - S | a - en | F | 3-F-phenyl |
| 655 | A - S | a - en | Cl | 3-F-phenyl |
| 656 | A - S | a - en | OH | 3-F-phenyl |
| 657 | A - S | a - en | —CH$_3$ | 3-F-phenyl |
| 658 | A - S | a - en | —CH$_2$CH$_3$ | 3-F-phenyl |
| 659 | A - S | a - en | —OCH$_3$ | 3-F-phenyl |
| 660 | A - S | a - en | —CF$_3$ | 3-F-phenyl |
| 661 | A - S | a - en | H | 4-F-phenyl |
| 662 | A - S | a - en | F | 4-F-phenyl |
| 663 | A - S | a - en | Cl | 4-F-phenyl |
| 664 | A - S | a - en | OH | 4-F-phenyl |
| 665 | A - S | a - en | —CH$_3$ | 4-F-phenyl |
| 666 | A - S | a - en | —CH$_2$CH$_3$ | 4-F-phenyl |
| 667 | A - S | a - en | —OCH$_3$ | 4-F-phenyl |
| 668 | A - S | a - en | —CF$_3$ | 4-F-phenyl |
| 669 | A - S | a - en | H | 3-Cl-phenyl |
| 670 | A - S | a - en | F | 3-Cl-phenyl |
| 671 | A - S | a - en | Cl | 3-Cl-phenyl |
| 672 | A - S | a - en | OH | 3-Cl-phenyl |
| 673 | A - S | a - en | —CH$_3$ | 3-Cl-phenyl |
| 674 | A - S | a - en | —CH$_2$CH$_3$ | 3-Cl-phenyl |
| 675 | A - S | a - en | —OCH$_3$ | 3-Cl-phenyl |
| 676 | A - S | a - en | —CF$_3$ | 3-Cl-phenyl |
| 677 | A - S | a - en | H | 4-Cl-phenyl |
| 678 | A - S | a - en | F | 4-Cl-phenyl |
| 679 | A - S | a - en | Cl | 4-Cl-phenyl |
| 680 | A - S | a - en | OH | 4-Cl-phenyl |
| 681 | A - S | a - en | —CH$_3$ | 4-Cl-phenyl |
| 682 | A - S | a - en | —CH$_2$CH$_3$ | 4-Cl-phenyl |
| 683 | A - S | a - en | —OCH$_3$ | 4-Cl-phenyl |
| 684 | A - S | a - en | —CF$_3$ | 4-Cl-phenyl |
| 685 | A - S | a - en | H | 3-Me-phenyl |
| 686 | A - S | a - en | F | 3-Me-phenyl |
| 687 | A - S | a - en | Cl | 3-Me-phenyl |
| 688 | A - S | a - en | OH | 3-Me-phenyl |
| 689 | A - S | a - en | —CH$_3$ | 3-Me-phenyl |
| 690 | A - S | a - en | —CH$_2$CH$_3$ | 3-Me-phenyl |
| 691 | A - S | a - en | —OCH$_3$ | 3-Me-phenyl |
| 692 | A - S | a - en | —CF$_3$ | 3-Me-phenyl |
| 693 | A - S | a - en | H | 4-Me-phenyl |
| 694 | A - S | a - en | F | 4-Me-phenyl |
| 695 | A - S | a - en | Cl | 4-Me-phenyl |
| 696 | A - S | a - en | OH | 4-Me-phenyl |
| 697 | A - S | a - en | —CH$_3$ | 4-Me-phenyl |
| 698 | A - S | a - en | —CH$_2$CH$_3$ | 4-Me-phenyl |
| 699 | A - S | a - en | —OCH$_3$ | 4-Me-phenyl |
| 700 | A - S | a - en | —CF$_3$ | 4-Me-phenyl |
| 701 | A - S | a - en | H | 3-MeO-phenyl |
| 702 | A - S | a - en | F | 3-MeO-phenyl |
| 703 | A - S | a - en | Cl | 3-MeO-phenyl |
| 704 | A - S | a - en | OH | 3-MeO-phenyl |
| 705 | A - S | a - en | —CH$_3$ | 3-MeO-phenyl |
| 706 | A - S | a - en | —CH$_2$CH$_3$ | 3-MeO-phenyl |
| 707 | A - S | a - en | —OCH$_3$ | 3-MeO-phenyl |
| 708 | A - S | a - en | —CF$_3$ | 3-MeO-phenyl |
| 709 | A - S | a - en | H | 4-MeO-phenyl |
| 710 | A - S | a - en | F | 4-MeO-phenyl |
| 711 | A - S | a - en | Cl | 4-MeO-phenyl |
| 712 | A - S | a - en | OH | 4-MeO-phenyl |
| 713 | A - S | a - en | —CH$_3$ | 4-MeO-phenyl |
| 714 | A - S | a - en | —CH$_2$CH$_3$ | 4-MeO-phenyl |
| 715 | A - S | a - en | —OCH$_3$ | 4-MeO-phenyl |
| 716 | A - S | a - en | —CF$_3$ | 4-MeO-phenyl |

TABLE 2-continued

| | | | | |
|---|---|---|---|---|
| 717 | A - S | a - en | H | 3-F$_3$C-phenyl |
| 718 | A - S | a - en | F | 3-F$_3$C-phenyl |
| 719 | A - S | a - en | Cl | 3-F$_3$C-phenyl |
| 720 | A - S | a - en | OH | 3-F$_3$C-phenyl |
| 721 | A - S | a - en | —CH$_3$ | 3-F$_3$C-phenyl |
| 722 | A - S | a - en | —CH$_2$CH$_3$ | 3-F$_3$C-phenyl |
| 723 | A - S | a - en | —OCH$_3$ | 3-F$_3$C-phenyl |
| 724 | A - S | a - en | —CF$_3$ | 3-F$_3$C-phenyl |
| 725 | A - S | a - en | H | 4-F$_3$C-phenyl |
| 726 | A - S | a - en | F | 4-F$_3$C-phenyl |
| 727 | A - S | a - en | Cl | 4-F$_3$C-phenyl |
| 728 | A - S | a - en | OH | 4-F$_3$C-phenyl |
| 729 | A - S | a - en | —CH$_3$ | 4-F$_3$C-phenyl |
| 730 | A - S | a - en | —CH$_2$CH$_3$ | 4-F$_3$C-phenyl |
| 731 | A - S | a - en | —OCH$_3$ | 4-F$_3$C-phenyl |
| 732 | A - S | a - en | —CF$_3$ | 4-F$_3$C-phenyl |

Utility

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of β amyloid precursor protein. Compounds that inhibit β or γ secretase activity, either directly or indirectly, control the production of Aβ. Such inhibition of β or γ secretases reduces production of Aβ, and is expected to reduce or prevent the neurological disorders associated with Aβ protein, such as Alzheimer's Disease.

Cellular screening methods for inhibitors of Aβ production, testing methods for the in vivo suppression of Aβ production, and assays for the detection of secretase activity are known in the art and have been disclosed in numerous publications, including *J.Med.Chem.* 1999, 42, 3889–3898, PCT publication number WO 98/22493, EPO publication number 0652009, U.S. Pat. Nos. 5,703,129 and 5,593,846; all hereby incorporated by reference.

The compounds of the present invention have utility for the prevention and treatment of disorders involving Aβ production, such as cerebrovascular disorders.

Compounds of Formula (I) are expected to possess γ-secretase inhibitory activity. The γ-secretase inhibitory activity of the compounds of the present invention is demonstrated using assays for such activity, for example, using the assay described below. Compounds of the present invention have been shown to inhibit the activity of γ-secretase, as determined by the Aβ immunoprecipitation assay.

Compounds provided by this invention should also be useful as standards and reagents in determining the ability of a potential pharmaceutical to inhibit Aβ production. These would be provided in commercial kits comprising a compound of this invention.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetic acid.

A compound is considered to be active if it has an IC$_{50}$ or K$_i$ value of less than about 100 μM for the inhibition of Aβ production. Preferrably the IC$_{50}$ or K$_i$ value is less than about 10 μM; more preferrably the IC$_{50}$ or K$_i$ value is less than about 0.1 μM. Compounds of the present invention have been shown to inhibit Aβ protein production with an IC$_{50}$ or K$_i$ value of less than 100 μM.

β Amyloid Precursor Protein Accumulation Assay

A novel assay to evaluate the accumulation of Aβprotein was developed to detect potential inhibitors of secretase. The assay uses the N 9 cell line, characterized for expression of exogenous APP by immunoblotting and immunoprecipitation.

The effect of test compounds on the accumulation of Aβ in the conditioned medium is tested by immunoprecipitation. Briefly, N 9 cells are grown to confluency in 6-well plates and washed twice with 1×Hank's buffered salt solution. The cells are starved in methionine/cysteine deficient media for 30 min, followed by replacement with fresh deficient media containing 150 uCi S35 Translabel (Amersham). Test compounds dissolved in DMSO (final concentration 1%) are added together with the addition of radiolabel. The cells are incubated for 4 h at 37° C. in a tissue culture incubator.

At the end of the incubation period, the conditioned medium is harvested and pre-cleared by the addition of 5 μl normal mouse serum and 50 ul of protein A Sepharose (Pharmacia), mixed by end-over-end rotation for 30 minutes at 4° C., followed by a brief centrifugation in a microfuge. The supernatant is then harvested and transferred to fresh tubes containing 5 ug of a monoclonal antibody (clone 1101.1; directed against an internal peptide sequence in Aβ) and 50 μl protein A Sepharose. After incubation overnight at 4° C., the samples are washed three times with high salt washing buffer (50 mM Tris, pH 7.5, 500 mM NaCl, 5 mM EDTA, 0.5% Nonidet P-40), three times with low salt wash buffer (50 mM Tris, pH 7.5, 150 mM NaCl, 5 mM EDTA, 0.5% Nonidet P-40), and three times with 10 mM Tris, pH 7.5. The pellet after the last wash is resuspended in SDS sample buffer (Laemmli, 1970) and boiled for 3 minutes. The supernatant is then fractionated on either 10–20% Tris/Tricine SDS gels or on 16.5% Tris/Tricine SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound blocks Aβ accumulation in the conditioned medium, and is therefore considered active, with an IC$_{50}$ less than 100 μM.

C-terminus β Amyloid Precursor Protein Accumulation Assay

The effect of test compounds on the accumulation of C-terminal fragments is determined by immunoprecipitation of APP and fragments thereof from cell lysates. N 9 cells are metabolically labeled as above in the presence or absence of test compounds. At the end of the incubation period, the conditioned medium are harvested and cells lysed in RIPA buffer (10 mM Tris, pH 8.0 containing 1% Triton X-100, 1% deoxycholate, 0.1% SDS, 150 mM NaCl, 0.125% NaN$_3$). Again, lysates are precleared with 5 ul normal rabbit serum/ 50 ul protein A Sepharose, followed by the addition of BC-1 antiserum (15 $\mu$l;) and 50 $\mu$l protein A Sepharose for 16 hours at 4° C. The immunoprecipitates are washed as above, bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound stimulates C-terminal fragment accumulation in the cell lysates, and is therefore considered active, with an IC$_{50}$ less than 100 $\mu$M.

A$\beta$ Immunoprecipitation Assay

This immunoprecipitation assay is specific for $\gamma$ secretase (i.e., proteolytic activity required to generate the C-terminal end of A$\beta$ either by direct cleavage or generating a C-terminal extended species which is subsequently further proteolyzed). N 9 cells are pulse labeled in the presence of a reported $\gamma$ secretase inhibitor (MDL 28170) for 1 h, followed by washing to remove radiolabel and MDL 28170. The media is replaced and test compounds are added. The cells are chased for increasing periods of times and A $\beta$ is isolated from the conditioned medium and C-terminal fragments from cell lysates (see above). The test compounds are characterized whether a stabilization of C-terminal fragments is observed and whether A$\beta$ is generated from these accumulated precursor. A typical test compound prevents the generation of A$\beta$ out of accumulated C-terminal fragments and is considered active with an IC$_{50}$ less than 100 $\mu$M.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to $\beta$-amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or $\beta$-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of Formula (I):

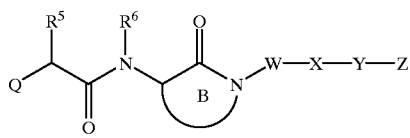

(I)

or a pharmaceutically acceptable salt thereof, wherein:

Q is $-(CR^7R^{7a})_m-R^4$, $-(CR^7R^{7a})_n-S-R^4$, $-(CR^7R^{7a})_n-O-R^4$, $-(CR^7R^{7a})_m-N(R^{7b})-R^4$, $-(CR^7R^{7a})_n-S(=O)-R^4$, $-(CR^7R^{7a})_n-S(=O)_2-R^4$, or $-(CR^7R^{7a})_n-C(=O)-R^4$;

provided when n is 0, then $R^4$ is not H;

m is 1, 2, or 3;

n is 0, 1, or 2;

$R^4$ is H, $C_1-C_8$ alkyl substituted with 0–3 $R^{4a}$,
$C_2-C_8$ alkenyl substituted with 0–3 $R^{4a}$,
$C_2-C_8$ alkynyl substituted with 0–3 $R^{4a}$,
$C_3-C_{10}$ carbocycle substituted with 0–3 $R^{4b}$,
aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from is H, Cl, F, Br, I, CN, $NO_2$, $NR^{15}R^{16}$, $CF_3$, $OR^{14a}$, $OR^{22}$, $SR^{22}$, $C(=O)OR^{22}$, $NR^{21}R^{22}$, $S(=O)R^{22}$, $S(=O)_2R^{22}$, $C_1-C_6$ alkyl, $C_1-C_4$ alkoxy, $C_1-C_4$ haloalkyl,
$C_1-C_4$ haloalkoxy, $C_1-C_4$ haloalkyl-S—,
$C_3-C_{10}$ carbocycle substituted with 0–3 $R^{4b}$,
aryl substituted with 0–3 $R^{4b}$, and
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, and $C_1-C_4$ haloalkyl-S—;

$R^5$ is H;

$C_1-C_6$ alkyl substituted with 0–3 $R^{5b}$;
$C_2-C_6$ alkenyl substituted with 0–3 $R^{5b}$;
$C_2-C_6$ alkynyl substituted with 0–3 $R^{5b}$;
$C_3-C_{10}$ carbocycle substituted with 0–3 $R^{5c}$;
aryl substituted with 0–3 $R^{5c}$; and
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from:
H, $C_1-C_6$ alkyl, $CF_3$, Cl, F, Br, I, =O, CN, $NO_2$, $NR^{15}R^{16}$;
$C_3-C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, and
$C_1-C_4$ haloalkoxy, and $C_1-C_4$ haloalkyl-S—;

$R^6$ is H;

$C_1-C_6$ alkyl substituted with 0–3 $R^{6a}$;
$C_3-C_{10}$ carbocycle substituted with 0–3 $R^{6b}$; or
aryl substituted with 0–3 $R^{6b}$;

$R^{6a}$, at each occurrence, is independently selected from H, $C_1-C_6$ alkyl, $OR^{14}$, Cl, F, Br, I, =O, CN, $NO_2$, $NR^{15}R^{16}$, aryl or $CF_3$;

$R^{6b}$, at each occurrence, is independently selected from H, OH, Cl, F, Br, I, CN, $NO_2$, $NR^{15}R^{16}$, $CF_3$, $C_1-C_6$ alkyl, $C_1-C_4$ alkoxy, $C_1-C_4$ haloalkyl, and $C_1-C_4$ haloalkoxy;

$R^7$, at each occurrence, is independently H or $C_1-C_4$ alkyl;

$R^{7a}$, at each occurrence, is independently H or $C_1-C_4$ alkyl;

$R^{7b}$ is H or $C_1-C_4$ alkyl;

Ring B is

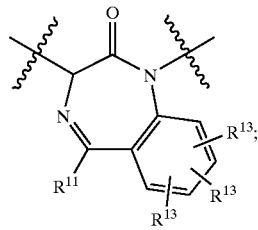

R$^{11}$ at each occurrence, is independently selected from H, C$_1$–C$_4$ alkoxy, Cl, F, Br, I, =O, CN, NO$_2$, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
C$_1$–C$_6$ alkyl optionally substituted with 0–3 R$^{11a}$;
aryl substituted with 0–3 R$^{11b}$;
C$_3$–C$_{10}$ carbocycle substituted with 0–3 R$^{11b}$; or
5 to 10 membered heterocycle containing 1 to 4 heteroatoms selected from nitrogen, oxygen, and sulphur, wherein said 5 to 10 membered heterocycle is substituted with 0–3 R$^{11b}$;

R$^{11a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$;
phenyl substituted with 0–3 R$^{11b}$;
C$_3$–C$_6$ cycloalkyl substituted with 0–3 R$^{11b}$; and
5 to 6 membered heterocycle containing 1 to 3 heteroatoms selected from nitrogen, oxygen, and sulphur, wherein said 5 to 6 membered heterocycle is substituted with 0–3 R$^{11b}$;

R$^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

W is a bond or —(CR$^8$R$^{8a}$)$_p$—;
p is 0, 1, 2, 3, or 4;
R$^8$ and R$^{8a}$, at each occurrence, are independently selected from H, F, C$_1$–C$_4$ alkyl, C$_2$–C$_4$ alkenyl, C$_2$–C$_4$ alkynyl and C$_3$–C$_8$ cycloalkyl;

X is a bond;
aryl substituted with 0–3 R$^{Xb}$;
C$_3$–C$_{10}$ carbocycle substituted with 0–3 R$^{Xb}$; or
5 to 10 menibered heterocycle substituted with 0–2 R$^{Xb}$;

R$^{Xb}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

Y is a bond or —(CR$^9$R$^{9a}$)$_t$—V—(CR$^9$R$^{9a}$)$_u$—;
t is 0, 1, or 2;
u is 0, 1, or 2;
R$^9$ and R$^{9a}$, at each occurrence, are independently selected from H, F, C$_1$–C$_6$ alkyl or C$_3$–C$_8$ cycloalkyl;
V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, —S(=O)NR$^{19b}$—, —C(=O)O—, or —OC(=O)—;

Z is H;
C$_1$–C$_8$ alkyl substituted with 0–3 R$^{12a}$;
C$_2$–C$_6$ alkenyl substituted with 0–3 R$^{12a}$;
C$_2$–C$_6$ alkynyl substituted with 0–3 R$^{12a}$;
aryl substituted with 0–4 R$^{12b}$;
C$_3$–C$_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12a}$, at each occurrence, is independently selected from H, OH, Cl, F, Br, I, CN, NO$_2$, NR$^{15}$R$^{16}$, —C(=O)NR$^{15}$R$^{16}$,
CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, C$_1$–C$_4$ haloalkyl-S—, aryl substituted with 0–4 R$^{12b}$;
C$_3$–C$_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, aryl, C$_3$–C$_6$ cycloalkyl, C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

R$^{13}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, and CF$_3$;

R$^{14}$ is H, phenyl, benzyl, C$_1$–C$_6$ alkyl, C$_2$–C$_6$ alkoxyalkyl, or C$_3$–C$_6$ cycloalkyl;

R$^{14a}$ is H, phenyl, benzyl, or C$_1$–C$_4$ alkyl;

R$^{15}$, at each occurrence, is independently selected from H, C$_1$–C$_6$ alkyl, benzyl, phenethyl, (C$_1$–C$_6$ alkyl)-C(=O)—, and (C$_1$–C$_6$ alkyl)-S(=O)$_2$—;

R$^{16}$, at each occurrence, is independently selected from H, OH, C$_1$–C$_6$ alkyl, benzyl, phenethyl, (C$_1$–C$_6$ alkyl)-C(=O)—, and (C$_1$–C$_6$ alkyl)-S(=O)$_2$—;

alternatively, R$^{15}$ and R$^{16}$, together with the nitrogen to which they are attached, may combine to form a 4–7 membered ring wherein said 4–7 membered ring optionally contains an additional heteroatom selected from O or NH;

R$^{17}$ is H, C$_1$–C$_6$ alkyl, C$_2$–C$_6$ alkoxyalkyl, aryl substituted by 0–4 R$^{17a}$, or —CH$_2$-aryl substituted by 0–4 R$^{17a}$;

R$^{17a}$ is H, methyl, ethyl, propyl, butyl, methoxy, ethoxy, propoxy, butoxy, —OH, F, Cl, Br, I, CF$_3$, OCF$_3$, SCH$_3$, S(O)CH$_3$, SO$_2$CH$_3$, —NH$_2$, —N(CH$_3$)$_2$, or C$_1$–C$_4$ haloalkyl;

R$^{18}$, at each occurrence, is independently selected from H, C$_1$–C$_6$ alkyl, phenyl, benzyl, phenethyl, (C$_1$–C$_6$ alkyl)-C(=O)—, and (C$_1$–C$_6$ alkyl)-S(=O)$_2$—;

R$^{19}$, at each occurrence, is independently selected from H, OH, C$_1$–C$_6$ alkyl, phenyl, benzyl, phenethyl, (C$_1$–C$_6$ alkyl)-C(=O)—, and (C$_1$–C$_6$ alkyl)-S(=O)$_2$—;

R$^{19b}$, at each occurrence, is independently is H or C$_1$–C$_4$ alkyl;

R$^{21}$ is H, phenyl, benzyl, or C$_1$–C$_4$ alkyl; and

R$^{22}$ is C$_1$–C$_4$ alkyl, C$_2$–C$_4$ alkenyl, or C$_3$–C$_4$ alkynyl.

2. A compound, according to claim 1, of Formula (I) or a pharmaceutically acceptable salt thereof, wherein:

Q is —(CR$^7$R$^{7a}$)$_m$—R$^4$, —(CR$^7$R$^{7a}$)$_n$—S—R$^4$, —(CR$^7$R$^{7a}$)$_n$—O—R$^4$, or

—(CR$^7$R$^{7a}$)$_m$—N(R$^{7b}$)—R$^4$;

m is 1 or 2;

n is 0 or 1;

R$^4$ is H,
 C$_1$–C$_8$ alkyl substituted with 0–3 R$^{4a}$,
 C$_2$–C$_8$ alkenyl substituted with 0–3 R$^{4a}$,
 C$_2$–C$_8$ alkynyl substituted with 0–3 R$^{4a}$,
 C$_3$–C$_{10}$ carbocycle substituted with 0–3 R$^{4b}$,
 aryl substituted with 0–3 R$^{4b}$, or
 5 to 10 membered heterocycle containing 1 to 4 heteroatoms selected from nitrogen, oxygen, and sulphur, wherein said 5 to 10 membered heterocycle is substituted with 0–3 R$^{4b}$;

R$^{4a}$, at each occurrence, is independently selected from is H, Cl, F, Br, I, CN, NO$_2$, NR$^{15}$R$^{16}$, CF$_3$, OR$^{14a}$, C(=O)OR$^{22}$, SR$^{22}$, OR$^{22}$, NR$^{21}$R$^{22}$, S(=O)R$^{22}$, S(=O)$_2$R$^{22}$,
 C$_1$–C$_6$ alkyl, C$_1$–C$_4$ alkoxy, C$_1$–C$_4$ haloalkyl,
 C$_1$–C$_4$ haloalkoxy, C$_1$–C$_4$ haloalkyl-S—,
 C$_3$–C$_{10}$ carbocycle substituted with 0–3 R$^{4b}$,
 aryl substituted with 0–3 R$^{4b}$, and
 5 to 10 membered heterocycle containing 1 to 4 heteroatoms selected from nitrogen, oxygen, and sulphur, wherein said 5 to 10 membered heterocycle is substituted with 0–3 R$^{4b}$;

R$^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
 C$_1$–C$_6$ alkyl, C$_1$–C$_4$ alkoxy, C$_1$–C$_4$ haloalkyl,
 C$_1$–C$_4$ haloalkoxy, and C$_1$–C$_4$ haloalkyl-S—;

R$^5$ is H;
 C$_1$–C$_6$ alkyl substituted with 0–3 R$^{5b}$;
 C$_2$–C$_6$ alkenyl substituted with 0–3 R$^{5b}$;
 C$_2$–C$_6$ alkynyl substituted with 0–3 R$^{5b}$;
 C$_3$–C$_{10}$ carbocycle substituted with 0–3 R$^{5c}$;
 aryl substituted with 0–3 R$^{5c}$; and
 5 to 10 membered heterocycle containing 1 to 4 heteroatoms selected from nitrogen, oxygen, and sulphur, wherein said 5 to 10 membered heterocycle is substituted with 0–3 R$^{5c}$;

R$^{5b}$, at each occurrence, is independently selected from: H, C$_1$–C$_6$ alkyl, CF$_3$, Cl, F, Br, I, =O, CN, NO$_2$, NR$^{15}$R$^{16}$;
 C$_3$–C$_{10}$ carbocycle substituted with 0–3 R$^{5c}$;
 aryl substituted with 0–3 R$^{5c}$; or
 5 to 10 membered heterocycle containing 1 to 4 heteroatoms selected from nitrogen, oxygen, and sulphur, wherein said 5 to 10 membered heterocycle is substituted with 0–3 R$^{5c}$;

R$^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
 C$_1$–C$_6$ alkyl, C$_1$–C$_4$ alkoxy, C$_1$–C$_4$ haloalkyl, and
 C$_1$–C$_4$ haloalkoxy, and C$_1$–C$_4$ haloalkyl-S—;

R$^6$ is H, methyl, or ethyl;

R$^7$, at each occurrence, is independently H or C$_1$–C$_4$ alkyl;

R$^{7a}$, at each occurrence, is independently H or C$_1$–C$_4$ alkyl;

R$^{7b}$ is H or C$_1$–C$_4$ alkyl;

Ring B is

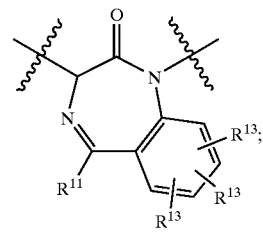

R$^{11}$, at each occurrence, is independently selected from H, C$_1$–C$_4$ alkoxy, Cl, F, Br, I, =O, CN, NO$_2$, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
 C$_1$–C$_6$ alkyl optionally substituted with 0–3 R$^{11a}$;
 aryl substituted with 0–3 R$^{11b}$;
 C$_3$–C$_{10}$ carbocycle substituted with 0–3 R$^{11b}$; or
 5 to 10 membered heterocycle containing 1 to 4 heteroatoms selected from nitrogen, oxygen, and sulphur, wherein said 5 to 10 membered heterocycle is substituted with 0–3 R$^{11b}$;

R$^{11a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$;
 phenyl substituted with 0–3 R$^{11b}$;
 C$_3$–C$_6$ cycloalkyl substituted with 0–3 R$^{11b}$; and
 5 to 6 membered heterocycle containing 1 to 3 heteroatoms selected from nitrogen, oxygen, and sulphur, wherein said 5 to 6 membered heterocycle is substituted with 0–3 R$^{11b}$;

R$^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
 C$_1$–C$_6$ alkyl, C$_1$–C$_4$ alkoxy, C$_1$–C$_4$ haloalkyl,
 C$_1$–C$_4$ haloalkoxy, and C$_1$–C$_4$ haloalkyl-S—;

W is a bond or —(CH$_2$)$_p$—;

p is 1 or 2;

X is a bond;
 phenyl substituted with 0–2 R$^{Xb}$;
 C$_3$–C$_6$ carbocycle substituted with 0–2 R$^{Xb}$; or
 5 to 6 membered heterocycle substituted with 0–2 R$^{Xb}$;

R$^{Xb}$, at each occurrence, is independently selected from H, OH, Cl, F, Br, I, CN, NO$_2$, NR$^{15}$R$^{16}$, CF$_3$, acetyl, SCH$_3$, S(=O)$_2$CH$_3$, S(=O)$_2$CH$_3$, C$_1$–C$_4$ alkyl, C$_1$–C$_3$ alkoxy, C$_1$–C$_3$ haloalkyl, C$_1$–C$_3$ haloalkoxy, and C$_1$–C$_3$ halothioalkoxy;

Y is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, —S(=O)NR$^{19b}$—, —C(=O)O—, or
 —OC(=O)—;

Z is H;
 C$_1$–C$_8$ alkyl substituted with 0–3 R$^{12a}$;
 C$_2$–C$_6$ alkenyl substituted with 0–3 R$^{12a}$;
 C$_2$–C$_6$ alkynyl substituted with 0–3 R$^{12a}$;
 aryl substituted with 0–4 R$^{12b}$;
 C$_3$–C$_{10}$ carbocycle substituted with 0–4 R$^{12b}$; or
 5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12a}$, at each occurrence, is independently selected from H, OH, Cl, F, Br, I, CN, NO$_2$, NR$^{15}$R$^{16}$, —C(=O)

$NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, OH, $C_1$–$C_6$ alkyl, benzyl, phenethyl, ($C_1$–$C_6$ alkyl)-C(=O)—, and ($C_1$–$C_6$ alkyl)-S(=O)$_2$—;

alternatively, $R^{15}$ and $R^{16}$, together with the nitrogen to which they are attached, may combine to form a 4–7 membered ring wherein said 4–7 membered ring optionally contains an additional heteroatom selected from O or NH;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, phenethyl;

$R^{19b}$, at each occurrence, is independently is H or $C_1$–$C_4$ alkyl;

$R^{21}$ is H, phenyl, benzyl, or $C_1$–$C_4$ alkyl; and $R^{22}$ is $C_1$–$C_4$ alkyl, $C_2$–$C_4$ alkenyl, or $C_3$–$C_4$ alkynyl.

3. A compound, according to claim 2, of Formula (Ib):

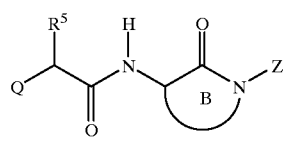

(Ib)

or a pharmaceutically acceptable salt thereof, wherein:

Q is —(CHR$^7$)$_m$—R$^4$, —(CHR$^7$)$_n$—S—R$^4$, —(CHR$^7$)$_n$—O—R$^4$, or

—(CHR$^7$)$_m$—N(R$^{7b}$)—R$^4$;

m is 1 or 2;

n is 0 or 1;

$R^4$ is H, $C_1$–$C_8$ alkyl substituted with 0–3 $R^{4a}$, $C_2$–$C_8$ alkenyl substituted with 0–3 $R^{4a}$, $C_2$–$C_8$ alkynyl substituted with 0–3 $R^{4a}$, $C_3$–$C_{10}$ carbocycle substituted with 0–3 $R^{4b}$, aryl substituted with 0–3 $R^{4b}$, or 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from is H, Cl, F, Br, I, CN, $NO_2$, $NR^{15}R^{16}$, $CF_3$, $OR^{14a}$, C(=O)OR$^{22}$, SR$^{22}$, OR$^{22}$, NR$^{21}$R$^{22}$, S(=O)R$^{22}$, S(=O)$_2$R$^{22}$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_3$–$C_{10}$ carbocycle substituted with 0–3 $R^{4b}$, aryl substituted with 0–3 $R^{4b}$, and 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ is H;

$C_1$–$C_6$ alkyl substituted with 0–3 $R^{5b}$;

$C_2$–$C_6$ alkenyl substituted with 0–3 $R^{5b}$;

$C_2$–$C_6$ alkynyl substituted with 0–3 $R^{5b}$;

$C_3$–$C_{10}$ carbocycle substituted with 0–3 $R^{5c}$;

aryl substituted with 0–3 $R^{5c}$; and 5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from: H, $C_1$–$C_6$ alkyl, $CF_3$, Cl, F, Br, I, =O, CN, $NO_2$, $R^{15}R^{16}$;

$C_3$–$C_{10}$ carbocycle substituted with 0–3 $R^{5c}$;

aryl substituted with 0–3 $R^{5c}$; or 5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy, and $C_1$–$C_4$ haloalkyl-S—;

$R^7$, at each occurrence, is independently H, methyl, or ethyl;

$R^{7b}$ is H, methyl, or ethyl;

Ring B is

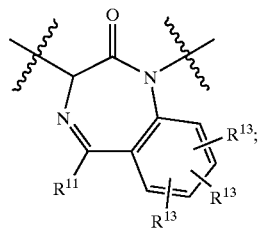

$R^{11}$, at each occurrence, is independently selected from H, $C_1$–$C_4$ alkoxy, Cl, F, Br, I, =O, CN, $NO_2$, $NR^{18}R^{19}$, C(=O)$R^{17}$, C(=O)O$R^{17}$, C(=O)$NR^{18}R^{19}$, $S(=O)_2$$NR^{18}R^{19}$, $CF_3$;
$C_1$–$C_6$ alkyl optionally substituted with 0–3 $R^{11a}$;
aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, O$R^{14}$, Cl, F, Br, I, =O, CN, $NO_2$, $NR^{15}R^{16}$, $CF_3$;
phenyl substituted with 0–3 $R^{11b}$;
$C_3$–$C_6$ cycloalkyl substituted with 0–3 $R^{11b}$; and
5 to 6 membered heterocycle containing 1 to 3 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl,
$C_1$–$C_4$ haloalkoxy, and $C_1$–$C_4$ haloalkyl-S—;

W is a bond;
X is a bond;
Y is a bond;
Z is H;
$C_1$–$C_8$ alkyl substituted with 0–3 $R^{12a}$;
$C_2$–$C_6$ alkenyl substituted with 0–3 $R^{12a}$;
$C_2$–$C_6$ alkynyl substituted with 0–3 $R^{12a}$;
aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl,
$C_1$–$C_4$ haloalkoxy, $C_1$–$C_4$ haloalkyl-S—,
aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl,
$C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-$S(=O)_2$—;

$R^{16}$, at each occurrence, is independently selected from H, OH, $C_1$–$C_6$ alkyl, benzyl, phenethyl, ($C_1$–$C_6$ alkyl)-C(=O)—, and ($C_1$–$C_6$ alkyl)-$S(=O)_2$—;

alternatively, $R^{15}$ and $R^{16}$, together with the nitrogen to which they are attached, may combine to form a 4–7 membered ring wherein said 4–7 membered ring optionally contains an additional heteroatom selected from O or NH;

$R^{17}$ is H, $C_1$–$C_6$ alkyl, $C_2$–$C_6$ alkoxyalkyl, aryl substituted by 0–4 $R^{17a}$, or
—$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-$S(=O)_2$—;

$R^{19}$, at each occurrence, is independently selected from H, OH, methyl, ethyl, propyl, butyl, phenyl, benzyl, phenethyl;

$R^{21}$ is H, phenyl, benzyl, methyl, ethyl, propyl, or butyl; and $R^{22}$ is methyl, ethyl, propyl, butyl, propenyl, butenyl, and propargyl.

4. A compound according to claim 3 of Formula (I) or a pharmaceutically acceptable salt thereof, wherein:

Q is —$(CH_2)_m$—$R^4$, —$(CH_2)_n$—S—$R^4$, —$(CH_2)_n$—O—$R^4$, or
—$(CH_2)_m$—N(H)—$R^4$;
m is 1 or 2;
n is 0 or 1;
$R^4$ is $C_1$–$C_8$ alkyl substituted with 0–3 $R^{4a}$,
$C_2$–$C_8$ alkenyl substituted with 0–3 $R^{4a}$,
$C_2$–$C_8$ alkynyl substituted with 0–3 $R^{4a}$,
$C_3$–$C_{10}$ carbocycle substituted with 0–3 $R^{4b}$,
aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from is H, Cl, F, Br, I, CN, $NO_2$, $NR^{15}R^{16}$, $CF_3$, C(=O)O$R^{22}$, S$R^{22}$, O$R^{22}$, O$R^{14a}$, $NR^{21}R^{22}$, $S(=O)R^{22}$, $S(=O)_2R^{22}$,
$C_1$–$C_6$ alkyl, $C_1$–$C_4$ alkoxy, $C_1$–$C_4$ haloalkyl,
$C_1$–$C_4$ haloalkoxy, $C_1$–$C_4$ haloalkyl-S—,
$C_3$–$C_{10}$ carbocycle substituted with 0–3 $R^{4b}$,
aryl substituted with 0–3 $R^{4b}$, and
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ is H;
$C_1$–$C_6$ alkyl substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
aryl substituted with 0–3 $R^{5c}$; and
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from:
H, $C_1$–$C_6$ alkyl, $CF_3$, Cl, F, Br, I, =O, CN, $NO_2$, $R^{15}R^{16}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl, and $C_1$–$C_4$ haloalkoxy;

Ring B is

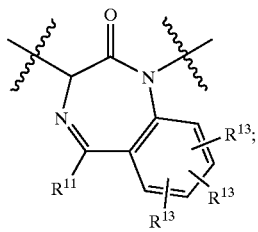

$R^{11}$, at each occurrence, is independently selected from H, =O, $NR^{18}R^{19}$, $CF_3$;
$C_1$–$C_4$ alkyl optionally substituted with 0–1 $R^{11a}$;
phenyl substituted with 0–3 $R^{11b}$;
$C_3$–$C_6$ carbocycle substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, $C_1$–$C_4$ alkyl, $OR^{14}$, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond;
X is a bond;
Y is a bond;
Z is H;
$C_1$–$C_8$ alkyl substituted with 0–3 $R^{12a}$;
$C_2$–$C_6$ alkenyl substituted with 0–3 $R^{12a}$; or
$C_2$–$C_6$ alkynyl substituted with 0–3 $R^{12a}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—,
aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$; and wherein said 5 to 10 membered heterocycle is selected from pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_4$ alkyl)-C(=O)—, and ($C_1$–$C_4$ alkyl)-S(=O)$_2$—;

$R^{16}$, at each occurrence, is independently selected from H, OH, $C_1$–$C_6$ alkyl, benzyl, phenethyl, ($C_1$–$C_4$ alkyl)-C(=O)—, and ($C_1$–$C_4$ alkyl)-S(=O)$_2$—; and
alternatively, $R^{15}$ and $R^{16}$, together with the nitrogen to which they are attached, may combine to form a 4–6 membered ring wherein said 4–6 membered ring optionally contains an additional heteroatom selected from O or NH, wherein said 4–6 membered ring is selected from imidazolidinyl, oxazolidinyl, thiazolidinyl, piperazinyl, morpholinyl, and thiomorpholinyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, phenethyl;

$R^{21}$ is H, phenyl, benzyl, methyl, ethyl, propyl, or butyl; and $R^{22}$ is methyl, ethyl, propyl, butyl, propenyl, butenyl, and propargyl.

5. A compound according to claim 4 wherein:
Q is —$CH_2R^4$, —O—$R^4$, or —$CH_2$—NH—$R^4$;
$R^4$ is $C_1$–$C_6$ alkyl substituted with 0–3 $R^{4a}$,
$C_2$–$C_6$ alkenyl substituted with 0–3 $R^{4a}$,
$C_2$–$C_6$ alkynyl substituted with 0–3 $R^{4a}$,
$C_3$–$C_6$ carbocycle substituted with 0–3 $R^{4b}$,
phenyl substituted with 0–3 $R^{4b}$, or
5 to 6 membered heterocycle containing 1 to 3 heteroatoms selected from nitrogen, oxygen, and sulphur, wherein said 5 to 6 membered heterocycle is substituted with 0–3 $R^{4b}$;

$R^{4a}$, at each occurrence, is independently selected from H, Cl, F, Br, I, CN, $NO_2$, $NR^{15}R^{16}$, $CF_3$, C(=O)OR22, $SR^{22}$, $OR^{14a}$, $OR^{22}$, $NR^{21}R^{22}$, S(=O)$R^{22}$, $S(=O)_2R^{22}$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_3$–$C_{10}$ carbocycle substituted with 0–3 $R^{4b}$, aryl substituted with 0–3 $R^{4b}$, and
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, S(=O)$CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ is H;
$C_1$–$C_6$ alkyl substituted with 0–3 $R^{5b}$;
$C_2$–$C_6$ alkenyl substituted with 0–3 $R^{5b}$; or
$C_2$–$C_6$ alkynyl substituted with 0–3 $R^{5b}$;

$R^{5b}$, at each occurrence, is independently selected from: H, methyl, ethyl, propyl, butyl, $CF_3$, Cl, F, Br, I, =O; $C_3$–$C_6$ carbocycle substituted with 0–3 $R^{5c}$; phenyl substituted with 0–3 $R^{5c}$; or
5 to 6 membered heterocycle containing 1 to 3 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

Ring B is

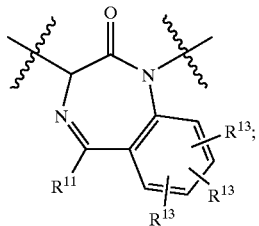

$R^{11}$, at each occurrence, is independently selected from H, =O, $NR^{18}R^{19}$, $CF_3$;
$C_1$–$C_4$ alkyl optionally substituted with 0–1 $R^{11a}$;
phenyl substituted with 0–3 $R^{11b}$;
$C_3$–$C_6$ carbocycle substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, phenoxy, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond;
X is a bond;
Y is a bond;
Z is H;
$C_1$–$C_4$ alkyl substituted with 0–3 $R^{12a}$;
$C_2$–$C_4$ alkenyl substituted with 0–3 $R^{12a}$; or
$C_2$–$C_4$ alkynyl substituted with 0–3 $R^{12a}$;

$R^{12a}$, at each occurrence, is independently selected from H, OH, Cl, F, $NR^{15}R^{16}$, $CF_3$, acetyl, $SCH_3$, S(=O)$CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_4$ alkyl, or $C_2$–$C_4$ alkoxyalkyl;

$R^{14a}$ is H, phenyl, benzyl, or $C_1$–$C_4$ alkyl;

$R^{15}$, at each occurrence, is independently selected from H, $C_1$–$C_4$ alkyl, and benzyl;

$R^{16}$, at each occurrence, is independently selected from H, OH, methyl, ethyl, propyl, butyl, benzyl, phenethyl, methyl-C(=O)$_2$—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl;

$R^{21}$ is H, phenyl, benzyl, methyl, ethyl, propyl, or butyl; and $R^{22}$ is methyl, ethyl, propyl, butyl, propenyl, butenyl, and propargyl.

6. A compound according to claim 5 or a pharmaceutically acceptable salt thereof wherein:

Q is —$CH_2R_4$, —O—$R_4$, or —$CH_2$—NH—$R^4$;

$R^4$ is $C_1$–$C_6$ alkyl substituted with 0–2 $R^{4a}$, $C_2$–$C_6$ alkenyl substituted with 0–2 $R^{4a}$, $C_2$–$C_6$ alkynyl substituted with 0–2 $R^{4a}$, or
$C_3$–$C_6$ cycloalkyl substituted with 0–3 $R^{4b}$;

$R^{4a}$, at each occurrence, is independently selected from is H, OH, F, Cl, Br, I, CN, $NR^{15}R^{16}$, $CF_3$, methyl, ethyl, propyl, methoxy, ethoxy, propoxy, $OCF_3$;
$C_3$–$C_6$ carbocycle substituted with 0–3 $R^{4b}$, phenyl substituted with 0–3 $R^{4b}$, or
5 to 6 membered heterocycle containing 1 to 3 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, Br, I, CN, $NO_2$, $NR^{15}R^{16}$, $CF_3$, acetyl, $SCH_3$, S(=O)$CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ is H;
$C_1$–$C_4$ alkyl substituted with 0–1 $R^{5b}$;
$C_2$–$C_4$ alkenyl substituted with 0–1 $R^{5b}$; or
$C_2$–$C_4$ alkynyl substituted with 0–1 $R^{5b}$;

$R^{5b}$, at each occurrence, is independently selected from: H, methyl, ethyl, propyl, butyl, $CF_3$;
$C_3$–$C_6$ carbocycle substituted with 0–2 $R^{5c}$;

phenyl substituted with 0–3 $R^{5c}$; and 5 to 6 membered heterocycle containing 1 to 3 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, $C_1$–$C_4$ alkyl, $C_1$–$C_3$ alkoxy, $C_1$–$C_2$ haloalkyl, and $C_1$–$C_2$ haloalkoxy;

Ring B is $R^{11}$, at each occurrence, is independently selected from H, =O, $NR^{18}R^{19}$;
$C_1$–$C_4$ alkyl optionally substituted with 0–1 $R^{11a}$;
phenyl substituted with 0–3 $R^{11b}$;

5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, methyl, ethyl, propyl, methoxy, ethoxy, propoxy, phenoxy, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond;
X is a bond;
Y is a bond;
Z is H;
$C_1$–$C_4$ alkyl substituted with 0–1 $R^{12a}$;
$C_2$–$C_4$ alkenyl substituted with 0–1 $R^{12a}$; or
$C_2$–$C_4$ alkynyl substituted with 0–1 $R^{12a}$;

$R^{12a}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl; and $R^{16}$, at each occurrence, is independently selected from H, OH, methyl, ethyl, propyl, butyl, benzyl, and phenethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

7. A compound according to claim 6 wherein:

$R^5$ is —$CH_3$, —$CH_2CH_3$, —$CH_2CH_2CH_3$, —$CH_2CH(CH_3)_2$, —$CH_2CH_2CH_2CH_3$, —$CH_2CH_2CH_2CH_2CH_3$, —$CH_2CH_2CH(CH_3)_2$, —$CH_2CH_2CH_2CH_2CH_2CH_3$, —$CH_2CH_2CH_2CH(CH_3)_2$, —$CH_2CH_2CH_2CH_2CH(CH_3)_2$, —$CH_2NH_2$, —$CH_2N(CH_3)_2$, —$CH_2N(CH_2CH_3)_2$, —$CH_2CH_2NH_2$, —$CH_2CH_2N(CH_3)_2$, —$CH_2CH_2N(CH_2CH_3)_2$, —$CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, or —$CH_2CH_2$-cyclohexyl;

Q is —$CH_3$, —$CH_2CH_3$, —$CH_2CH_2CH_3$, —$CH_2CH(CH_3)_2$, —$CH_2CH_2CH_2CH_3$, —$CH_2CH_2CH_2CH_2CH_3$, —$CH_2CH_2CH(CH_3)_2$, —$CH_2CH_2CH_2CH_2CH_2CH_3$, —$CH_2CH_2CH_2CH(CH_3)_2$, —$CH_2CH_2CH_2CH_2CH_2CH_2CH_3$, —$CH_2CH_2CH_2CH_2CH(CH_3)_2$, —$CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, —$CH_2CH_2$-cyclohexyl, —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH_2CH_2CH_2CH(CH_3)_2$, —$OCH_2CH_2CH_2CH_3$, —$OCH_2CH_2CH_2CH_2CH_2CH_3$, —$OCH_2CH_2CH_2CH(CH_3)_2$, —$OCH_2CH_2CH_2CH_2CH(CH_{32}$, —$OCH_2$-cyclopropyl, —$OCH_2$-cyclobutyl, —$OCH_2$-cyclopentyl, —$OCH_2$-cyclohexyl, —$OCH_2CH_2$-cyclopropyl, —$OCH_2CH_2$-cyclobutyl, —$OCH_2CH_2$-cyclopentyl, —$OCH_2CH_2$-cyclohexyl, —$CH_2OCH_2CH_3$, —$CH_2OCH_2CH_2CH_3$, —$CH_2$—$OCH(CH_3)_2$, —$CH_2OCH_2CH_2CH_2CH_3$, —$CH_2OCH_2CH(CH_3)_2$, —$CH_2OCH_2CH_2CH_2CH_3$, —$CH_2OCH_2CH_2CH(CH_3)_2$, —$CH_2OCH_2CH_2CH_2CH(CH_3)_2$, —$CH_2O$-cyclopropyl, —$CH_2O$-cyclobutyl, —$CH_2O$-cyclopentyl, —$CH_2O$-cyclohexyl, —$CH_2OCH_2$-cyclopropyl, —$CH_2OCH_2$-cyclobutyl, —$CH_2OCH_2$-cyclopentyl, —$CH_2OCH_2$-cyclohexyl; —$CH_2(NH)CH_3$, —$CH_2(NH)CH_2CH_3$, —$CH_2(NH)CH_2CH_2CH_3$, —$CH_2$—$(NH)CH(CH_3)_2$, —$CH_2(NH)CH_2CH_2CH_2CH_3$, —$CH_2(NH)CH_2CH(CH_3)_2$, —$CH_2(NH)CH_2CH_2CH_2CH_3$, —$CH_2(NH)CH_2CH_2CH_2CH_2CH_3$, —$CH_2(NH)CH_2CH_2CH(CH_3)_2$, —$CH_2(NH)CH_2CH_2CH_2CH(CH_3)_2$, —$CH_2(NH)$-cyclopropyl, —$CH_2(NH)$-cyclobutyl, —$CH_2(NH)$-cyclopentyl, —$CH_2(NH)$-cyclohexyl, —$CH_2(NH)CH_2$-cyclopropyl, —$CH_2(NH)CH_2$-cyclobutyl, —$CH_2(NH)CH_2$-cyclopentyl, or —$CH_2(NH)CH_2$-cyclohexyl;

W is a bond;
X is a bond;
Y is a bond;
Z is methyl, ethyl, i-propyl, n-propyl, n-butyl, i-butyl, s-butyl, t-butyl, or allyl;

$R^{11}$, at each oocurrence, is independently selected from H, =O, methyl, ethyl, phenyl, benzyl, phenethyl, 4-F-phenyl, (4-F-phenyl)$CH_2$—, (4-F-phenyl)$CH_2CH_2$—, 3-F-phenyl, (3-F-phenyl)$CH_2$—, (3-F-phenyl)$CH_2CH_2$—, 2-F-phenyl, (2-F-phenyl)$CH_2$—, (2-F-phenyl)$CH_2CH_2$—, 4-Cl-phenyl, (4-Cl-phenyl)$CH_2$—, (4-Cl-phenyl)$CH_2CH_2$—, 3-Cl-phenyl, (3-Cl-phenyl)

CH$_2$—, (3-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 3-CH$_3$-phenyl, (3-CH$_3$-phenyl)CH$_2$—, (3-CH$_3$-phenyl)CH$_2$CH$_2$—, 4-CF$_3$-phenyl, (4-CF$_3$-phenyl)CH$_2$—, (4-CF$_3$-phenyl)CH$_2$CH$_2$—, pyrid-2-yl, 4-F-pyrid-2-yl, 4-Cl-pyrid-2-yl, 4-CH$_3$-pyrid-2-yl, 4-CF$_3$-pyrid-2-yl, pyrid-3-yl, 4-F-pyrid-3-yl, 4-Cl-pyrid-3-yl, 4-CH$_3$-pyrid-3-yl, 4-CF$_3$-pryid-3-yl, or pyrid-4-yl; and $R^{13}$, at each occurrence, is independently selected from H, F, Cl, OH, —CH$_3$,—CH$_2$CH$_3$, —OCH$_3$, or —CF$_3$.

8. A compound according to claim 2 of Formula (I) or a pharmaceutically acceptable salt thereof wherein:

Q is —(CH$_2$)$_m$—R$^4$, —(CH$_2$)$_n$—S—R$^4$, —(CH$_2$)$_n$—O—R$^4$, or
—(CH$_2$)$_m$—N(H)—R$^4$;

m is 1 or 2;

n is 0 or 1;

$R^4$ is C$_1$–C$_8$ alkyl substituted with 0–3 $R^{4a}$,
C$_2$–C$_8$ alkenyl substituted with 0–3 $R^{4a}$,
C$_2$–C$_8$ alkynyl substituted with 0–3 $R^{4a}$,
C$_3$–C$_{10}$ carbocycle substituted with 0–3 $R^{4b}$,
aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from is H, Cl, F, Br, I, CN, NO$_2$, NR$^{15}$R$^{16}$, CF$_3$, C(=O)OR$^{22}$, SR$^{22}$, OR$^{22}$, OR$^{14a}$, NR$^{21}$R$^{22}$, S(=O)R$^{22}$, S(=O)$_2$R$^{22}$, C$_1$–C$_6$ alkyl, C$_1$–C$_4$ alkoxy, C$_1$–C$_4$ haloalkyl, C$_1$–C$_4$ haloalkoxy, C$_1$–C$_4$ haloalkyl-S—,
C$_3$–C$_{10}$ carbocycle substituted with 0–3 $R^{4b}$,
aryl substituted with 0–3 $R^{4b}$, and
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

$R^5$ is H;
C$_1$–C$_6$ alkyl substituted with 0–3 $R^{5b}$;
C$_2$–C$_6$ alkenyl substituted with 0–3 $R^{5b}$;
C$_2$–C$_6$ alkynyl substituted with 0–3 $R^{5b}$;
C$_3$–C$_{10}$ carbocycle substituted with 0–3 $R^{5c}$;
aryl substituted with 0–3 $R^{5c}$; and
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from: H, C$_1$–C$_6$ alkyl, CF$_3$, Cl, F, Br, I, =O, CN, NO$_2$, NR$^{15}$R$^{16}$;
C$_3$–C$_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
C$_1$–C$_6$ alkyl, C$_1$–C$_4$ alkoxy, C$_1$–C$_4$ haloalkyl, and C$_1$–C$_4$ haloalkoxy;

Ring B is

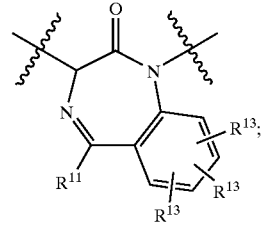

$R^{11}$, at each occurrence, is independently selected from H, =O, NR$^{18}$R$^{19}$, CF$_3$;
C$_1$–C$_4$ alkyl optionally substituted with 0–3 $R^{11a}$;
phenyl substituted with 0–3 $R^{11b}$;
C$_3$–C$_6$ carbocycle substituted with 0–3 $R^{11b}$; or
5 to 6 membered heterocycle containing 1 to 3 heteroatoms selected from nitrogen, oxygen, and sulphur, wherein said 5 to 6 membered heterocycle is substituted with 0–3 $R^{11b}$; and wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, C$_1$–C$_4$ alkyl, OR$^{14}$, Cl, F, =O, CN, NO$_2$, NR$^{15}$R$^{16}$, CF$_3$, or phenyl substituted with 0–3 $R^{11b}$;

$R^{11b}$, at each occurrence, is independently selected from H, OH, Cl, F, NR$^{15}$R$^{16}$, CF$_3$, methyl, ethyl, propyl, butyl, methoxy, ethoxy, propoxy, C$_1$–C$_2$ haloalkyl, and C$_1$–C$_4$ haloalkoxy;

W is a bond, —CH$_2$—, —CH$_2$CH$_2$—;

X is a bond;
phenyl substituted with 0–2 $R^{Xb}$;
C$_3$–C$_6$ cycloalkyl substituted with 0–2 $R^{Xb}$; or
5 to 6 membered heterocycle substituted with 0–2 $R^{Xb}$;

$R^{Xb}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, C$_1$–C$_4$ alkyl, C$_1$–C$_3$ alkoxy, C$_1$–C$_2$ haloalkyl, and C$_1$–C$_2$ haloalkoxy;

Y is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, —S(=O)NR$^{19b}$—, —C(=O)O—, or —OC(=O)—;

Z is C$_1$–C$_3$ alkyl substituted with 1–2 $R^{12a}$;
aryl substituted with 0–4 $R^{12b}$;
C$_3$–C$_{10}$ carbocycle substituted with 0–3 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from aryl substituted with 0–4 $R^{12b}$;
C$_3$–C$_{10}$ carbocycle substituted with 0–4 $R^{12b}$; and
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R_{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_4$ alkyl)-C(=O)—, and ($C_1$–$C_4$ alkyl)-S(=O)$_2$—;

$R^{16}$, at each occurrence, is independently selected from H, OH, $C_1$–$C_6$ alkyl, benzyl, phenethyl, ($C_1$–$C_4$ alkyl)-C(=O)—, and ($C_1$–$C_4$ alkyl)-S(=O)$_2$—; and alternatively, $R^{15}$ and $R^{16}$, together with the nitrogen to which they are attached, may combine to form a 4–6 membered ring wherein said 4–6 membered ring optionally contains an additional heteroatom selected from O or NH, wherein said 4–6 membered ring is selected from imidazolidinyl, oxazolidinyl, thiazolidinyl, piperazinyl, morpholinyl, and thiomorpholinyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, and phenethyl;

$R^{21}$ is H, phenyl, benzyl, methyl, ethyl, propyl, or butyl; and $R^{22}$ is methyl, ethyl, propyl, butyl, propenyl, butenyl, and propargyl.

9. A compound according to claim 8 wherein:

Q is —$CH_2R^4$, —O—$R^4$, or —$CH_2$—NH—$R^4$;

$R^4$ is $C_1$–$C_6$ alkyl substituted with 0–3 $R^{4a}$;
 $C_2$–$C_6$ alkenyl substituted with 0–3 $R^{4a}$;
 $C_2$–$C_6$ alkynyl substituted with 0–3 $R^{4a}$;
 $C_3$–$C_6$ carbocycle substituted with 0–3 $R^{4b}$;
 phenyl substituted with 0–3 $R^{4b}$, or
 5 to 6 membered heterocycle containing 1 to 3 heteroatoms selected from nitrogen, oxygen, and sulphur, wherein said 5 to 6 membered heterocycle is substituted with 0–3 $R^{4b}$;

$R^{4a}$, at each occurrence, is independently selected from H, Cl, F, Br, I, CN, $NO_2$, $NR^{15}R^{16}$, $CF_3$, C(=O)$OR^{22}$, $SR^{22}$, $OR^{14a}$, $OR^{22}$, $NR^{21}R^{22}$, S(=O)$R^{22}$, S(=O)$_2R^{22}$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_3$–$C_{10}$ carbocycle substituted with 0–3 $R^{4b}$, aryl substituted with 0–3 $R^{4b}$, and 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ is H;
 $C_1$–$C_6$ alkyl substituted with 0–3 $R^{5b}$;
 $C_2$–$C_6$ alkenyl substituted with 0–3 $R^{5b}$; or
 $C_2$–$C_6$ alkynyl substituted with 0–3 $R^{5b}$;

$R^{5b}$, at each occurrence, is independently selected from: H, methyl, ethyl, propyl, butyl, $CF_3$, Cl, F, Br, I, =O;
 $C_3$–$C_6$ carbocycle substituted with 0–3 $R^{5c}$;
 phenyl substituted with 0–3 $R^{5c}$; or
 5 to 6 membered heterocycle containing 1 to 3 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_4$ alkyl, $C_1$–$C_3$ alkoxy, $C_1$–$C_2$ haloalkyl, and $C_1$–$C_2$ haloalkoxy;

Ring B is $R^{11}$ at each occurrence, is independently selected from H, =O, $NR^{18}R^{19}$, $CF_3$;
 $C_1$–$C_4$ alkyl optionally substituted with 0–3 $R^{11a}$;
 phenyl substituted with 0–3 $R^{11b}$;
 $C_3$–$C_6$ carbocycle substituted with 0–3 $R^{11b}$; or
 5 to 6 membered heterocycle containing 1 to 3 heteroatoms selected from nitrogen, oxygen, and sulphur, wherein said 5 to 6 membered heterocycle is substituted with 0–3 $R^{11b}$; and wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, phenoxy, Cl, F, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_4$ haloalkoxy;

W is a bond, —$CH_2$—, —$CH_2CH_2$—;

X is a bond;
 phenyl substituted with 0–1 $R^{Xb}$;
 $C_3$–$C_6$ cycloalkyl substituted with 0–1 $R^{Xb}$; or
 5 to 6 membered heterocycle substituted with 0–1 $R^{Xb}$;

$R^{Xb}$ is selected from H, OH, Cl, F, $NR^{15}R^{16}$, $CF_3$, acetyl, $SCH_3$, S(=O)$CH_3$, S(=O)$_2CH_3$, methyl, ethyl, propyl, methoxy, ethoxy, propoxy, and —$OCF_3$;

Y is a bond, —C(=O)—, —O—, —S—, —S(=O)—, —S(=O)$_2$—, —NH—, —N($CH_3$)—, or —N($CH_2CH_3$)—;

Z is $C_1$–$C_2$ alkyl substituted with 1–2 $R^{12a}$;
 aryl substituted with 0–4 $R^{12b}$;
 $C_3$–$C_{10}$ carbocycle substituted with 0–3 $R^{12b}$; or
 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from aryl substituted with 0–4 $R^{12b}$;
 $C_3$–$C_{10}$ carbocycle substituted with 0–4 $R^{12b}$; and
 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_4$ alkyl, or $C_2$–$C_4$ alkoxyalkyl;

$R^{14a}$ is H, phenyl, benzyl, or $C_1$–$C_4$ alkyl;

$R^{15}$, at each occurrence, is independently selected from H, $C_1$–$C_4$ alkyl, and benzyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl; and $R^{21}$ is H, phenyl, benzyl, methyl, ethyl, propyl, or butyl; and $R^{22}$ is methyl, ethyl, propyl, butyl, propenyl, butenyl, and propargyl.

10. A compound according to claim 9 or a pharmaceutically acceptable salt thereof wherein:

Q is —$CH_2R_4$, —O—$R_4$, or —$CH_2$—NH—$R^4$;

$R^4$ is $C_1$–$C_6$ alkyl substituted with 0–2 $R^{4a}$, $C_2$–$C_6$ alkenyl substituted with 0–2 $R^{4a}$, $C_2$–$C_6$ alkynyl substituted with 0–2 $R^{4a}$, or
$C_3$–$C_6$ cycloalkyl substituted with 0–3 $R^{4b}$;

$R^{4a}$, at each occurrence, is independently selected from is H, OH, F, Cl, Br, I, CN, $NR^{15}NR^{16}$, $CF_3$, methyl, ethyl, propyl, butyl, methoxy, ethoxy, propoxy, $OCF_3$;
$C_3$–$C_6$ carbocycle substituted with 0–3 $R^{4b}$, phenyl substituted with 0–3 $R^{4b}$, or
5 to 6 membered heterocycle containing 1 to 3 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, irnidazolyl, oxazolyl, isoxazolyl, and tetrazolyl;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ is H;
$C_1$–$C_4$ alkyl substituted with 0–1 $R^{5b}$;
$C_2$–$C_4$ alkenyl substituted with 0–1 $R^{5b}$; or
$C_2$–$C_4$ alkynyl substituted with 0–1 $R^{5b}$;

$R^{5b}$, at each occurrence, is independently selected from: H, methyl, ethyl, propyl, butyl, $CF_3$;
$C_3$–$C_6$ carbocycle substituted with 0–2 $R^{5c}$;
phenyl substituted with 0–3 $R^{5c}$; and
5 to 6 membered heterocycle containing 1 to 3 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, $C_1$–$C_4$ alkyl, $C_1$–$C_3$ alkoxy, $C_1$–$C_2$ haloalkyl, and $C_1$–$C_2$ haloalkoxy;

Ring B is

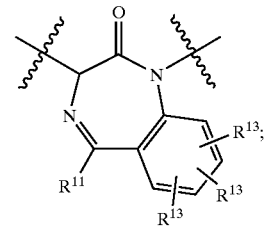

$R^{11}$, at each occurrence, is independently selected from H, =O, $NR^{13}R^{19}$;
$C_1$–$C_4$ alkyl optionally substituted with 0–3 $R^{11a}$;
phenyl substituted with 0–3 $R^{11b}$;
$C_3$–$C_6$ carbocycle substituted with 0–3 $R^{11b}$; or
5 to 6 membered heterocycle containing 1 to 3 heteroatoms selected from nitrogen, oxygen, and sulphur, wherein said 5 to 6 membered heterocycle is substituted with 0–3 $R^{11b}$; and wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, phenoxy, Cl, F, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond or —$CH_2$—;

X is a bond;
phenyl substituted with 0–1 $R^{Xb}$;
$C_3$–$C_6$ cycloalkyl substituted with 0–1 $R^{Xb}$; or
5 to 6 membered heterocycle substituted with 0–1 $R^{Xb}$;

$R^{Xb}$ is selected from H, OH, Cl, F, $NR^{15}R^{16}$, $CF_3$, acetyl, methyl, ethyl, methoxy, ethoxy, and —$OCF_3$;

Y is a bond, —C(=O)—, —O—, —S—, —S(=O)—, —S(=O)$_2$—, —NH—, —N(CH$_3$)—, or —N(CH$_2$CH$_3$)—;

Z is $C_1$–$C_2$ alkyl substituted with 1–2 $R^{12a}$;
aryl substituted with 0–4 $R^{12b}$;
$C_3$–$C_{10}$ carbocycle substituted with 0–3 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from aryl substituted with 0–4 $R^{12b}$;
$C_3$–$C_{10}$ carbocycle substituted with 0–4 $R^{12b}$; and
5 to 10 membered heterocycle containing 1 to 4 heteroatoms selected from nitrogen, oxygen, and sulphur, wherein said 5 to 10 membered heterocycle is substituted with 0–3 $R^{12b}$; and wherein said 5 to 10 membered heterocycle is selected from pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, and $—OCF_3$;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl; and $R^{16}$, at each occurrence, is independently selected from H, OH, methyl, ethyl, propyl, butyl, benzyl, and phenethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

11. A compound, according to claim 10, wherein:

$R^5$ is $—CH_3$, $—CH_2CH_3$, $—CH_2CH_2CH_3$, $—CH_2CH(CH_3)_2$, $—CH_2CH_2CH_2CH_3$, $—CH_2CH_2CH_2CH_2CH_3$, $—CH_2CH_2CH(CH_3)_2$, $—CH_2CH_2CH_2CH_2CH_2CH_3$, $—CH_2CH_2CH_2CH(CH_3)_2$, $—CH_2CH_2CH_2CH_2CH(CH_3)_2$, $—CH_2NH_2$, $—CH_2N(CH_3)_2$, $—CH_2N(CH_2CH_3)_2$, $—CH_2CH_2NH_2$, $—CH_2CH_2N(CH_3)_2$, $—CH_2CH_2N(CH_2CH_3)_2$, $—CH_2$-cyclopropyl, $—CH_2$-cyclobutyl, $—CH_2$-cyclopentyl, $—CH_2$cyclohexyl, $—CH_2CH_2$-cyclopropyl, $—CH_2CH_2$-cyclobutyl, $—CH_2CH_2$-cyclopentyl, or $—CH_2CH_2$-cyclohexyl;

Q is $—CH_3$, $—CH_2CH_3$, $—CH_2CH_2CH_3$, $—CH_2CH(CH_3)_2$, $—CH_2CH_2CH_2CH_3$, $—CH_2CH_2CH_2CH_2CH_3$, $—CH_2CH_2CH(CH_3)_2$, $—CH_2CH_2CH_2CH_2CH_2CH_3$, $—CH_2CH_2CH_2CH(CH_3)_2$, $—CH_2CH_2CH_2CH_2CH_2CH_2CH_3$, $—CH_2CH_2CH_2CH_2CH(CH_3)_2$, $—CH_2$-cyclopropyl, $—CH_2$-cyclobutyl, $—CH_2$-cyclopentyl, $—CH_2$-cyclohexyl, $—CH_2CH_2$-cyclopropyl, $—CH_2CH_2$-cyclobutyl, $—CH_2CH_2$-cyclopentyl, $—CH_2CH_2$-cyclohexyl, $—OCH_3$, $—OCH_2CH_3$, $—OCH_2CH_2CH_3$, $—OCH(CH_3)_2$, $—OCH_2CH_2CH_2CH_3$, $—OCH_2CH(CH_3)_2$, $—OCH_2CH_2CH(CH_3)_2$, $—OCH_2CH_2CH_2CH_2CH_3$, $—OCH_2CH_2CH_2CH_2CH_2CH_3$, $—OCH_2CH_2CH_2CH(CH_3)_2$, $—OCH_2CH_2CH_2CH_2CH(CH_3)_2$, $—OCH_2$-cyclopropyl, $—OCH_2$cyclobutyl, $—OCH_2$-cyclopentyl, $—OCH_2$-cyclohexyl, $—OCH_2CH_2$-cyclopropyl, $—OCH_2CH_2$-cyclobutyl, $—OCH_2CH_2$-cyclopentyl, $—OCH_2CH_2$-cyclohexyl, $—CH_2OCH_2CH_3$, $—CH_2OCH_2CH_2CH_3$, $—Ch_2—OCH(CH_3)_2$, $—CH_2OCH_2CH_2CH_2CH_3$, $—CH_2OCH_2CH(CH_3)_2$, $—CH_2OCH_2CH_2CH_2CH_3$, $—CH_2OCH_2CH_2CH(CH_3)_2$, $—CH_2OCH_2CH_2CH_2CH(CH_3)_2$, $—CH_2O$-cyclopropyl, $—CH_2O$-cyclobutyl, $—CH_2O$-cyclopentyl, $—CH_2O$-cyclohexyl, $—CH_2OCH_2$-cyclopropyl, $—CH_2OCH_2$-cyclobutyl, $—CH_2OCH_2$-cyclopentyl, $—CH_2OCH_2$-cyclohexyl, $—CH_2(NH)CH_3$, $—CH_2(NH)CH_2CH_3$, $—CH_2(NH)CH_2CH_2Ch_3$, $—CH_2—(NH)CH(CH_3)_2$, $—CH_2(NH)CH_2CH_2CH_2CH_3$, $—CH_2(NH)CH_2CH(CH_3)_2$, $—CH_2(NH)CH_2CH_2CH_2CH_2CH_3$, $—CH_2(NH)CH_2CH_2CH(CH_3)_2$, $—CH_2(NH)CH_2CH_2CH_2CH(CH_3)_2$, $—CH_2(NH)$-cyclopropyl, $—CH_2(NH)$-cyclobutyl, $—CH_2(NH)$-cyclopentyl, $—CH_2(NH)$-cyclohexyl, $—CH_2(NH)CH_2$-cyclopropyl, $—CH_2(NH)CH_2$-cyclobutyl, $—CH_2(NH)CH_2$-cyclopentyl, or $—Ch_2(NH)CH_2$-cyclohexyl;

W is a bond or $—CH_2—$;

X is a bond;

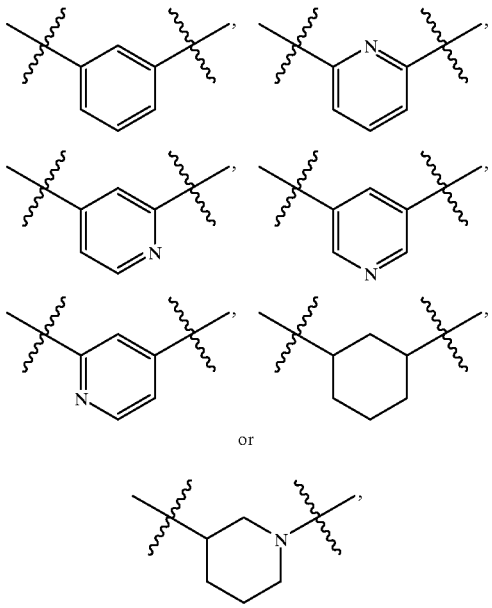

or

Y is a bond, $—C(=O)—$, $—O—$, $—S—$, $—S(=O)_2—$, $—NH—$, or $—N(CH_3)—$,

Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-$CF_3$O-phenyl, 3-$CF_3$O-phenyl, 4-$CF_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—, (2-MeO-phenyl)$CH_2$—, (3-MeO-phenyl)$CH_2$—, (4-MeO-phenyl)$CH_2$—, (2-Me-phenyl)$CH_2$—, (3-Me-phenyl)$CH_3$—, (4-Me-phenyl)$CH_2$—, (2-MeS-phenyl)$CH_2$—, (3-MeS-phenyl)

CH$_2$—, 4-MeS-phenyl)CH$_2$—, (2-CF$_3$O-phenyl) CH$_2$—, (3-CF$_3$O-phenyl)CH$_2$—, (4-CF$_3$O-phenyl) CH$_2$—, (furanyl)CH$_2$—, (thienyl)CH$_2$—, (pyridyl) CH$_2$—, (2-Me-pyridyl)CH$_2$—, (3-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, (cyclopropyl)CH$_2$—, (cyclobutyl)CH$_2$—, (cyclopentyl)CH$_2$—, (cyclohexyl) CH$_2$—, (morpholino)CH$_2$—, (N-pipridinyl)CH$_2$—, or (phenyl)$_2$CH—;

R$^{11}$, at each occurrence, is independently selected from H, =O, methyl, ethyl, phenyl, benzyl, phenethyl, 4-F-phenyl, (4-F-phenyl)CH$_2$—, (4-phenyl)CH$_2$CH$_2$—, 3-F-phenyl, (3-F-phenyl)CH$_2$—, (3-F-phenyl) CH$_2$CH$_2$—, 2-F-phenyl, (2-F-phenyl)CH$_2$—, (2-F-phenyl)CH$_2$CH$_2$—, 4-Cl-phenyl, (4-Cl-phenyl)CH$_2$—, (4-Cl-phenyl)CH$_2$CH$_2$—, 3-Cl-phenyl, (3-Cl-phenyl) CH$_2$—, (3-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 3-CH$_3$-phenyl, (3-CH$_3$-phenyl)CH$_2$—, (3-CH$_3$-phenyl)CH$_2$CH$_2$—, 4-CF$_3$-phenyl, (4-CF$_3$-phenyl) CH$_2$—, (4-CF$_3$-phenyl)CH$_2$CH$_2$—, pyrid-2-yl, 4-F-pyrid-2-yl, 4-Cl-pyrid-2-yl, 4-CH$_3$-pyrid-2-yl, 4-CF$_3$-pyrid-2-yl, pyrid-3-yl 4-F-pyrid-3-yl, 4-Cl-pyrid-3-yl, 4-CH$_3$-pyrid-3-yl, 4-CF$_3$-pyrid-3yl, or pyrid-4-yl; and R$^{13}$, at each occurrence, is independently selected from H, F, Cl, OH, —CH$_3$, —CH$_2$CH$_3$, —OCH$_3$, or —CF$_3$.

12. A compound according to one of claims 4–11 of Formula (Id):

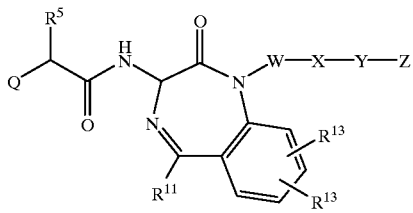

(Id)

or a stereoisomer, pharmaceutically acceptable salt thereof.

13. A compound according to claim 1, or a pharmaceutically acceptable salt thereof, selected from:
(3S)-3-[(1-oxo-(2S)-2-cyclopropylmethyl-heptyl)]amino-1-methyl-5-phenyl-2,3-dihydro-1H-1,4-benzodiazepin-2-one;
(3S)-3-[(1-oxo-2-propyloctyl)]amino-1-methyl-5-phenyl-2,3-dihydro-1H-1,4-benzodiazepin-2-one;
(3S)-3-[(1-oxo-2-propylnonanyl)]amino-1-methyl-5-phenyl-2,3-dihydro-1H-1,4-benzodiazepin-2-one;
(3S)-3-[(1-oxo-2-butyloctyl)]amino-1-methyl-5-phenyl-2,3-dihydro-1H-1,4-benzodiazepin-2-one;
(3S)-3-(1-oxo-2-methyloctyl)amino-1-methyl-5-phenyl-2,3-dihydro-1H-1,4-benzodiazepin-2-one;
(3S)-3-[(1-oxo-2-pentylheptanyl)]amino-1-methyl-5-phenyl-2,3-dihydro-1H-1,4-benzodiazepin-2-one;
(3S)-3-[(1-oxo-2-propylpentyl)]amino-1-methyl-5-phenyl-2,3-dihydro-1H-1,4-benzodiazepin-2-one;
(3S)-3-[(1-oxo-2-methylpentyl)amino]-1-methyl-5-phenyl-2,3-dihydro-1H-1,4-benzodiazepin-2-one;
3-[1-oxo-2-(S)-cyclopropylmethyl-heptyl]amino-1-methyl-5-(pyridin-2-yl)-2,3-dihydro-1H-1,4-benzodiazepine-2-one;
3-[1-oxo-2-(S)-cyclopropylmethyl-heptyl]amino-1-methyl-5-[4-methyl (pyridin-2-yl)]-2,3-dihydro-1H-1,4-benzodiazepin-2-one;
3-[1-oxo-2-(S)-cyclopropylmethyl-heptyl]amino-1-methyl-5-[4-trifluoromethyl(pyridin-2-yl)]-2,3-dihydro-1H-1,4-benzodiazepin-2-one;
3-[1-oxo-2-(S)-aminomethyl-heptyl]amino-1-methyl-(5-trifluoromethyl-phenyl)-2,3-dihydro-1H-1,4-benzodiazepine-2-one;
3-[1-oxo-2-(S)-(dimethylamino)methyl-heptyl]amino-1-methyl-5-(trifluoromethyl-phenyl)-2,3-dihydro-1H-1,4-benzodiazepine-2-one; and
3-(3-isopentyloxy-2-(R)-methyl-1-oxo-propyl)amino-1-methyl-5-(trifluoromethyl)phneyl-2,3-dihydro-1H-1,4-benzodiazepin-2-one.

14. A pharmaceutical composition comprising a compound of claim 1 and a pharmaceutically acceptable carrier.

15. A method for the treatment of Alzheimer's Disease comprising administering to a host in need of such treatment a therapeutically effective amount of a compound of claim 1.

16. A method for the treatment of Alzheimer's Disease comprising administering to a host in need of such treatment a therapeutically effective amount of a compound of claim 2.

17. A method for the treatment of Alzheimer's Disease comprising administering to a host in need of such treatment a therapeutically effective amount of a compound of claim 3.

18. A method for the treatment of Alzheimer's Disease comprising administering to a host in need of such treatment a therapeutically effective amount of a compound of claim 4.

19. A method for the treatment of Alzheimer's Disease comprising administering to a host in need of such treatment a therapeutically effective amount of a compound of claim 5.

20. A method for the treatment of Alzheimer's Disease comprising administering to a host in need of such treatment a therapeutically effective amount of a compound of claim 6.

21. A method for the treatment of Alzheimer's Disease comprising administering to a host in need of such treatment a therapeutically effective amount of a compound of claim 7.

22. A method for the treatment of Alzheimer's Disease comprising administering to a host in need of such treatment a therapeutically effective amount of a compound of claim 8.

23. A method for the treatment of Alzheimer's Disease comprising administering to a host in need of such treatment a therapeutically effective amount of a compound of claim 9.

24. A method for the treatment of Alzheimer's Disease comprising administering to a host in need of such treatment a therapeutically effective amount of a compound of claim 10.

25. A method for the treatment of Alzheimer's Disease comprising administering to a host in need of such treatment a therapeutically effective amount of a compound of claim 11.

26. A method for the treatment of Alzheimer's Disease comprising administering to a host in need of such treatment a therapeutically effective amount of a compound of claim 12.

27. A method for the treatment of Alzheimer's Disease comprising administering to a host in need of such treatment a therapeutically effective amount of a compound of claim 13.

* * * * *